(12) United States Patent (10) Patent No.: US 11,392,046 B2
Kamimura (45) Date of Patent: Jul. 19, 2022

(54) QUALITY INSPECTION METHOD FOR CHEMICAL LIQUID

(71) Applicant: FUJIFILM Corporation, Tokyo (JP)

(72) Inventor: Tetsuya Kamimura, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 528 days.

(21) Appl. No.: 16/502,032

(22) Filed: Jul. 3, 2019

(65) Prior Publication Data

US 2019/0324373 A1 Oct. 24, 2019

Related U.S. Application Data

(63) Continuation of application No. PCT/JP2017/047208, filed on Dec. 28, 2017.

(30) Foreign Application Priority Data

Jan. 6, 2017 (JP) .............................. JP2017-001181
Dec. 27, 2017 (JP) .............................. JP2017-251121

(51) Int. Cl.
| | |
|---|---|
| *G03F 7/20* | (2006.01) |
| *G01N 33/2028* | (2019.01) |
| *G01N 21/31* | (2006.01) |
| *G01N 24/08* | (2006.01) |
| *G01N 30/06* | (2006.01) |
| *G01N 30/72* | (2006.01) |
| *G01N 33/44* | (2006.01) |
| *G01N 1/38* | (2006.01) |
| *G01N 30/02* | (2006.01) |
| *H01L 21/66* | (2006.01) |

(52) U.S. Cl.
CPC ........ *G03F 7/7065* (2013.01); *G01N 21/3103* (2013.01); *G01N 24/08* (2013.01); *G01N 30/06* (2013.01); *G01N 30/7206* (2013.01); *G01N 30/7233* (2013.01); *G01N 33/2028* (2019.01); *G01N 33/442* (2013.01); *G01N 2001/386* (2013.01); *G01N 2030/025* (2013.01); *G01N 2030/027* (2013.01); *H01L 22/10* (2013.01)

(58) Field of Classification Search
CPC ....... G01N 2001/386; G01N 2030/025; G01N 2030/027; G01N 21/3103; G01N 24/08; G01N 30/06; G01N 30/7206; G01N 30/7233; G01N 33/2028; G01N 33/442; G03F 7/26; G03F 7/7065; H01L 21/027; H01L 21/304; H01L 22/10
See application file for complete search history.

(56) References Cited

U.S. PATENT DOCUMENTS

| | | | |
|---|---|---|---|
| 5,886,347 A * | 3/1999 | Inoue ................... | G01N 21/274 250/339.04 |
| 2007/0010028 A1 | 1/2007 | Kondoh et al. | |
| 2013/0108958 A1 | 5/2013 | Ogihara et al. | |
| 2015/0064625 A1 | 3/2015 | Ogihara et al. | |
| 2015/0099216 A1 | 4/2015 | Iwabuchi et al. | |
| 2015/0286143 A1 * | 10/2015 | Ogihara ............ | H01L 21/31144 430/287.1 |

FOREIGN PATENT DOCUMENTS

| | | |
|---|---|---|
| CN | 1892422 | 1/2007 |
| JP | 2010169871 | 8/2010 |
| JP | 2015049395 | 3/2015 |
| JP | 2015072418 | 4/2015 |
| JP | 2015197646 | 11/2015 |
| JP | 2016073922 | 5/2016 |
| TW | 201514628 | 4/2015 |

OTHER PUBLICATIONS

"International Search Report (Form PCT/ISA/210) of PCT/JP2017/047208," dated Mar. 20, 2018, with English translation thereof, pp. 1-5.
"Written Opinion of the International Searching Authority (Form PCT/ISA/237) of PCT/JP2017/047208," dated Mar. 20, 2018, with English translation thereof, pp. 1-9.

* cited by examiner

*Primary Examiner* — Nimeshkumar D Patel
*Assistant Examiner* — Gedeon M Kidanu
(74) *Attorney, Agent, or Firm* — JCIPRNET

(57) ABSTRACT

A quality inspection method for a chemical liquid used for manufacturing a semiconductor substrate includes: a step W of preparing a first container and washing at least a portion of a liquid contact portion by using a portion of the chemical liquid, a step A of performing concentration of a portion of the chemical liquid by using the washed first container so as to obtain c liquid, a step B of performing measurement of a content of a specific component in c liquid, and a step C of comparing the content of the specific component with a preset standard value. At least the step W and the step A are performed in a clean room having cleanliness equal to or higher than class 4 specified in ISO14644-1:2015, the concentration is performed in inert gas or under reduced pressure, and the measurement is performed by a predetermined measurement method.

31 Claims, No Drawings

QUALITY INSPECTION METHOD FOR CHEMICAL LIQUID

CROSS-REFERENCE TO RELATED APPLICATIONS

This application is a Continuation of PCT International Application No. PCT/JP2017/047208 filed on Dec. 28, 2017, which claims priority under 35 U.S.C. § 119(a) to Japanese Patent Application No. 2017-001181 filed on Jan. 6, 2017 and Japanese Patent Application No. 2017-251121 filed on Dec. 27, 2017. Each of the above applications is hereby expressly incorporated by reference, in its entirety, into the present application.

BACKGROUND OF THE INVENTION

1. Field of the Invention

The present invention relates to a quality inspection method for a chemical liquid. Particularly, the present invention relates to a quality inspection method for a chemical liquid which contains an organic solvent as a main component (chemical liquid in which the content of an organic solvent with respect to the total mass of the chemical liquid is equal to or greater than 98% by mass).

2. Description of the Related Art

For manufacturing a semiconductor device, a photolithography process is used. During the photolithography process, a substrate such as a semiconductor wafer (hereinafter, referred to as "wafer" as well) is pre-wetted and then coated with an actinic ray-sensitive or radiation-sensitive resin composition (hereinafter, referred to as "resist composition" as well) so as to form an actinic ray-sensitive or radiation-sensitive film (hereinafter, referred to as "resist film" as well). Furthermore, by exposing the formed resist film, developing the exposed resist film, and rinsing the developed resist film, a resist pattern is formed on the wafer.

In recent years, as semiconductor devices have been further scaled down, the inhibition of the occurrence of a defect in the photolithography process has been required. Specifically, there has been a demand for a chemical liquid having a performance (hereinafter, referred to as "defect inhibition performance" as well) that can further inhibit the occurrence of a defect on a wafer in each of the processes such as pre-wetting, resist film formation, development, and rinsing.

In order to provide such a chemical liquid, the defect inhibition performance of the chemical liquid, in other words, the quality of the chemical liquid needs to be inspected.

JP2015-049395A describes, as the quality inspection method for a chemical liquid, a method of coating a silicon wafer with a chemical liquid (liquid to be inspected) and measuring defects on the wafer surface by using a defect inspection device manufactured by KLA-Tencor Corporation.

SUMMARY OF THE INVENTION

In order to evaluate the defect inhibition performance by using the method described in JP2015-049395A, a wafer has to be actually coated with a chemical liquid, a complicated operation which tends to cause contamination needs to be performed, and accordingly, sometimes it is difficult to accurately evaluate the defect inhibition performance of the chemical liquid. Furthermore, the inspection performed using the defect inspection device is time consuming, and it is difficult to adopt many defect inspection devices due to their high prices. As a result, unfortunately, it takes a long time to evaluate the defect inhibition performance of the chemical liquid, which makes it difficult to inspect the quality of the chemical liquid.

Therefore, an object of the present invention is to provide a quality inspection method for a chemical liquid that makes it possible to simply evaluate the defect inhibition performance of a chemical liquid.

In order to achieve the aforementioned objects, the inventors of the present invention carried out an intensive examination. As a result, the inventors have found that the object can be achieved by the following constitution.

[1] A quality inspection method for a chemical liquid used for manufacturing a semiconductor substrate, including a step W of preparing a first container having a liquid contact portion of which at least a portion is formed of at least one kind of material selected from the group consisting of glass, a fluorine-containing polymer, and electropolished stainless steel, adopting a portion of the chemical liquid as a liquid, and washing at least a portion of the liquid contact portion by using a liquid, a step A of adopting a portion of the chemical liquid as b liquid and performing concentration of b liquid by using the washed first container so as to obtain c liquid, a step B of performing measurement of a content of a specific component in c liquid, and a step C of comparing the content of the specific component with a preset standard value, in which the step W, the step A, the step B, and the step C are performed in this order, at least the step W and the step A are performed in a clean room having cleanliness equal to or higher than class 4 specified in the International Standard ISO14644-1:2015 established by the International Organization for Standardization, the concentration is performed under at least one kind of inert gas selected from the group consisting of an Ar gas, a He gas, and a $N_2$ gas or under reduced pressure, and the measurement is performed by at least one kind of measurement method selected from the group consisting of gas chromatography mass spectrometry, gas chromatography tandem mass spectrometry, gas chromatography atomic emission detection, gas chromatography quadrupole time-of-flight type mass spectrometry, direct sample introduction-type mass spectrometry, high-performance liquid chromatography mass spectrometry, high-performance liquid chromatography tandem mass spectrometry, high-performance liquid chromatography time-of-flight type mass spectrometry, inductively coupled plasma mass spectrometry, inductively coupled plasma emission spectrometry, temperature programmed desorption mass spectrometry, ion chromatography, nuclear magnetic resonance spectrometry, and atomic absorption spectrometry.

[2] The quality inspection method for a chemical liquid described in [1], further including a step D of determining the chemical liquid as being inadequate and discarding the chemical liquid in a case where the content of the specific component is greater than the standard value in the step C or a step E of purifying the chemical liquid in a case where the content of the specific component is greater than the standard value in the step C and then performing again the step W, the step A, the step B, and the step C.

[3] The quality inspection method for a chemical liquid described in [1] or [2], in which the step B is also performed in the clean room.

[4] The quality inspection method for a chemical liquid described in any one of [1] to [3], in which the step W further has at least one kind of step selected from the group consisting of a step of performing acid washing on at least the liquid contact portion of the first container, a step of performing ultrasonic washing on at least the liquid contact portion of the first container, and a step of drying at least the liquid contact portion of the first container.

[5] The quality inspection method for a chemical liquid described in any one of [1] to [4], in which a factor of concentration in the step A is 2 to 1,000,000.

[6] The quality inspection method for a chemical liquid described in any one of [1] to [5], in which a factor of concentration in the step A is 10 to 10,000.

[7] The quality inspection method for a chemical liquid described in any one of [1] to [6], in which the specific component contains at least one kind of compound selected from the group consisting of Formulae (1) to (7) which will be described later.

[8] The quality inspection method for a chemical liquid described in any one of [1] to [7], in which a temperature condition of the concentration in the step A is 10° C. to 250° C.

[9] The quality inspection method for a chemical liquid described in any one of [1] to [8], in which a volume of b liquid in the step A is equal to or smaller than 5 L.

[10] The quality inspection method for a chemical liquid described in any one of [1] to [9], in which in a case where the first container is a fluorine-containing polymer container in which at least a portion of the liquid contact portion is formed of a fluorine-containing polymer, the fluorine-containing polymer container satisfies a condition 1 or a condition 2 in the following test.

Test: a portion of the chemical liquid is adopted as d liquid, the liquid contact portion is washed using d liquid, a portion of the chemical liquid is adopted as e liquid, and under the condition that a ratio of a mass of the washed fluorine-containing polymer container to a mass of e liquid becomes 1.0 provided that a liquid temperature of e liquid is 25° C., the washed fluorine-containing polymer container is immersed for 24 hours in e liquid having a liquid temperature of 25° C.

Condition 1: in a case where e liquid having been used for the immersion contains one kind of fluoride ion, an increase of one kind of the fluoride ion before and after the immersion is equal to or smaller than 1 mass ppm.

Condition 2: in a case where e liquid having been used for the immersion contains two or more kinds of fluoride ions, a total increase of two or more kinds of the fluoride ions before and after the immersion is equal to or smaller than 1 mass ppm.

[11] The quality inspection method for a chemical liquid described in any one of [1] to [10], in which in a case where the first container is a fluorine-containing polymer container in which at least a portion of the liquid contact portion is formed of a fluorine-containing polymer, within a surface of at least a portion of the liquid contact portion, provided that an atom number ratio of the number of fluorine atoms contained in the surface to the number of carbon atoms contained in the surface is $M_1$, and an atom number ratio of the number of fluorine atoms contained in a position, which is 10 nm below the surface in a thickness direction of the fluorine-containing polymer container, to the number of carbon atoms contained in the position is $M_2$, a ratio of $M_1$ to $M_2$ is higher than 1.0.

[12] The quality inspection method for a chemical liquid described in any one of [1] to [9], in which in a case where the first container is an electropolished stainless steel container in which at least a portion of the liquid contact portion is formed of electropolished stainless steel, the electropolished stainless steel container satisfies a condition 3 or a condition 4 in the following test.

Test: a portion of the chemical liquid is adopted as f liquid, the liquid contact portion is washed using f liquid, a portion of the chemical liquid is adopted as g liquid, and under the condition that a ratio of a mass of the washed electropolished stainless steel container to a mass of g liquid becomes 0.25 provided that a liquid temperature of g liquid is 25° C., the washed electropolished stainless steel container is immersed for 24 hours in g liquid having a liquid temperature of 25° C.

Condition 3: in a case where g liquid having been used for the immersion contains one kind of metal component, an increase of one kind of the metal component before and after the immersion is equal to or smaller than 1 mass ppm.

Condition 4: in a case where g liquid having been used for the immersion contains two or more kinds of metal components, a total increase of two or more kinds of the metal components before and after the immersion is equal to or smaller than 1 mass ppm.

[13] The quality inspection method for a chemical liquid described in any one of [1] to [9] and [12], in which in a case where the first container is an electropolished stainless steel container in which at least a portion of the liquid contact portion is formed of electropolished stainless steel, within a surface of at least a portion of the liquid contact portion, provided that an atom number ratio of the number of chromium atoms contained in the surface to the number of iron atoms contained in the surface is $P_1$, and an atom number ratio of the number of chromium atoms contained in a position, which is 10 nm below the surface in a thickness direction of the electropolished stainless steel container, to the number of iron atoms contained in the position is $P_2$, a ratio of $P_1$ to $P_2$ is higher than 1.0.

[14] The quality inspection method for a chemical liquid described in any one of [1] to [9], [12], and [13], in which in a case where the first container is an electropolished stainless steel container in which at least a portion of the liquid contact portion is formed of electropolished stainless steel, within a surface of at least a portion of the liquid contact portion, an atom number ratio of the number of chromium atoms contained in a position, which is 1 nm below the surface in a thickness direction of the electropolished stainless steel container, to the number of iron atoms contained in the position is equal to or higher than 1.0.

[15] The quality inspection method for a chemical liquid described in any one of [1] to [14], in which the chemical liquid contains at least one kind of organic solvent selected from the group consisting of propylene glycol monomethyl ether, propylene glycol monoethyl ether, propylene glycol monopropyl ether, propylene glycol monomethyl ether acetate, ethyl lactate, methoxymethyl propionate, cyclopentanone, cyclohexanone, γ-butyrolactone, diisoamyl ether, butyl acetate, isoamyl acetate, isopropanol, and 4-methyl-2-pentanol.

[16] The quality inspection method for a chemical liquid described in any one of [1] to [15], in which the measurement includes organic analysis for measuring a content of an organic component in c liquid and inorganic analysis for measuring a content of an inorganic component in c liquid.

[17] The quality inspection method for a chemical liquid described in any one of [1] to [16], in which the measurement is performed by at least one kind of measurement method selected from the group consisting of gas chromatography mass spectrometry, gas chromatography tandem mass spectrometry, high-performance liquid chromatography mass spectrometry, high-performance liquid chromatography tandem mass spectrometry, and inductively coupled plasma mass spectrometry.

[18] The quality inspection method for a chemical liquid described in any one of [1] to [17], in which the measurement is performed by at least one kind of measurement method selected from the group consisting of high-performance liquid chromatography mass spectrometry and high-performance liquid chromatography tandem mass spectrometry.

[19] The quality inspection method for a chemical liquid described in any one of [1] to [18], in which each of the content of the specific component measured in the step B and the standard value compared in the step C is an absolute quantity.

[20] The quality inspection method for a chemical liquid described in any one of [1] to [19], in which each of the content of the specific component measured in the step B and the standard value compared in the step C is a relative quantity.

[21] The quality inspection method for a chemical liquid described in any one of [1] to [20], in which the specific component contains an organic substance having a boiling point equal to or higher than 200° C.

[22] The quality inspection method for a chemical liquid described in [21], in which the specific component contains an organic substance having a boiling point of 300° C. to 800° C.

[23] The quality inspection method for a chemical liquid described in any one of [1] to [22], in which the specific component contains an organic substance having a molecular weight equal to or greater than 200.

[24] The quality inspection method for a chemical liquid described in [23], in which the specific component contains an organic substance having a molecular weight of 300 to 1,000.

[25] The quality inspection method for a chemical liquid described in any one of [1] to [24], in which the measurement is performed by at least one kind of measurement method selected from the group consisting of gas chromatography mass spectrometry, gas chromatography tandem mass spectrometry, high-performance liquid chromatography mass spectrometry, and high-performance liquid chromatography tandem mass spectrometry, and the specific component contains an organic substance in which m/Z is 300 to 1,000.

[26] The quality inspection method for a chemical liquid described in any one of [1] to [25], further comprising a specific component determination step that is performed before the step W or between the step W and the step A, in which the specific component determination step includes a step W3 of preparing a third container having a liquid contact portion of which at least a portion is formed of at least one kind of material selected from the group consisting of glass, a fluorine-containing polymer, and electropolished stainless steel, adopting a portion of the chemical liquid as h liquid, and washing at least a portion of the liquid contact portion of the third container by using h liquid, a step A3 of adopting a portion of the chemical liquid as i liquid and concentrating i liquid by using the washed third container so as to obtain three or more kinds of j liquids having different factors of concentration, a step B3 of performing measurement of a content of an organic substance, in which m/Z is 300 to 1,000, in j liquids by at least one kind of measurement method selected from the group consisting of high-performance liquid chromatography mass spectrometry and gas chromatography mass spectrometry, and a step C3 in which in a case where one kind of organic substance is commonly detected from all of three or more kinds of j liquids, one kind of the organic substance is determined as a specific component, and in a case where two or more kinds of organic substances are commonly detected from all of three or more kinds of j liquids, from a coefficient of correlation obtained by performing linear regression on the factors of concentration and the content of each of two or more kinds of the organic substances and a coefficient of correlation obtained by performing linear regression on the factors of concentration and the total content of organic substances in a combination of two or more kinds of the organic substances, a maximum coefficient of correlation is selected, and an organic substance or a combination of organic substances from which the maximum coefficient of correlation is obtained is determined as a specific component, the step W3, the step A3, the step B3, and the step C3 are performed in this order, at least the step W3 and the step A3 are performed in a clean room having cleanliness equal to or higher than class 4 specified in the International Standard ISO14644-1:2015 established by the International Organization for Standardization, and the concentration of i liquid is performed under at least one kind of inert gas selected from the group consisting of an Ar gas, a He gas, and a $N_2$ gas or under reduced pressure.

[27] The quality inspection method for a chemical liquid described in [26], further including a standard value determination step of determining the standard value at a point in time when the specific component determination step has finished but the step C is not yet started, in which the standard value determination step includes a step W4 of preparing n pieces of fourth containers each having a liquid contact portion of which at least a portion is formed of at least one kind of material selected from the group consisting of glass, a fluorine-containing polymer, and electropolished stainless steel, preparing n kinds of chemical liquids manufactured by different manufacturing methods, obtaining twice a portion of each of n kinds of the chemical liquids, naming the obtained chemical liquids as $p_1$ liquid and $p_2$ liquid respectively, and washing at least a portion of the liquid contact portion of each of the fourth containers by using each of $p_1$ liquids, a step A4 of performing concentration of each of the corresponding liquids $p_2$ by using each of the fourth containers washed with each of the liquids $p_1$ so as to obtain n kinds of liquids q, a step B4 of performing measurement of a content of a specific component in each of q liquids by at least one kind of measurement method selected from the group consisting of high-performance liquid chromatography mass spectrometry and gas chromatography mass spectrometry, a step S of evaluating a defect inhibition performance of each of n kinds of the chemical liquids by using a defect inspection device, a step T of creating a calibration curve by performing linear regression on the content of the specific component and the defect inhibition performance, and a step U of determining the content of the specific component corresponding to a predetermined defect inhibition performance as a standard value by using the calibration curve, the step W4, the step A4, the step B4, the step S, the step T, and the step U are performed in this order, at least the step W4 and the step A4 are performed in a clean room having cleanliness equal to or higher than class 4 specified in the International Standard ISO14644-1:2015 established by the International Organization for Standardization, the concentration of $p_2$ liquid is performed under at least one kind of inert gas selected from the group consisting of an Ar gas, a He gas, and a $N_2$ gas or under reduced pressure, and n represents an integer equal to or greater than 3.

[28] The quality inspection method for a chemical liquid described in any one of [1] to [27], in which the measurement includes inorganic analysis for analyzing a content of an inorganic component in c liquid, and provided that the content of the specific component measured in the step B is an absolute quantity, the absolute quantity is determined by a standard addition method.

[29] The quality inspection method for a chemical liquid described in any one of [1] to [28], in which the measurement includes inorganic analysis for measuring a content of an inorganic substance in c liquid, and the inorganic analysis is measurement of a content of at least 5 or more kinds of atoms selected from the group consisting of Ag, Al, As, Au, Ba, Ca, Cd, Co, Cr, Cu, Fe, Ga, Ge, K, Li, Mg, Mn, Mo, Na, Nb, Ni, Pb, Sb, Sn, Sr, Ta, Th, Ti, Tl, V, W, Zn, and Zr in c liquid.

[30] The quality inspection method for a chemical liquid described in [29], in which 5 or more kinds of the atoms contain at least two or more kinds of atoms selected from the group consisting of Al, Fe, and Ti.

[31] The quality inspection method for a chemical liquid described in any one of [1] to [30], in which in a case where the content of the specific component is equal to or smaller than the standard value in the step C, the chemical liquid is determined as being adequate.

According to the present invention, a quality inspection method for a chemical liquid can be provided which makes it possible to simply evaluate the defect inhibition performance of a chemical liquid.

DESCRIPTION OF THE PREFERRED EMBODIMENTS

Hereinafter, the present invention will be specifically described.

The following constituents will be described based on typical embodiments of the present invention in some cases, but the present invention is not limited to the embodiments.

In the present specification, a range of numerical values described using "to" means a range including the numerical values listed before and after "to" as a lower limit and an upper limit respectively.

In the present invention, "preparation" means not only the preparation of a specific material by means of synthesis or mixing but also the preparation of a predetermined substance by means of purchase and the like.

In the present invention, "ppm" means "parts-per-million $(10^{-6})$", "ppb" means "parts-per-billion $(10^{-9})$", "ppt" means "parts-per-trillion $(10^{-12})$", and "ppq" means "parts-per-quadrillion $(10^{-15})$".

In the present invention, 1 Å (angstrom) equals 0.1 nm.

In the present invention, "polymer" means a compound having a weight-average molecular weight equal to or greater than 2,000.

[Quality Inspection Method for a Chemical Liquid for Chemical Liquid]

The quality inspection method for a chemical liquid according to an embodiment of the present invention is a quality inspection method for a chemical liquid used for manufacturing a semiconductor substrate and includes a step W of preparing a first container having a liquid contact portion of which at least a portion is formed of at least one kind of material (hereinafter, referred to as "corrosion-resistance material" as well) selected from the group consisting of glass, a fluorine-containing polymer, and electropolished stainless steel, adopting a portion of the chemical liquid as a liquid, and washing at least a portion of the liquid contact portion by using a liquid, a step A of adopting a portion of the chemical liquid as b liquid and performing concentration of b liquid by using the washed first container so as to obtain c liquid, a step B of performing measurement of a content of a specific component in c liquid, and a step C of comparing the content of the specific component with a preset standard value, in which the step W, the step A, the step B, and the step C are performed in this order, at least the step W and the step A are performed in a clean room having cleanliness equal to or higher than class 4 specified in the International Standard ISO14644-1:2015 established by the International Organization for Standardization, the concentration is performed under at least one kind of inert gas selected from the group consisting of an Ar gas, a He gas, and a $N_2$ gas or under reduced pressure, and the measurement is performed by at least one kind of measurement method selected from the group consisting of gas chromatography mass spectrometry, gas chromatography tandem mass spectrometry, gas chromatography atomic emission detection, gas chromatography quadrupole time-of-flight type mass spectrometry, direct sample introduction-type mass spectrometry, high-performance liquid chromatography mass spectrometry, high-performance liquid chromatography tandem mass spectrometry, high-performance liquid chromatography time-of-flight type mass spectrometry, inductively coupled plasma mass spectrometry, inductively coupled plasma emission spectrometry, temperature programmed desorption mass spectrometry, ion chromatography, nuclear magnetic resonance spectrometry, and atomic absorption spectrometry.

[Step W]

The step W is a step of preparing a first container having a liquid contact portion formed of a corrosion-resistance material, adopting a portion of the chemical liquid as a liquid, and washing at least a portion of the liquid contact portion by using a liquid. Hereinafter, the members and the methods used in the step W will be specifically described.

<Chemical Liquid>

The chemical liquid is used for manufacturing a semiconductor substrate. Examples of components in the chemical liquid include a solvent and a specific component.

(Solvent)

The chemical liquid contains a solvent. Examples of the solvent include water, an organic solvent, and a mixture of these. It is preferable that the chemical liquid contains the organic solvent among the above. In the present specification, "organic solvent" means an organic substance which stays in liquid form under the atmospheric pressure at 25° C. and is contained in the chemical liquid in an amount equal to or greater than 10,000 mass ppm with respect to the total mass of the chemical liquid.

The content of the solvent in the chemical liquid is not particularly limited. Generally, the content of the solvent with respect to the total mass of the chemical liquid is preferably equal to or greater than 98% by mass, more preferably equal to or greater than 99% by mass, even more preferably equal to or greater than 99.9% by mass, particularly preferably equal to or greater than 99.99% by mass, and most preferably equal to or greater than 99.999% by mass.

One kind of solvent may be used singly, or two or more kinds of solvents may be used in combination. In a case where two or more kinds of solvents are used in combination, the total content thereof is preferably within the above range.

Organic Solvent

The organic solvent that the chemical liquid contains is not particularly limited, and examples thereof include alkylene glycol monoalkyl ether carboxylate, alkylene glycol monoalkyl ether, a lactic acid alkyl ester, alkoxyalkyl propionate, cyclic lactone (preferably having 4 to 10 carbon atoms), a monoketone compound which may have a ring (preferably having 4 to 10 carbon atoms), alkylene carbonate, alkoxyalkyl acetate, alkyl pyruvate, and the like.

Furthermore, as the organic solvent, those described in JP2016-057614A, JP2014-219664A, JP2016-138219A, and JP2015-135379A may be used.

The organic solvent may be methanol, ethanol, 1-propanol, isopropanol, n-propanol, 2-methyl-1-propanol, n-butanol, 2-butanol, tert-butanol, 1-pentanol, 2-pentanol, 3-pentanol, n-hexanol, cyclohexanol, 2-methyl-2-butanol, 3-methyl-2-butanol, 2-methyl-1-butanol, 3-methyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 2-ethyl-1-butanol, 2,2-dimethyl-3-pentanol, 2,3-dimethyl-3-pentanol, 2,4-dimethyl-3-pentanol, 4,4-dimethyl-2-pentanol, 3-ethyl-3-pentanol, 1-heptanol, 2-heptanol, 3-heptanol, 2-methyl-2-hexanol, 2-methyl-3-hexanol, 5-methyl-1-hexanol, 5-methyl-2-hexanol, 2-ethyl-1-hexanol, methyl cyclohexanol, trimethyl cyclohexanol, 4-methyl-3-heptanol, 6-methyl-2-heptanol, 1-octanol, 2-octanol, 3-octanol, 2-propyl-1-pentanol, 2,6-dimethyl-4-heptanol, 2-nonanol, 3,7-dimethyl-3-octanol, ethylene glycol, propylene glycol, diethyl ether, dipropyl ether, diisopropyl ether, butyl methyl ether, butyl ethyl ether, butyl propyl ether, dibutyl ether, diisobutyl ether, tert-butyl methyl ether, tert-butyl ethyl ether, tert-butyl propyl ether, di-tert-butyl ether, dipentyl ether, diisoamyl ether, cyclopentyl methyl ether, cyclohexyl methyl ether, bromomethyl methyl ether, α,α-dichloromethyl methyl ether, chloromethyl ethyl ether, 2-chloroethyl methyl ether, 2-bromoethyl methyl ether, 2,2-dichloroethyl methyl ether, 2-chloroethyl ethyl ether, 2-bromoethyl ethyl ether, (±)-1,2-dichloroethyl ethyl ether, 2,2,2-trifluoroethyl ether, ethyl vinyl ether, butyl vinyl ether, allyl ethyl ether, allyl propyl ether, allyl butyl ether, diallyl ether, 2-methoxypropene, ethyl-1-propenylether, cis-1-bromo-2-ethoxyethylene, 2-chloroethyl vinyl ether, allyl-1,1,2,2-tetrafluoroethyl ether, octane, isooctane, nonane, decane, methyl cyclohexane, decalin, xylene, ethyl benzene, diethyl benzene, cumene, sec-butyl benzene, cymene, dipentene, methyl pyruvate, propylene glycol monomethyl ether, propylene glycol monoethyl ether, propylene glycol monopropyl ether, propylene glycol monomethyl ether acetate, ethyl lactate, methyl methoxypropionate, cyclopentanone, cyclohexanone, butyl acetate, isoamyl acetate, chloroform, dichloromethane, 1,4-dioxane, tetrahydrofuran, or the like.

In an aspect in which the chemical liquid is used for manufacturing a semiconductor substrate and is incorporated particularly into a prewet solution, a developer, and a resist composition, the chemical liquid preferably contains at least one kind of organic solvent selected from the group consisting of propylene glycol monomethyl ether (PGME), cyclopentanone (CyPn), cyclopentane (CyPe), butyl acetate (nBA), propylene glycol monomethyl ether acetate (PGMEA), cyclohexane (CyHe), cyclohexanone (CyHx), ethyl lactate (EL), 2-hydroxymethyl isobutyrate (HBM), cyclopentanone dimethyl acetal (DBCPN), γ-butyrolactone (GBL), dimethyl sulfoxide (DMSO), ethylene carbonate (EC), propylene carbonate (PC), 1-methyl-2-pyrrolidone (NMP), isoamyl acetate (iAA), 2-propanol (IPA), methyl ethyl ketone (MEK), and 4-methyl-2-pentanol (MIBC), and more preferably contains at least one kind of organic solvent selected from the group consisting of PGMEA, MIBC, nBA, PGME, CyHe, GBL, EL, DMSO, iAA, HBM, PC, IPA, and CyPe. One kind of organic solvent may be used singly, or two or more kinds of organic solvents may be used in combination.

The content of the organic solvent in the chemical liquid is not particularly limited. Generally, the content of the organic solvent with respect to the total mass of the chemical liquid is preferably equal to or greater than 98% by mass, more preferably equal to or greater than 99% by mass, even more preferably equal to or greater than 99.9% by mass, particularly preferably equal to or greater than 99.99% by mass, and most preferably equal to or greater than 99.999% by mass.

One kind of organic solvent may be used singly, or two or more kinds of organic solvents may be used in combination. In a case where two or more kinds of organic solvents are used in combination, the total content thereof is preferably within the above range.

(Specific Component)

The specific component means a component or a combination of components that is contained in the chemical liquid and causes a defect. Examples of the specific component include an inorganic substance (hereinafter, referred to as "specific inorganic substance" as well) and an organic substance (hereinafter, referred to as "specific organic substance" as well).

In the present specification, the specific organic substance means an organic substance contained in the chemical liquid in an amount equal to or smaller than 10,000 mass ppm with respect to the total mass of the chemical liquid.

Specific Organic Substance

The organic substance as the specific component is not particularly limited, and examples thereof include known organic substances. The content of the specific organic substance in the chemical liquid is not particularly limited, but is preferably equal to or smaller than 1 mass ppb, more preferably equal to or smaller than 100 mass ppt, and even more preferably equal to or smaller than 10 mass ppt.

Examples of the specific organic substance include a high-boiling-point organic substance having a boiling point higher than that of the aforementioned solvent. Specifically, examples thereof include organic substances having a boiling point equal to or higher than 200° C. Particularly, in a case where the content of an organic substance having a boiling point of 300° C. to 800° C. and the defect inhibition performance of the chemical liquid are subjected to linear regression, a higher coefficient of correlation is obtained.

The molecular weight of the specific organic substance is not particularly limited. In a case where a compound having a molecular weight equal to or greater than 200 and the defect inhibition performance of the chemical liquid are subjected to linear regression, a higher coefficient of correlation is obtained. From a compound having a molecular weight of 300 to 1,000, a much higher coefficient of correlation is obtained.

In a case where the measurement in the step B, which will be described later, is performed by at least one kind of measurement method selected from the group consisting of gas chromatography mass spectrometry, gas chromatography tandem mass spectrometry, high-performance liquid chromatography mass spectrometry, and high-performance liquid chromatography tandem mass spectrometry, and the specific organic substance as an organic substance, in which m/Z is 300 to 1,000, and the defect inhibition performance of the chemical liquid are subjected to linear regression, a higher coefficient of correlation is obtained.

Some of such specific organic substances are mixed into the chemical liquid by being eluted from unreacted raw materials used at the time of synthesizing the organic solvent, a structural isomer of an organic solvent, a stabilizer for preventing the oxidation of the organic solvent (for example, dibutylhydroxytoluene (BHT, boiling point: 265° C.) or the like), and members of the manufacturing device or the like.

Examples of the organic substance that is eluted from the members of the manufacturing device or the like in some cases include a resin component, a plasticizer, or the like contained in a plastic material (for example, an O-ring or the like). Examples of such a component include dioctyl phthalate (DOP, boiling point: 385° C.), diisononyl phthalate (DINP, boiling point: 403° C.), dioctyl adipate (DOA, boiling point: 335° C.), dibutyl phthalate (DBP, boiling point: 340° C.), ethylene propylene rubber (EPDM, boiling point: 300° C. to 450° C.), and the like.

Examples of the specific organic substance include, in addition to the above, bis(2-ethylhexyl)phthalate (DEHP), bis(2-propylheptyl) phthalate (DPHP), dibutyl phthalate (DBP), benzyl butyl phthalate (BBzP), diisodecyl phthalate (DIDP), diisooctyl phthalate (DIOP), diethyl phthalate (DEP), diisobutyl phthalate (DIBP), dihexyl phthalate, diisononyl phthalate, trimethyl trimellitate (TMTM), tris(2-ethylhexyl) trimellitate (TEHTM), tris(n-octyl-n-decyl) trimellitate (ATM), tris(heptyl,nonyl) trimellitate (LTM), tris(octyl) trimellitate (OTM), bis(2-ethylhexyl) adipate (DEHA), dimethyl adipate (DMAD), monomethyl adipate (MMAD), dioctyl adipate (DOA), diisononyl adipate (DINA), dibutyl sebacate (DBS), dibutyl maleate (DBM), diisobutyl maleate (DIBM), an azelaic acid ester, a benzoic acid ester, terephthalate (example: dioctyl terephthalate (DEHT)), a 1,2-cyclohexanedicarboxylic acid diisononyl ester (DINCH), epoxidized vegetable oil, an alkylsulfonic acid phenyl ester (ASE), sulfonamide (example: N-ethyltoluene sulfonamide (ETSA), N-(2-hydroxypropyl)benzene sulfonamide (HP BSA), and N-(n-butyl)benzene sulfonamide (BBSA-NBBS)), an organic phosphoric acid ester (example: tricresyl phosphate (TCP), and tributyl phosphate (TBP)), triethylene glycol dihexanoate (3G6), tetraethylene glycol diheptanoate (4G7), acetylated monoglyceride, triethyl citrate (TEC), acetyl triethyl citrate (ATEC), tributyl citrate (TBC), acetyl tributyl citrate (ATBC), trioctyl citrate (TOC), acetyl trioctyl citrate (ATOC), trihexyl citrate (THC), acetyl trihexyl citrate (ATHC), butyl trihexyl citrate (BTHC), trimethyl citrate (TMC), epoxidized soybean oil, nitroglycerine (NG), butanetriol trinitrate (BTTN), dinitrotoluene (DNT), trimethylolethane trinitrate (TMETN), diethylene glycol dinitrate (DEGDN), triethylene glycol dinitrate (TEGDN), bis(2,2-dinitropropyl)formal (BDNPF), bis(2,2-dinitropropyl)acetal (BDNPA), 2,2,2-trinitroethyl-2-introethyl ether (TNEN), polybutene, and the like.

The inventors of the present invention have found that in a case where the chemical liquid contains specific organic substances represented by Formulae (1) to (7) among the above, and the content thereof and the defect inhibition performance of the chemical liquid are subjected to linear regression, a much higher coefficient of correlation is obtained. In the present quality inspection method, in a case where the specific compound contains the organic substances represented by Formulae (1) to (7), the defect inhibition performance of the chemical liquid can be more accurately evaluated.

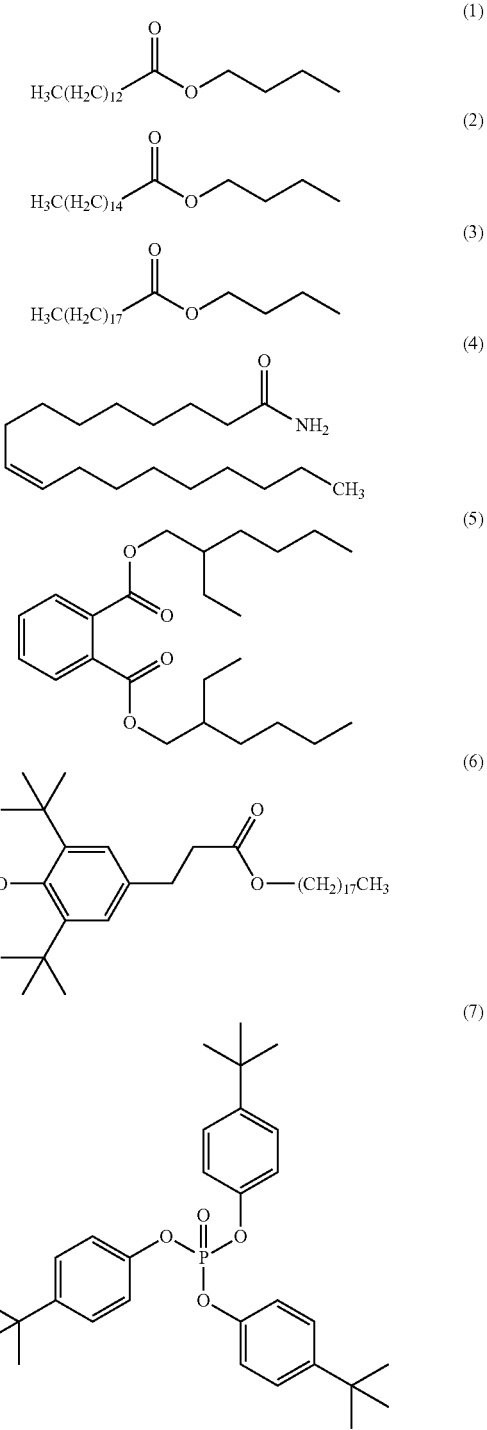

Specific Inorganic Substance

The inorganic substance ("specific inorganic substance") as the specific component is not particularly limited, and examples thereof include known metals, inorganic compounds, and the like. The content of the specific inorganic substance in the chemical liquid is not particularly limited, but is preferably equal to or smaller than 1 mass ppb, more preferably equal to or smaller than 100 mass ppt, and even more preferably equal to or smaller than 10 mass ppt, with respect to the total mass of the chemical liquid.

In some cases, the specific inorganic substance is mixed into the chemical liquid from, for example, a metal tank of a manufacturing device used for manufacturing the chemical liquid, a filter used for purifying the chemical liquid, and the like.

Examples of the specific inorganic substance include Ag, Al, As, Au, Ba, Ca, Cd, Co, Cr, Cu, Fe, Ga, Ge, K, Li, Mg, Mn, Mo, Na, Nb, Ni, Pb, Sb, Sn, Sr, Ta, Th, Ti, Tl, V, W, Zn, Zr, and the like. According to the examination conducted by the inventors of the present invention, it has been revealed that in a case where the chemical liquid contains at least 5 or more kinds of atoms selected from the group consisting of Ag, Al, As, Au, Ba, Ca, Cd, Co, Cr, Cu, Fe, Ga, Ge, K, Li, Mg, Mn, Mo, Na, Nb, Ni, Pb, Sb, Sn, Sr, Ta, Th, Ti, Tl, V, W, Zn, and Zr among the above, and the total content thereof and the defect inhibition performance of the chemical liquid are subjected to linear regression, a higher coefficient of correlation is obtained. Furthermore, it has been revealed that in a case where 5 or more kinds of the atoms contain at least 2 or more kinds of metals selected from the group consisting of Al, Fe, and Ti, and the total content thereof and the defect inhibition performance of the chemical liquid are subjected to linear regression, a much higher coefficient of correlation is obtained.

<First Container>

As the first container prepared in the step W, known containers can be used without particular limitation as long as at least a portion of the liquid contact portion thereof is formed of a corrosion-resistance material.

The shape of the container is not particularly limited. For example, the container may have the shape of a bottle with a lid. That is, the container may have the shape of a container having an opening at one end and a lid portion, which is attachably and detachably mounted on one end of the container so as to seal the opening, and a liquid is stored in a cavity formed by the container and the lid mounted on the container. The container may also have a shape (for example, an eggplant-shaped flask or the like) which enables the container to be connected to a device (rotary evaporator or the like) used in a concentration step which will be described later.

The volume of the first container is not particularly limited, and can be appropriately selected according to the use.

The thickness of the first container is not particularly limited and may be appropriately selected according to the used material, such that the container retains the concentrated chemical liquid and can stand upright on its own while maintaining the shape thereof as necessary. Generally, the thickness of the first container is preferably about 1 to 30 mm.

In the present specification, "preparing" means preparing the container by manufacturing, purchasing, and the like.

At least a portion of the liquid contact portion of the first container is formed of a corrosion-resistance material. In the present specification, the liquid contact portion means a portion which is likely to contact a liquid (for example, a chemical liquid) stored in the first container. Examples of the liquid contact portion include inner wall, inner bottom, and the like.

In the first container, at least a portion of the liquid contact portion may be formed of a corrosion-resistance material. However, in view of obtaining further improved effects of the present invention, it is preferable that at least 50% or more of the liquid contact portion based on the area is formed of the corrosion-resistance material. The proportion of the area of the liquid contact portion formed of the corrosion-resistance material is more preferably equal to or higher than 70%, even more preferably equal to or higher than 80%, particularly preferably equal to or higher than 90%, and most preferably equal to or higher than 99%.

In the first container, it is preferable that portions other than the liquid contact portion are formed of the corrosion-resistance material. Examples of the portions other than the liquid contact portion include inner wall, bottom, and the like.

The aspect in which the liquid contact portion of the first container is formed of the corrosion-resistance material is not particularly limited. Examples thereof include an aspect in which at least a portion of the first container (preferably 80% or more of the first container, more preferably 90% or more of the first container, and even more preferably the entirety of the first container) is formed of the corrosion-resistance material, and an aspect in which at least a portion of the container (preferably 80% or more of the container, more preferably 90% or more of the container, and even more preferably the entirety of the container) is formed of a laminate including a base material and a coating layer, which is formed of the corrosion-resistance material and disposed on the base material so as to cover at least a portion of the base material, and the coating layer forms a liquid contact portion.

(Corrosion-Resistance Material)

The corrosion-resistance material is at least one kind of material selected from the group consisting of glass, a fluorine-containing polymer, and electropolished stainless steel. These may be used in combination. From the container having a liquid contact portion formed of the above material, an impurity is hardly eluted into the liquid (for example, the chemical liquid) stored in the interior of the container.

Glass

The glass is not particularly limited, and examples thereof include soda lime glass, borosilicate glass, and the like. Furthermore, the glass may be surface-treated glass having undergone a surface treatment. In other words, the glass may be glass with a coating layer having a glass base material and a coating layer which is disposed on the glass base material so as to cover the glass base material.

The surface treatment method is not particularly limited, and for example, the methods described in JP1984-035043A (JP-S59-035043A), JP1999-029148A (JP-H11-029148A), and the like can be referred to.

Fluorine-Containing Polymer

As the fluorine-containing polymer, known polymers containing fluorine atoms can be used without particular limitation. The fluorine-containing polymer is not particularly limited, and may have a unit represented by Formula (1) (referred to as "unit 1" as well) and optionally further has a unit represented by Formula (2) (referred to as "unit 2" as well).

In Formula (1), $R_1$ to $R_4$ each independently represent a hydrogen atom, a fluorine atom, a chlorine atom, or a perfluoroalkyl group, $R_1$ to $R_4$ may be the same as or different from each other, and at least one of $R_1$ to $R_4$ represents a fluorine atom or a perfluoroalkyl group.

Particularly, in view of obtaining further improved effects of the present invention, it is preferable that $R_1$ to $R_4$ each independently represent a fluorine atom or a perfluoroalkyl group.

In addition, in view of obtaining further improved effects of the present invention, it is preferable that the fluorine-containing polymer includes the unit represented by Formula (1). In this case, the fluorine-containing polymer may contain only one kind of unit represented by Formula (1) (for example, polytetrafluoroethylene or the like) or contain two or more kinds of units represented by Formula (1) (for example, perfluoroalkoxyalkane, a tetrafluoroethylene•hexafluoropropylene copolymer, or the like).

The content (mol %) of the unit 1 and the unit 2 in the fluorine-containing polymer is not particularly limited, and may be appropriately selected according to the use.

As the fluorine-containing polymer, at least one kind of polymer selected from the group consisting of polytetrafluoroethylene (PTFE), perfluoroalkoxyalkane (PFA), a tetrafluoroethylene•hexafluoropropylene copolymer (perfluoroethylene propene copolymer, FEP), an ethylene•tetrafluoroethylene copolymer (ethylene tetrafluoroethylene copolymer, ETFE), an ethylene•chlorotrifluoroethylene copolymer (ECTFE), polychlorotrifluoroethylene (PCTFE), polyvinylidene fluoride (PVDF), and polyvinyl fluoride (PVF) is preferable. In view of obtaining a member having further improved effects of the present invention, a fully fluorinated fluorine-containing polymer is preferable, PTFE, PFA, or FEP is more preferable, and terminal-stabilized PFA or PTFE which will be described later is even more preferable.

Generally, in the fluorine-containing polymer, either or both of a polymerizable group and a group such as —CH$_2$OH or —COOH derived from a molecular weight adjuster remain on the terminal of a polymer chain in many cases. These groups are unstable and generate —COF by being thermally decomposed at the time of molding. Furthermore, the inventors of the present invention have found that the —COF undergoes hydrolysis and causes a fluoride ion (preferably having a molecular weight equal to or smaller than 1,000) such as an ion of a fluorinated substance to be eluted into the chemical liquid.

As the fluorine-containing polymer, a fluorine-containing polymer having a perfluoroalkyl group on a terminal is preferable. In other words, the fluorine-containing polymer is preferably a treated fluorine-containing polymer in which the polymer chain terminal has been subjected to a substitution treatment (terminal stabilization) by using a perfluoroalkyl group. The perfluoroalkyl group is not particularly limited, and is preferably —CF$_2$—CF$_3$ or —CF$_3$.

As the substitution treatment method, known methods can be used without particular limitation. For example, it is possible to adopt known methods described in JP1985-240713A (JP-S60-240713A), JP1987-104822A (JP-S62-104822A), JP1991-250008A (JP-1103-250008A), and the like.

In the treated fluorine-containing polymer, the total content (total number) of —CH$_2$OH, —COOH, and —COF per $10^6$ carbon atoms in the treated fluorine-containing polymer is preferably equal to or smaller than 50, and more preferably equal to or smaller than 30.

Physical Property 1 of Fluorine-Containing Polymer Container (Amount of Fluoride Ion Eluted)

In a case where the first container is a fluorine-containing polymer container in which at least a portion of the liquid contact portion is formed of a fluorine-containing polymer, it is preferable that the fluorine-containing polymer container satisfies a condition 1 or a condition 2 in the following test. In a case where the fluorine-containing polymer container satisfies the following condition 1 or condition 2, further improved effects of the present invention are obtained.

The test method is as below. A portion of the chemical liquid is adopted as d liquid, and by using d liquid, the liquid contact portion is washed. Furthermore, a portion of the chemical liquid is adopted as e liquid, and under the condition that a ratio of a mass of the washed fluorine-containing polymer container to a mass of e liquid becomes 1.0 provided that a liquid temperature of e liquid is 25° C., the washed fluorine-containing polymer container is immersed for 24 hours in e liquid having a liquid temperature of 25° C. That is, the test method is a method of immersing the first container, which is used for concentrating the chemical liquid, in the chemical liquid which is a target of quality inspection. At this time, provided that the fluorine-containing polymer container weighs 200 g, the amount of e liquid used for immersion is set such that e liquid weighs 200 g in a case where the liquid temperature of e liquid is set to be 25° C. The liquid temperature of e liquid is adjusted such that the liquid temperature is kept at 25° C. while the container is being immersed (for 24 hours) in the liquid.

It is preferable that the immersion may be performed in a clean room which will be described later, because then the influence of the intermixing of an impurity into e liquid from the environment (contamination) can be further inhibited.

The immersion tank used for the immersion is not particularly limited. It is preferable that the immersion tank is formed of the aforementioned corrosion-resistance material. Alternatively, it is preferable that a liquid contact portion of the tank is washed with d liquid before use.

Then, an increase in the content of fluoride ions in e liquid before and after the immersion is measured. The content of fluoride ions in e liquid before the immersion and the content of fluoride ions in e liquid after the immersion are measured, and a difference therebetween is adopted as the increase. The content of fluoride ions in the immersion liquid is measured by ion chromatography. Specifically, the content of fluoride ions is measured using the following device under the following conditions or measured using a device under conditions corresponding to the following ones.

Device: HIC-SP suppressor ion chromatograph manufactured by Shimadzu Corporation Used column: ion exchange resin (inner diameter: 4.0 mm, length: 25 cm) Mobile phase: sodium hydrogen carbonate solution (1.7 mmol/L)-sodium carbonate solution (1.8 mmol/L)

Flow rate: 1.5 mL/min

Amount of sample injected: 25 μL

Column temperature: 40° C.

Suppressor: electrodialysis type detector: electric conductivity detector (30° C.)

For the first container, it is preferable that the increase in fluoride ions (in other words, the amount of fluoride ions eluted) measured by the above method satisfies any of the following conditions.

Condition 1: in a case where e liquid having been used for the immersion contains one kind of fluoride ion, the increase in one kind of the fluoride ion before and after the immersion is equal to or smaller than 1 mass ppm.

Condition 2: in a case where e liquid having been used for the immersion contains two or more kinds of fluoride ions, the total increase in two or more kinds of the fluoride ions before and after the immersion is equal to or smaller than 1 mass ppm.

It is preferable that the first container, in which at least a portion of the liquid contact portion is formed of glass or electropolished stainless steel, also satisfies the above condition.

Physical property 1 of fluorine-containing polymer container (contribution of F/C ratio)

Regarding the fluorine-containing polymer container, within a surface of at least a portion of the liquid contact portion, provided that an atom number ratio of the number of fluorine atoms contained in the surface to the number of carbon atoms contained in the surface is $M_1$, and an atom number ratio of the number of fluorine atoms contained in a position, which is 10 nm below the surface in a thickness direction of the container, to the number of carbon atoms contained in the position is $M_2$, it is preferable that a ratio of $M_1$ to $M_2$ ($M_1/M_2$) is higher than 1.0.

The upper limit of $M_1/M_2$ is not particularly limited, but is preferably equal to or lower than 3.0.

The state where $M_1/M_2$ is higher than 1.0 means that an atom number-based abundance ratio of fluorine atoms to carbon atoms (F/C) is higher in the uppermost surface of the first container than in the interior of the first container. In this case, the chemical resistance of the surface of the first container is improved, and consequently, further improved effects of the present invention are obtained.

In a case where $M_1/M_2$ is equal to or lower than 3.0, free fluoride ions within the uppermost surface of the liquid contact portion (in other words, fluoride ions that are not bonded to the fluorine-containing polymer) are further reduced, and it becomes harder for the fluoride ions to be eluted into the concentrated chemical liquid. As a result, further improved effects of the present invention are obtained.

M1/M2 is determined by time-of-flight secondary ion mass spectrometry. Specifically, the technique is performed using the following device under the following condition or performed using a device under conditions corresponding to the following ones.

Used device: time-of-flight secondary ion mass spectrometer (manufactured by IONTOF GmbH, trade name: "TOF-SIMS5")

Primary ion: $Bi_3^{2+}$
Primary ion acceleration voltage: 25 kV
Measurement area: 500 μm×500 μm
Measurement temperature: equal to or lower than −100° C.

For etching, Ar-GCIB (Ar gas cluster ion beam) is radiated. Furthermore, as a primary ion source, $Bi^{3+}$ is radiated, and the obtained secondary ion is analyzed using time-of-flight type mass spectrometer, thereby obtaining a spectrum.

Ar-GCIB injection pressure: 3 MPa
Measurement surface: 150 μm×150 μm
Measurement mode: high mass resolution It is preferable that the first container, in which at least a portion of the liquid contact portion is formed of glass or electropolished stainless steel, also satisfies the above physical properties.

Electropolished Stainless Steel

As the stainless steel, known stainless steel can be used without particular limitation. Among these, stainless steel with a nickel content equal to or higher than 8% by mass is preferable, and austenite-based stainless steel with a nickel content equal to or higher than 8% by mass is more preferable. Examples of the austenite-based stainless steel include Steel Use Stainless (SUS) 304 (Ni content: 8% by mass, Cr content: 18% by mass), SUS304L (Ni content: 9% by mass, Cr content: 18% by mass), SUS316 (Ni content: 10% by mass, Cr content: 16% by mass), SUS316L (Ni content: 12% by mass, Cr content: 16% by mass), and the like.

As the method for electropolishing the stainless steel, known methods can be used without particular limitation. For example, it is possible to use the methods described in paragraphs [0011] to [0014] in JP2015-227501A, paragraphs [0036] to [0042] in JP2008-264929A, and the like.

Presumably, in a case where the stainless steel is electropolished, the chromium content in a passive layer on the surface thereof may become higher than the chromium content in the parent phase. Presumably, for this reason, from the electropolished stainless steel, metal components may be hardly eluted into the concentrated chemical liquid, and accordingly, further improved effects of the present invention may be obtained.

It is preferable that the stainless steel has undergone buffing. As the buffing method, known methods can be used without particular limitation. The size of abrasive grains used for finishing the buffing is not particularly limited, but is preferably equal to or smaller than #400 because such grains make it easy to further reduce the surface asperity of the stainless steel.

It is preferable that the buffing is performed before the electropolishing.

Furthermore, the stainless steel may be treated by each of multi-stage buffing performed by changing the size of the abrasive grains, acid washing, magnetic fluid polishing, and the like or treated by a combination of two or more kinds of these techniques.

Physical Property 1 of Electropolished Stainless Steel Container (Amount of Metal Component Eluted)

In a case where the first container is an electropolished stainless steel container in which at least a portion of the liquid contact portion is formed of electropolished stainless steel, it is preferable that the electropolished stainless steel container satisfies a condition 3 or a condition 4 in the following test. In a case where the electropolished stainless steel container satisfies the following condition 3 or condition 4, further improved effects of the present invention are obtained.

The test method is as below. A portion of the chemical liquid is adopted as f liquid, and by using f liquid, the liquid contact portion is washed. Furthermore, a portion of the chemical liquid is adopted as g liquid, and under the condition that a ratio of a mass of the washed electropolished stainless steel container to a mass of g liquid becomes 0.25 provided that a liquid temperature of g liquid is 25° C., the washed electropolished stainless steel container is immersed for 24 hours in g liquid having a liquid temperature of 25° C. That is, the test method is a method of immersing the container, which is used for concentrating the chemical liquid, in the chemical liquid which is a target of quality inspection. At this time, provided that the electropolished stainless steel container weighs 200 g, the amount of g liquid used for the immersion is set such that g liquid weighs 50 g in a case where the liquid temperature of g liquid is set to be 25° C. The liquid temperature of g liquid is adjusted such that the liquid temperature is kept at 25° C. while the container is being immersed (for 24 hours) in the liquid.

It is preferable that the immersion may be performed in a clean room which will be described later, because then the influence of the intermixing of an impurity into chemical liquid from the environment (contamination) can be further inhibited.

The immersion tank used for the immersion is not particularly limited. It is preferable that the immersion tank is formed of the aforementioned corrosion-resistance material. Alternatively, it is preferable that a liquid contact portion of the tank is washed with f liquid before use.

Then, an increase in the content of a metal component in g liquid before and after the immersion is measured. The content of the metal components in g liquid before the immersion and the content of the metal components in g liquid after the immersion are measured, and a difference therebetween is adopted as the increase. The metal component means a metal atom derived from both the component present in g liquid as a metal ion (including a complex ion) and the component present in g liquid as a particle. The content of the metal component in g liquid can be measured by inductively coupled plasma mass spectrometry.

For the electropolished stainless steel container, it is preferable that the increase in the metal component (in other words, the amount of the metal component eluted) determined by the aforementioned method satisfies any of the following conditions.

Condition 3: in a case where g liquid having been used for the immersion contains one kind of metal component, the increase in one kind of the metal component before and after the immersion is equal to or smaller than 1 mass ppm.

Condition 4: in a case where g liquid having been used for the immersion contains two or more kinds of metal components, the total increase in two or more kinds of the metal components before and after the immersion is equal to or smaller than 1 mass ppm.

It is preferable that the first container, in which at least a portion of the liquid contact portion is formed of glass or a fluorine-containing polymer, also satisfies the above condition.

Physical Property 2 of Electropolished Stainless Steel Container (Cr/Fe Ratio)

In the electropolished stainless steel container, it is preferable that within a surface of at least a portion of the liquid contact portion, an atom number ratio (Cr/Fe) of the number of chromium atoms contained in a position, which is 1 nm below the surface in a thickness direction of the container, to the number of iron atoms contained in the position is equal to or higher than 1.0.

The upper limit of Cr/Fe is not particularly limited, but is preferably equal to or lower than 3.5, more preferably equal to or lower than 3.0, and even more preferably equal to or lower than 2.5. In a case where Cr/Fe is equal to or higher than 1.0, the electropolished stainless steel container has further improved chemical resistance, and consequently, further improved effects of the present invention are obtained.

In the present specification, Cr/Fe within the aforementioned surface means Cr/Fe measured by the following method.

Measurement method: Ar ion etching combined with X-ray photoelectron spectroscopy
Measurement condition
X-ray source: Al-Kα
X-ray beam diameter: ϕ200 μm
Signal capture angle: 45°
Ion etching condition
Type of ion: Ar Voltage: 2 kV
Area: 2×2 mm
Speed: 6.3 nm/min (expressed in terms of $SiO_2$)

It is preferable that the first container, in which at least a portion of the liquid contact portion is formed of glass or a fluorine-containing polymer, also satisfies the above physical properties.

<Method for Washing First Container>

In the present step, the method for washing the first container is not particularly limited. The method for washing the first container by using a liquid extracted from a portion of the chemical liquid is not particularly limited, and examples thereof include a method of washing the first container (particularly, the liquid contact portion) by spraying a liquid, a method of filling the container with a liquid, a method of immersing the first container in a liquid, and a combination of these.

The washing may be performed only once or plural times. In view of obtaining further improved effects of the present invention, it is preferable to perform the washing two or more times.

a Liquid used for washing is a portion of the chemical liquid as a target of inspection (hereinafter, the chemical liquid used for washing will be referred to as "specific washing solution" as well). The amount of a liquid used is not particularly limited, and can be appropriately selected according to the washing method or the like. The temperature of a liquid is not particularly limited, but is preferably about 10° C. to 100° C. in general.

The present step preferably has at least one kind of step selected from the group consisting of a step of perform acid washing on at least the liquid contact portion (preferably the entirety) of the first container (step of performing washing by using an acid), a step of performing ultrasonic washing on at least the liquid contact portion of the first container, and a step of drying at least the liquid contact portion of the first container. It is preferable that the present step has all of the step of performing acid washing, the step of performing ultrasonic washing, and the step of drying.

The acid which can be used in the step of performing acid washing is not particularly limited, and may be appropriately selected according to the material of the liquid contact portion of the first container or the like.

In the step of performing ultrasonic washing, the oscillation frequency of ultrasonic washing is not particularly limited and is preferably 10 to 200 kHz in general. Generally, the lower the oscillation frequency, the larger the size of particles that can be removed. Furthermore, the higher the oscillation frequency, the smaller the size of particles that can be removed. The oscillation frequency can be appropriately selected according to the particles that have to be removed (particles that have to be regarded as objects to be removed). For example, in order to remove smaller particles, the oscillation frequency may be further increased.

The ultrasonic power at the time of the ultrasonic washing is not particularly limited, and can be appropriately selected according to the size of an ultrasonic vibrator and the desired power density of ultrasound. Generally, the ultrasonic power is preferably 50 to 300 W. Usually, the higher the ultrasonic power, the more preferable because the washing ability is further improved.

The time of the ultrasonic washing is not particularly limited, and is preferably equal to or longer than 10 seconds in general. The upper limit thereof is not particularly limited. However, in view of further improving throughput, the upper limit is preferably equal to or shorter than 100 seconds. The time of the ultrasonic washing is more preferably 20 to 50 seconds.

The washing solution used in the step of performing ultrasonic washing is not particularly limited, but is preferably at least one kind of washing solution selected from the group consisting of the aforementioned specific washing solution, an acid, and pure water.

Particularly, it is preferable to perform the ultrasonic washing by using at least one kind of washing solution selected from the group consisting of the specific washing solution and an acid.

The drying step is a step of drying the washed first container. As the method for drying the container, known methods can be used without particular limitation. Examples thereof include a method of blowing hot air to the container, a method of allowing the container to stand still in an atmosphere controlled in terms of temperature and/or humidity, and the like.

Particularly, as the hot air and the atmosphere, it is preferable to use clean air. As the method for generating the clean air, known methods can be used without particular limitation. Examples thereof include a method of using the air having passed through a filter (a High Efficiency Particulate Air Filter (HEPA) filter and/or an Ultra Low Penetration Air (ULPA) filter).

The order of performing the step of washing the liquid contact portion of the first container by using the washing solution described above, the step of performing acid washing, and the step of performing ultrasonic washing is not particularly limited. The order of performing these steps can be appropriately selected according to the material of the liquid contact portion of the used first container, the type of the chemical liquid used, and the like.

It is preferable that the drying step is performed after each of the above steps is finished.

<Clean Room>

In the quality inspection method for a chemical liquid according to the embodiment of the present invention, the step W and the step A, which will be described later, are performed in a clean room. It is preferable that steps (for example, the step B, the step C, and other steps) other than the above are performed in the same clean room. It is more preferable that at least the step B is performed in the clean room. It is even more preferable that all the steps are performed in the clean room.

The clean room has cleanliness equal to or higher than class 4 specified in the International Standard ISO14644-1: 2015 established by the International Organization for Standardization. The clean room is preferably a class 3 clean room, more preferably a class 2 clean room, and even more preferably a class 1 clean room.

[Step A]

The step A is a step of adopting a portion of the chemical liquid as b liquid and performing concentration of b liquid by using the washed first container described above so as to obtain c liquid. Each of b liquid used in the step A and a liquid used in the step W corresponds to a liquid extracted from the same chemical liquid.

The method for concentrating b liquid is not particularly limited, and examples thereof include concentration by heating and/or pressure reduction.

In a case where the concentration by heating (heating method) is adopted, the temperature (hereinafter, referred to as "temperature condition" as well) of b liquid (and b liquid that is being concentrated) is preferably 100° C. to 250° C.

In contrast, in a case where the concentration by pressure reduction is adopted (pressure reduction method, in other words, in a case where the concentration is performed under reduced pressure), the temperature of b liquid (and b liquid that is being concentrated) is preferably 10° C. to 100° C.

b Liquid may be concentrated by using the heating method and a concentration method in combination. In a case where the heating method is used, it is preferable that the temperature condition is equal to or higher than 100° C. because then the time required for the concentration is further reduced. Meanwhile, it is preferable that the temperature condition is equal to or lower than 250° C. because then it becomes harder for the specific component to change. Particularly, in a case where the heating method is adopted, the temperature condition is more preferably 120° C. to 230° C., and even more preferably 150° C. to 200° C.

The concentration is performed under at least one kind of inert gas selected from the group consisting of an Ar gas, a He gas, and a $N_2$ gas or under reduced pressure. In a case where the concentration is performed in this way, the specific components are inhibited from changing in the process of concentration.

In the step A, a factor of concentration is not particularly limited, but is preferably 2 to 1,000,000. It is preferable that the factor of concentration is equal to or greater than 2, because then it is easier to detect the specific component in the process of concentration. It is preferable that the factor of concentration is equal to or smaller than 1,000,000, because then the time required for the concentration is further reduced, and it becomes harder for the specific component to change. The factor of concentration is more preferably 10 to 10,000, and even more preferably 100 to 1,000.

The volume of c liquid before concentration is not particularly limited. Generally, the volume of c liquid is preferably equal to or smaller than 10 L, and more preferably equal to or smaller than 5 L. It is preferable that the volume of c liquid before concentration is equal to or smaller than 5 L, because then the time required for the concentration is further reduced.

[Step B]

The step B is a step of performing measurement of the content of the specific component in c liquid obtained in the step A. The specific component is as described above as the component that the chemical liquid contains.

In the present step, the measurement is performed by at least one kind of measurement method selected from the group consisting of gas chromatography mass spectrometry (GC/MS), gas chromatography tandem mass spectrometry (GC/MS/MS), gas chromatography atomic emission detection (GC/AED), gas chromatography quadrupole time-of-flight type mass spectrometry (GC-Q-TOF/MS), direct sample introduction-type mass spectrometry (DI-MS), high-performance liquid chromatography mass spectrometry (LC/MS), high-performance liquid chromatography tandem mass spectrometry (LC/MS/MS), high-performance liquid chromatography time-of-flight type mass spectrometry (LC/TOF/MS), inductively coupled plasma mass spectrometry (ICP-MS), high-frequency inductively coupled plasma emission spectrometry (ICP-AES), temperature programmed desorption mass spectrometry (TPD-MS), ion chromatography (IC), nuclear magnetic resonance spectrometry (NMR), and atomic absorption spectrometry.

These measurement methods are classified into organic analysis for measuring the content of an organic substance in a concentrated liquid and inorganic analysis for measuring the content of an inorganic substance in a concentrated liquid.

The organic analysis includes GC/MS, GC/MS/MS, GC/AED, GC-Q-TOF/MS, DI-MS, LC/MS, LC/MS/MS, LC/TOF/MS, TPD-MS, IC, and NMR. Among these, GC/MS, GC/MS/MS, GC/AED, GC-Q-TOF/MS, DI-MS, LC/MS, LC/MS/MS, LC/TOF/MS, TPD-MS, and NMR are preferable.

The inorganic analysis includes GC/AED, ICP-MS, ICP-AES, TPD-MS, IC, and atomic absorption spectrometry. Among these, ICP-MS, ICP-AES, IC, and atomic absorption spectrometry are preferable.

In view of obtaining further improved effects of the present invention, the measurement is preferably performed by at least one kind of measurement method selected from the group consisting of GC/MS, GC/MS/MS, LC/MS, LC/MS/MS, and ICP-MS, more preferably performed by at least one kind of measurement method selected from the group consisting of GC/MS, LC/MS, LC/MS/MS, and ICP/MS, and even more preferably performed by at least one kind of measurement method selected from the group consisting of LC/MS and LC/MS/MS.

As described above, in the quality inspection method for a chemical liquid according to the embodiment of the present invention, in view of more accurately evaluating the defect inhibition performance of the chemical liquid, it is preferable to measure the content of each of the specific organic substance and the specific inorganic substance in the chemical liquid, and the measurement preferably includes organic analysis and inorganic analysis.

Particularly, it is preferable that the inorganic analysis is for measuring the content of at least 5 or more kinds of atoms selected from the group consisting of Ag, Al, As, Au, Ba, Ca, Cd, Co, Cr, Cu, Fe, Ga, Ge, K, Li, Mg, Mn, Mo, Na, Nb, Ni, Pb, Sb, Sn, Sr, Ta, Th, Ti, Tl, V, W, Zn, and Zr in c liquid. Five or more kinds of the atoms more preferably contain at least two or more kinds of atoms selected from the group consisting of Al, Fe, and Ti.

Furthermore, it is preferable that the organic analysis is for measuring the content of each of the compounds represented by Formula (1) to Formula (7) in c liquid.

The above measurement methods are optimized for different targets of analysis among the specific components. Therefore, it is preferable to select the measurement method according to the target subject (specific component). Preferred factors of concentration for the measurement methods will be shown below.

GC/MS(/MS): gas chromatography (tandem) mass spectrometry
Factor of concentration: 2 to 100,000
GC-AED: gas chromatography atomic emission detection (used device: gas chromatograph with atomic emission detector)
Factor of concentration: 2 to 100,000
GC-Q-TOF/MS: gas chromatography quadrupole time-of-flight type mass spectrometry
Factor of concentration: 2 to 100,000
DI-MS: direct sample introduction-type mass spectrometry
Factor of concentration: 100 to 1,000,000
LC/MS(/MS): high-performance liquid chromatography (tandem) mass spectrometry
Factor of concentration: 2 to 100,000
LC-Q-TOF/MS: high-performance liquid chromatography quadrupole time-of-flight type mass spectrometry
Factor of concentration: 2 to 100,000
ICP-MS: inductively coupled plasma mass spectrometry
Factor of concentration: 2 to 100,000
ICP-AES: inductively coupled plasma emission spectrometry
Factor of concentration: 2 to 100,000
TPD-MS: temperature programmed desorption mass spectrometry
Factor of concentration: 10 to 100,000
IC: ion chromatography
Factor of concentration: 2 to 100,000
NMR: nuclear magnetic resonance spectrometry
Factor of concentration: 10 to 100,000
Atomic absorption spectrometry
Factor of concentration: 10 to 100,000
(GC/MS(/MS))

The detector for gas chromatograph (GC) includes a hydrogen flame ionization type detector (FID), a flame photometric detector (FPD), and the like. A mass spectrometer (MS) is one of the detectors for GC. Gas chromatograph using MS as a detector and an analysis method using the same are called gas chromatograph mass spectrometer or gas chromatography mass spectrometry (GC/MS). GC/MS is constituted with two devices exploiting different separation techniques such as (1) gas chromatograph (GC) performing chromatographic separation and (2) mass spectrometer (MS) performing mass separation.

The components of a mixture sample of interest are separated by GC, and each of the components is output as a column of a peak called chromatogram. MS in GC/MS ionizes the components output from GC and analyzes the mass. Among the detectors for GC, MS is a detector which is excellent in qualitative analysis and can perform quantitative analysis as well. Although both the GC and GC/MS are devices separating and analyzing a gas, these can be used for both the liquid sample and solid sample. In a case where a liquid sample is used, the sample may be heated and gasified at the inlet of GC and then introduced into GC. As the specific component suited for GC and GC/MS analysis, specific organic substances that may be gasified at a boiling point equal to or lower than 300° C. are preferable. The polarity of the analysis target is not particularly limited. As the analysis target, specific organic substances with polarity ranging from non-polarity to neutral polarity are preferable.

Meanwhile, for analyzing specific organic substances having a large molecular weight and a higher boiling point and specific organic substances having high polarity, LC and LC/MS which will be described later are preferable.

(GC-AED)

GC-AED is a measurement method (measurement device) in which a substance separated by GC is led into helium plasma and decomposed into atoms, the excited atoms generate specific light, and the light is detected by a photodiode array (PDA). PDA can detect multiple wavelengths at the same time. Accordingly, a plurality of elements contained in c liquid can be simultaneously detected, and by checking the emission line for each peak and differentiating the interference with other elements, an element as a measurement target can be accurately determined.

(GC-Q-TOF/MS)

GC-Q-TOF/MS is a hybrid-type analyzer obtained by combining a quadrupole MS used at an early stage with a time-of-flight type mass spectrometer (TOF-MS) used at a late stage, and can perform MS/MS measurement with high resolution. Each of the components separated by gas chromatography is ionized, passes through the quadrupole MS portion, and is led into the TOF-MS portion. In the TOF-MS portion, pulse voltage is applied by a pusher (electrode), and the ions fly at different speeds according to their mass number. The ions fly the same distance for a flying time unique to their mass number and then reach the detector. By measuring the time, a mass spectrum is obtained.

(DI-MS)

The direct sample introduction-type mass spectrometry is a method of directly introducing c liquid into an ion source without passing through gas chromatograph (GC). Accordingly, hardly volatile specific organic substances, which are difficult to analyze by GC, and specific organic substances easily decomposed by heat can be accurately quantified. Furthermore, in a case where the purity of c liquid is high, the conditions of gas chromatogram do not need to be examined, and accordingly, a mass spectrum is more simply obtained. In addition, because the sample can be heated up to about 500° C., it is also possible to detect a specific organic substance having a high boiling point. Moreover, because the detectable mass ranges to about m/Z=1,024, a specific component having a larger molecular weight can also be effectively quantified.

(LC/MS(/MS))

LC (high-performance chromatography) is a measurement method of separating components based on a difference between the affinity (retention ability) of each component in a sample with a stationary phase and the affinity of the same component with a mobile phase, and detecting a target based on ultraviolet-visible absorption, fluorescence, electric conductivity, and the like according to the properties of the components. In LC, qualitative analysis for a detection target is mainly performed based on a retention time, and quantitative analysis is performed based on peak intensity and/or area. In contrast, mass spectrometry (MS) is a highly sensitive measurement method of ionizing a sample component, separating the obtained ions based on a mass to charge ratio (m/Z) in a vacuum, and measuring the intensity of each of the ions. Because the obtained mass spectrum can show how much ions having a certain mass are in the sample, MS is effective for qualitative analysis.

The high-performance liquid chromatography mass spectrometer (LC/MS) is a device obtained by combining the high-performance liquid chromatograph (LC) having excellent resolution with the mass spectrometer (MS) excellent in qualitative analysis. In a mass spectrum obtained by scanning measurement, a molecular weight and structural information are assigned to eluted components so as to complement the qualitative analysis performed based on the retention time obtained by other LC detectors (for example, PDA and the like).

In LC/MS, hardly volatile and/or thermolabile specific components that GC/MS cannot excellently analyze can be quantified as long as those components are dissolved in a mobile phase (liquid). That is, LC/MS has an advantage of being applicable to a wide variety of analysis targets.

(LC-Q-TOF/MS)

By separating accelerated ions based on a flying time and measuring the flying time, the time-of-flight type mass spectrometer (TOF/MS) can accurately measure a molecular mass with high resolution. LC-Q-TOF/MS is provided with a quadrupole and a quadrupole ion guide disposed in front of TOF-MS and comprises the function of a triple quadrupole. Therefore, LC-Q-TOF/MS can collect accurate data on the mass of fragment ions or molecular ions useful for analyzing the structure of an unknown substance.

(ICP-MS)

ICP-MS is an elemental analyzer which can analyze multiple elements with high sensitivity and high sample throughput. ICP-MS uses high-frequency inductively coupled plasma (ICP) as an ion source and detects the generated ions by using a mass spectrometer (MS). ICP-MS can simultaneously measure substantially all the elements on the periodic table, and can measure the elements at a sub-ng/L (ppt) concentration level. Furthermore, ICP-MS can perform qualitative analysis, semi-quantitative analysis, and quantitative analysis, and can measure an isotope ratio as well because the measurement is mass spectrometry.

(ICP-AES)

ICP emission spectrometer (ICP-AES) is device which introduces a liquid sample into high-temperature argon plasma by atomizing the sample, is excited by heat energy, sorts the generated light into spectra unique to elements by using a spectroscope, and performing qualitative analysis based on wavelength and quantitative analysis based on intensity. The emission spectrometry is relative analysis. Accordingly, ICP-AES measures the concentration of a measurement sample by comparison with the intensity of a standard liquid of an element of known concentration.

(TPD-MS)

TPD-MS is a device in which a mass spectrometer (MS) is directly connected to a special heating device with a temperature controller. The temperature programmed desorption mass spectrometry is a technique of tracking the concentration change of a gas, which is generated from c liquid heated according to a predetermined heating program, as a function of temperature or time. Because TPD-MS is online analysis, this technique can simultaneously detect an inorganic component such as moisture and an organic component by a single measurement. Furthermore, TPD-MS can qualitatively analyze organic components by performing GC/MS analysis on the collected entrapped substances.

(IC)

Ion chromatography is a high-performance liquid chromatography (ion exchange chromatography) in which an ion exchange resin is used as a stationary phase and an aqueous solution of electrolyte is used as a mobile phase (eluent). In the ion chromatography, a component is identified by checking whether a retention time of a peak in the obtained chromatogram coincides with a retention time of a standard liquid. As a detector, for example, an electric conductivity meter is preferable. In a suppressor method in which an ion exchange membrane is installed in front of the detector, ions contained in c liquid can be measured with high sensitivity.

(NMR)

Nuclear magnetic resonance spectrometry (NMR) is a measurement method of analyzing the molecular structure of a substance at an atomic level by injecting atomic nuclei into a magnetic field and observing the resonance of nuclear spin. Examples of the analyzer analyzing the molecular structure at the atomic nucleus level also include an electron microscope, an X-ray diffractometer, and the like. The NMR device has an advantage of being capable of analyzing an analysis target in a nondestructive manner.

(Atomic Absorption Spectrometry)

In a case where an analysis target is sprayed in a frame or heated in a graphite furnace such that an element to be measured becomes atomic vapor (atomized), and light having a wavelength unique to the element to be measured is passed through the atomic vapor, the atoms in a ground state absorb the light and become excited. From the absorption of the light (absorbance), the concentration of the element can be measured.

The content of the specific component measured in the present step may be an absolute quantity or a relative quantity. In a case where the content is an absolute quantity, the absolute quantity can be measured by, for example, an absolute calibration curve method, a standard addition method, an internal standard method, and the like.

In the absolute calibration curve method, several drops of standard samples in which the content of the specific component is stepwise changed are prepared (the content of the specific component is known), and the responses from a measurement instrument to the standard samples of different contents are plotted on the ordinate, thereby creating a calibration curve. Then, a concentrated liquid is measured under the same condition, and from the obtained responses, the content of the specific component in the concentrated liquid is determined.

In the standard addition method, a specific component is added to a concentrated liquid, several drops of samples in which the amount of the specific component added is stepwise changed are prepared, and the samples and the concentrated liquid are measured together, thereby creating the same calibration curve as that described above. A point at which the ordinate of the calibration curve becomes zero is extrapolated, and the content of the specific component originally contained in the concentrated liquid is determined.

In the internal standard method, a certain amount of an internal standard substance is added to several drops of samples in which the content of the specific component is stepwise changed, thereby preparing a standard sample and creating a calibration curve. Then, the internal standard substance of known quantity is added to a concentrated liquid, and from the calibration curve, the content of the specific component in the concentrated liquid is determined.

Among these, in view of obtaining further improved effects of the present invention, the internal standard method is preferable.

In a case where the content of the specific component is a relative quantity, the value of response (absorbance, ion count, or the like) of the device obtained by measuring the samples under the same condition can be adopted as the content.

By each of the devices, the content of the specific component in c liquid can be identified. Here, in a case where the structure of the specific component is known, by plotting a calibration curve by using a reference substance thereof, the absolute concentration can be determined. Alternatively, by adding the reference substance in advance as being typically performed in NMR, the concentration can also be calculated from the difference in peak intensity between the specific component and the reference substance.

For a chemical liquid for state-of-the-art semiconductors or the like, it is necessary to detect compounds of quantities incomparably smaller than those of compounds detected so far. Therefore, a concentration step should be performed as a pretreatment. However, there are many compounds from which only a slight peak is detected even after the concentration step, and it is extremely difficult to identify such compounds. Furthermore, there is a library of peaks for GC/MS, and accordingly, compounds can be identified from the peak shape. In contrast, for LC/MS, there is no such a library identifying peaks. Therefore, sometimes it is difficult to identify compounds even though the compounds can be detected by LC/MS. In this case, it is difficult to control the absolute quantity by the reference substance (identified compound), and accordingly, compounds are controlled based on the relative quantity.

[Step C]

The present quality inspection method has a step of comparing the content of the specific component obtained in the step B with a preset standard value.

In a case where the value of the content of the specific component measured in the step B is an absolute quantity, the standard value is predetermined as an absolute quantity. In a case where the value of the content of the specific component measured in the step B is a relative quantity, the standard value is predetermined as a relative quantity. A plurality of standard values may be determined according to the type of the specific component, the measurement method, and the like. Alternatively, according to the type of the specific components, the measurement method, and the like, a standard value as an absolute quantity and a standard value as a relative quantity may be determined.

The standard value is not particularly limited as long as it is predetermined. In view of obtaining further improved effects of the present invention, it is preferable to determine the standard value by the method described in the standard value determination step which will be described later.

[Step D]

The present quality inspection method may additionally have a step D of determining the chemical liquid as being inadequate and discarding the chemical liquid in a case where the content of the specific component is greater than the standard value.

[Step E]

The present quality inspection method may have a step of purifying the chemical liquid in a case where the content of the specific component is greater than the standard value and then performing again the step W, the step A, the step B, and the step C.

The method for purifying the chemical liquid in this case will be described later.

[Other Steps]

The present quality inspection method may further have other steps, as long as the effects of the present invention are exerted. Examples of those other steps include a specific component determination step including a step W3, a step A3, a step B3, and a step C3 which are performed in this order, a standard value determination step having a step W4, a step A4, a step B4, a step S, and a step U which are performed in this order, a step X which is a chemical liquid extraction step, and the like.

<Specific Component Determination Step>

The present quality inspection method may further have a specific component determination step before the step W described above or between the step W and the step A. The specific component determination step includes a step W3, a step A3, a step B3, and a step C3 which are performed in this order.

(Step W3)

The step W3 is a step of preparing a third container having a liquid contact portion of which at least a portion is formed of the corrosion-resistance material described above, adopting a portion of the chemical liquid as h liquid, and washing at least a portion of the liquid contact portion of the third container by using h liquid.

The third container used in the present step is not particularly limited as long as at least a portion of the liquid contact portion is formed of the corrosion-resistance material. The aspect of the third container is the same as that of the first container used in the step W.

The method for washing at least a portion of the liquid contact portion of the third container by using h liquid is not particularly limited. The aspect of this method is the same as that of the method for washing at least a portion of the liquid contact portion of the first container by using a liquid described above.

(Step A3)

The step A3 is a step of adopting a portion of the chemical liquid as i liquid and performing concentration of i liquid by using the washed third container so as to obtain three or more kinds of j liquids having different factors of concentration. The concentration is performed under at least one kind of inert gas selected from the group consisting of an Ar gas, a He gas, and a $N_2$ gas or under reduced pressure. The step W3 and the step A3 are performed in a clean room having cleanliness equal to or higher than class 4 specified in the International Standard ISO14644-1:2015 established by the International Organization for Standardization.

The method for performing concentration of i liquid is not particularly limited, and the aspect of the method is the same as the aspect described above as the method for performing concentration of b liquid in the step A.

In the present step, three or more kinds of j liquids having different factors of concentration are obtained. The factors of concentration of the liquids are not particularly limited, but it is preferable that the difference in the factor of concentration among the liquids is about several fold to 100 fold. For example, a combination of a 100× concentrated liquid, a 300× concentrated liquid, a 500× concentrated liquid, a 1,000× concentrated liquid, and the like is preferable.

(Step B3)

The step B3 is a step of measuring the content of an organic substance, in which m/Z is 300 to 1,000, in j liquids by at least one kind of measurement method selected from the group consisting of high-performance liquid chromatography mass spectrometry and gas chromatography mass spectrometry. m/Z is a value obtained by dividing the abscissa in a mass spectrum, that is, the mass number of the detected specific component by charge.

(Step C3)

The step C3 is a step in which in a case where two or more kinds of organic substances are commonly detected from all of three or more kinds of j liquids, from a coefficient of correlation obtained by performing linear regression on the factors of concentration and the content of each of two or more kinds of the organic substances and a coefficient of correlation obtained by performing linear regression on the factors of concentration and the total content of organic substances in a combination of two or more kinds of the organic substances, a maximum coefficient of correlation is selected, and an organic substance or a combination of organic substances from which the maximum coefficient of correlation is obtained is determined as a specific component The organic substances commonly detected from all of three or more kinds of j liquids are more likely to be components contained in the chemical liquid. In other words, such components are more unlikely to be impurities intermixed at the stage of preparing j liquids. Therefore, in a case where such organic substances are determined as the specific component, the defect inhibition performance of the chemical liquid can be more accurately evaluated.

In a case where two or more kinds of organic substances are commonly detected from all of three or more kinds of j liquids, first, from the following two kinds of coefficients of correlation, a maximum (positive) coefficient of correlation is selected.

Coefficient of correlation obtained by performing linear regression on factors of concentration and content of each of two or more kinds of organic substances Coefficient of correlation obtained by performing linear regression (linear approximation) on factors of concentration and total content of organic substances in combination of two or more kinds of organic substances The coefficient of correlation is calculated through a regression equation of $Y=aX+b$ by a least square method.

By determining an organic substance or a combination of the organic substances, from which a maximum positive coefficient of correlation is obtained in a case where linear regression is performed on the content and the factors of concentration and on the total content of two or more kinds of any organic substances selected from the group consisting of two or more kinds of organic substances and the factors of concentration, as the specific component, the defect inhibition performance of the chemical liquid can be more accurately measured.

In a case where two or more kinds of organic substances are commonly detected from all of three or more kinds of j liquids, and the coefficients of correlation obtained from the contents thereof, the content of a combination thereof, and the factors of concentration are the same as each other, two or more kinds of the organic substances or a combination thereof may be determined as the specific component.

<Standard Value Determination Step>

It is preferable that the present quality inspection method further has a standard value determination step of determining a standard value at a point in time when the aforementioned specific component determination step has finished but the step C is not yet started.

The standard value determination step has the following steps that are performed in the following order.

Step W4 of preparing n pieces of fourth containers each having a liquid contact portion of which at least a portion is formed of a corrosion-resistance material, preparing n kinds of chemical liquids manufactured by different manufacturing methods, obtaining twice a portion of each of n kinds of the chemical liquids, naming the obtained chemical liquids as $p_1$ liquid and $p_2$ liquid respectively, and washing at least a portion of the liquid contact portion of each of the fourth containers by using each of $p_1$ liquids Step A4 of performing concentration of each of the corresponding liquids $p_2$ by using each of the fourth containers washed with each of the liquids $p_1$ so as to obtain n kinds of liquids q Step B4 of performing measurement of a content of a specific component in each of q liquids by at least one kind of measurement method selected from the group consisting of high-performance liquid chromatography mass spectrometry and gas chromatography mass spectrometry Step S of evaluating a defect inhibition performance of each of n kinds of the chemical liquids by using a defect inspection device Step T of creating a calibration curve by performing linear regression on the content of the specific component and the defect inhibition performance Step U of determining the content of the specific component corresponding to a predetermined defect inhibition performance as a standard value by using the calibration curve At least the step W4 and the step A4 are performed in a clean room having cleanliness equal to or higher than class 4 specified in the International Standard ISO14644-1:2015 established by the International Organization for Standardization. The aspect of the clean room will not be described because it is the same as described above.

(Step W4)

In the step W4, first, n pieces of predetermined fourth container are prepared. The fourth container is not particularly limited as long as at least a portion of the liquid contact portion thereof is formed of a corrosion-resistance material. Specifically, the first container described above can be used, and the aspect of the first container is the same as that of the fourth container.

n is an integer equal to or greater than 3, and preferably equal to or greater than 4. Generally, n is preferably equal to or smaller than 10. In a case where n is equal to or greater than 3, the calibration curve, which will be described later, is created based on three or more measurement points. Therefore, the standard value can be more accurately determined.

Next, n kinds of chemical liquids manufactured by different manufacturing methods are prepared. The manufacturing methods of the chemical liquid are as described above. The different manufacturing methods are not particularly limited. Typically, in a case where the chemical liquids are obtained by manufacturing methods in which a substance to be purified is filtered through a filter, it is preferable that at least one kind of condition selected from the group consisting of the number of filters used, the pore structure of the filter, the pore size of the filter, the material of the filter, and the number of times of circulation varies between the manufacturing methods. In a case where the above condition varies, the content of the specific component varies between the obtained chemical liquids.

The order of preparing n kinds of the chemical liquids and the order of preparing n pieces of the fourth container are not particularly limited.

Then, a portion of each of n kinds of the chemical liquids is extracted twice, and the obtained liquids are named $p_1$ liquid and $p_2$ liquid respectively. For example, in a case where three kinds of chemical liquids manufactured different manufacturing methods are prepared, and the liquids are named $C_1$, $C_2$, and $C_3$, from $C_1$, $p_1$ liquid ($p_{1-1}$) and $p_2$ liquid ($p_{2-2}$) are obtained. In this case, the components of $p_{1-1}$ liquid are the same as the components of $p_{2-1}$ liquid. In this way, $p_1$ liquid and $p_2$ liquid are obtained from the respective chemical liquids. That is, $p_{1-2}$ and $p_{2-2}$ are obtained from $C_2$, and $p_{1-3}$ and $p_{2-3}$ are obtained from $C_3$.

Thereafter, by using each of $p_1$ liquids, at least a portion of the liquid contact portion of each of the fourth containers is washed.

At this time, as a washing method, it is possible to use the same as the method for washing at least a portion of the liquid contact portion of the first container by using a liquid in the step W. Therefore, the washing method will not be described.

In a case where three fourth containers are prepared, each of the fourth containers is washed with $p_{1-1}$ liquid, $p_{1-2}$ liquid, and $p_{1-3}$ liquid described above. That is, by using $p_1$ liquid corresponding to each of the chemical liquids manufactured by different manufacturing methods, each of the fourth containers is washed.

(Step A4)

The step A4 is a step of performing concentration of each of the corresponding $p_2$ liquids by using the fourth containers washed with each of $p_1$ liquids so as to obtain q liquid. At this time, the concentration is performed under at least one kind of inert gas selected from the group consisting of an Ar gas, a He gas, and a $N_2$ gas or under reduced pressure. Other concentration methods will not be described because they are the same as the methods described above in the step A.

The concentration of each of the corresponding $p_2$ liquids by using the fourth containers washed with each of $p_1$ liquids means that $p_{2-1}$ liquid is concentrated in the fourth container washed with $p_{1-1}$ liquid, $p_{2-2}$ liquid is concentrated in the fourth container washed with $p_{1-2}$ liquid, and $P_{2-3}$ liquid is concentrated in the fourth container washed with $p_{1-3}$ liquid.

(Step B4)

The step B4 is a step of measuring the content of the specific component in q liquid obtained as above by at least one kind of measurement method selected from the group consisting of LC/MS and GC/MS. The measurement method and the like will not be described because they are the same as those described above in the step B.

The number of q liquids obtained is the same as the number of chemical liquids prepared (number represented by n). In the present step, the content of the specific component corresponding to each of q liquids is obtained as a measurement result (which may be an absolute quantity or a relative quantity).

(Step S)

In the step S, by using a defect inspection device, the defect inhibition performance of each of n kinds of the chemical liquids is evaluated. The defect inspection device is a device irradiating the chemical liquid, with which a wafer is coated, with laser beams, detecting laser beams scattered due to defects present on the wafer, and detecting the defects present on the wafer. At the time of laser beam irradiation, the device performs measurement while rotating the wafer. Therefore, from the rotation angle of the wafer and the radial position of the laser beams, the device can determine the coordinate locations of foreign substances and defects. Examples of such a device include SP-5 manufactured by KLA-Tencor Corporation. In addition to this, wafer surface inspection devices (typically, follow-up models of "SP-5") having resolution equal to or higher than the resolution of "SP-5" may also be used.

The method for evaluating the defect inhibition performance by using the defect inspection device will be described in Examples.

(Step T)

The step T is a step of creating a calibration curve by performing linear regression on the content of the specific component according to (n kinds) of q liquids and (evaluation results) of the defect inhibition performance according to each of the chemical liquids. The linear regression method will not be described because the method described above in the specific component determination step can be used.

Specifically, the content of the specific component according to q liquids is plotted on the ordinate, the defect inhibition performance according to the corresponding chemical liquid is plotted on the abscissa, and regression is performed using a linear function of $Y=aX+b$, thereby obtaining a calibration curve.

(Step U)

The step U is a step of determining the content of the specific component corresponding to a predetermined defect inhibition performance as a standard value by using the obtained calibration curve. The predetermined defect inhibition performance means, for example, a defect inhibition performance (or a value obtained by taking a certain safety factor into account based on the defect inhibition performance) considered to be adequate as the defect inhibition performance of the chemical liquid. By using the calibration curve, the content of the specific component corresponding to the defect inhibition performance is calculated, and the calculated content is determined as a standard value.

<Chemical Liquid Extraction Step>

(Step X)

The present quality inspection method may further have a step X of extracting the chemical liquid from a chemical liquid storage body, which has a container with a lid and the chemical liquid sealed in the container with a lid, in a clean room before the step W.

In a case where the chemical liquid storage body is not opened until the quality inspection is started after the manufacturing of the chemical liquid and then opened in the clean room, further improved effects of the present invention are obtained.

[Manufacturing Method of Chemical Liquid]

The manufacturing method of a chemical liquid according to an embodiment of the present invention is a manufacturing method of a chemical liquid containing an organic solvent. The manufacturing method has a step P of purifying a substance to be purified containing an organic solvent so as to obtain a substance to be purified having undergone purification, a step W2 of preparing a first container having a liquid contact portion of which at least a portion is formed of at least one kind of material selected from the group consisting of glass, a fluorine-containing polymer, and electropolished stainless steel, adopting a portion of the substance to be purified having undergone purification as a2 liquid, and washing at least a portion of the liquid contact portion by using a2 liquid, a step A2 of adopting a portion of the substance to be purified having undergone purification as b2 liquid and performing concentration of b2 liquid by using the first container so as to obtain c2 liquid, a step B2 of performing measurement of a content of a specific component in c2 liquid, a step C2 of comparing the content of the specific component with a preset standard value, a step E of determining the substance to be purified having undergone purification as a new substance to be purified and repeating the step P, the step W2, the step A2, the step B2, and the step C2 in this order in a case where the content of the specific component is greater than the standard value, and a step Z of determining the substance to be purified having undergone purification as being adequate and adopting the substance to be purified having undergone purification as a chemical liquid. The step P, the step W2, the step A2, the step B2, the step C2, the step E, and the step Z are performed in this order, and at least the step P, the step W2, and the step A2 are performed in a clean room having cleanliness equal to or higher than class 4 specified in the International Standard ISO14644-1:2015 established by the International Organization for Standardization. The concentration in the step A2 is performed under at least one kind of inert gas selected from the group consisting of an Ar gas, a He gas, and $N_2$ gas or under reduced pressure, and the measurement in the step B2 is performed by at least one kind of measurement method selected from the group consisting of gas chromatography mass spectrometry, gas chromatography tandem mass spectrometry, gas chromatography atomic emission detection, gas chromatography quadrupole time-of-flight type mass spectrometry, direct sample introduction-type mass spectrometry, high-performance liquid chromatography mass spectrometry, high-performance liquid chromatography tandem mass spectrometry, high-performance liquid chromatography time-of-flight type mass spectrometry, inductively coupled plasma mass spectrometry, inductively coupled plasma emission spectrometry, temperature programmed desorption mass spectrometry, ion chromatography, nuclear magnetic resonance spectrometry, and atomic absorption spectrometry.

Hereinafter, regarding the manufacturing method of a chemical liquid, aspects of each of the steps will be described.

[Step P]

The step P is a step of purifying a substance to be purified containing an organic solvent so as to obtain a substance to be purified having undergone purification.

The organic solvent is not particularly limited, but the organic solvent contained in the chemical liquid described above is preferable. The content of the organic solvent in the substance to be purified is not particularly limited, but is preferably equal to or greater than 90% by mass in general with respect to the total mass of the substance to be purified. One kind of substance to be purified may be used singly, or two or more kinds of substances to be purified may be used in combination. In a case where two or more kinds of substances to be purified are used in combination, the total content thereof is preferably within the above range.

The substance to be purified may contain components other than the organic solvent. Examples of those other components other than the organic solvent include the specific component described above. The content of the specific component in the substance to be purified is not particularly limited, but is preferably equal to or smaller than 10% by mass in general with respect to the total mass of the substance to be purified.

The substance to be purified may contain only one kind of specific component or two or more kinds of specific components. In a case where the substance to be purified contains two or more kinds of specific components, the total content thereof is preferably within the above range.

The substance to be purified may be prepared by means of purchasing or the like or may be generated by reacting raw materials. It is preferable to use a substance to be purified in which the content of the aforementioned specific component is small. Examples of commercial products of such a substance to be purified include those called "high-purity grade products".

The purification step is in other words a step of performing purification such that the content of the specific component in the substance to be purified becomes a desired value.

The purification step may further have a reaction step of reacting raw materials so as to obtain a substance to be purified containing an organic solvent.

The method for purifying the substance to be purified is not particularly limited, and examples thereof include the following purification treatments II to IV. The method may further have a purification treatment I.

The purification treatment I is a treatment of purifying the raw materials in the reaction step.

The purification treatment II is a treatment of purifying the substance to be purified at the time of obtaining the substance to be purified in the reaction step and/or after the substance to be purified is obtained.

The purification treatment III is a treatment of purifying substances to be purified in a case where substances to be purified each containing one kind of organic solvent are obtained and mixed together in the reaction step so as to manufacture a chemical liquid containing two or more kinds of organic solvents.

The purification treatment IV is a treatment of mixing together substances to be purified and then purifying the mixed substances to be purified in a case where substances to be purified each containing one kind of organic solvent are obtained and mixed together in the reaction step so as to manufacture a chemical liquid containing two or more kinds of organic solvents.

In a case where commercial products used as the substance to be purified, the purification treatment II may be performed so as to adjust the content of the specific component.

Each of the purification treatments I to IV may be performed only once or two or more times.

Specifically, examples of the purification method include an aspect in which a first ion exchange treatment of performing an ion exchange treatment on the substance to be purified, a dehydration treatment of dehydrating the substance to be purified having undergone the first ion exchange treatment, a distillation treatment of distilling the substance to be purified having undergone the dehydration treatment, a second ion exchange treatment of performing ion exchange treatment on the substance to be purified having undergone the distillation treatment, and an organic component removing treatment of removing an organic component in the substance to be purified having undergone the second ion exchange treatment are performed in this order.

The purification method is not limited to the above, and may adopt an aspect in which a dehydration treatment of dehydrating the substance to be purified, a distillation treatment distilling the substance to be purified having undergone the dehydration treatment, a first ion exchange treatment of performing an ion exchange treatment on the substance to be purified, and an organic component removing treatment of removing an organic component in the substance to be purified having undergone the first ion exchange treatment are performed in this order.

By the first ion exchange treatment, an ion component (for example, a metal component or the like) in the substance to be purified can be removed from the substance to be purified.

In the first ion exchange treatment, first ion exchange means such as an ion exchange resin is used. As the first ion exchange resin, it is possible to use a cation exchange resin or an anion exchange resin provided as a single bed, a cation exchange resin and an anion exchange resin provided as a dual bed, a cation exchange resin and an anion exchange resin provided as a mixed bed, and the like.

As the ion exchange resin, in view of making it more difficult for moisture to be eluted into the substance to be purified from the ion exchange resin, it is preferable to use a dry resin with a small moisture content. Examples of commercial products of such a dry resin include 15JS-HG•DRY (trade name, dry cation exchange resin, moisture: equal to or smaller than 2%) and MSPS2-1•DRY (trade name, mixed bed resin, moisture: equal to or smaller than 10%) manufactured by ORGANO CORPORATION, and the like.

By the dehydration treatment, water in the substance to be purified can be removed. Furthermore, in a case where zeolite (particularly, MOLECULAR SIEVE (trade name) manufactured by Union Showa K. K.), which will be described later, is used in the dehydration treatment, organic substances (for example, olefins) in the substance to be purified can also be removed.

Examples of dehydration means used in the dehydration treatment include a dehydration membrane, a water adsorbent insoluble in the substance to be purified, an aeration purging device using dried inert gas, a heating device, a vacuum heating device, and the like.

In a case where the dehydration membrane is used, membrane dehydration by pervaporation (PV) or vapor permeation (VP) is performed. The dehydration membrane is constituted as a permeable membrane module, for example. As the dehydration membrane, it is possible to use a membrane formed of a polymeric material such as a polyimide-based material, a cellulose-based material, and a polyvinyl alcohol-based material or an inorganic material such as zeolite.

The water adsorbent is used by being added to the substance to be purified. Examples of the water adsorbent include zeolite, diphosphorus pentoxide, silica gel, calcium chloride, sodium sulfate, magnesium sulfate, anhydrous zinc chloride, fuming sulfuric acid, soda lime, and the like.

By the distillation treatment, it is possible to remove impurities eluted from the dehydration membrane, metal components in the substance to be purified that are difficult to remove by the first ion exchange treatment, fine particles (including fine particles of metal components in a case where the metal components are fine particles), and water in the substance to be purified.

The distillation means is constituted with a single-stage distillation device, for example. By the distillation treatment, impurities are concentrated in the distillation device and the like. In order to prevent the leakage of some of the concentrated impurities, the distillation means is preferably provided with means for regularly or constantly discharging a portion of the liquid containing the concentrated impurities to the outside.

By the second ion exchange treatment, it is possible to remove the impurities accumulated in the distillation device in a case where the impurities leak or to remove substances eluted from piping made of stainless steel (SUS) or the like used as a feed line.

Examples of the second ion exchange means include a tower-like container filled with an ion exchange resin and an ion adsorption membrane. Among these, an ion adsorption membrane is preferable because this makes it possible to perform the treatment at a high flow rate. Examples of the ion adsorption membrane include NEOSEPTA (trade name, manufactured by ASTOM Corporation).

Each of the treatments described above is preferably performed under a sealed condition in an inert gas atmosphere in which water is less likely to be mixed into the substance to be purified.

Furthermore, in order to inhibit the mixing of moisture as much as possible, each of the treatments is preferably performed in an inert gas atmosphere in which a dew-point temperature is equal to or lower than −70° C. This is because in the inert gas atmosphere at a temperature equal to or lower than −70° C., the concentration of moisture in a gas phase is equal to or lower than 2 mass ppm, and hence the likelihood that moisture will be mixed into the substance to be purified is reduced.

Examples of the purification step include, in addition to the above treatment, the adsorptive purification treatment for metal components using silicon carbide described in WO2012/043496A, and the like.

By the organic substance removing treatment, it is possible to remove a high-boiling point organic substance, which is contained in the substance to be purified having undergone the distillation treatment and is not easily removed by the distillation treatment, and the like.

The organic substance can be removed by means of an organic substance adsorption member comprising an organic substance adsorption filter which can adsorb the organic substance. Generally, the organic substance adsorption member comprises the aforementioned organic substance adsorption filter and a base material to which the organic substance adsorption filter is fixed.

From the viewpoint of improving the organic substance adsorption performance, it is preferable that the organic substance adsorption filter has the skeleton of an organic substance, which can interact with the organic substance, on the surface thereof (in other words, it is preferable that the surface of the organic substance adsorption filter is modified with the skeleton of an organic substance which can interact with the organic substance). One of the examples of the constitution in which the organic substance adsorption filter has the skeleton of an organic substance which can interact with the organic substance, on the surface thereof include an aspect in which the surface of the base material constituting the organic substance adsorption filter, which will be described later, is provided with the skeleton of an organic substance which can interact with the organic substance.

Examples of the skeleton of an organic substance which can interact with the organic substance include a chemical structure which can react with the organic substance so as to make the organic substance trapped in the organic substance adsorption filter. More specifically, in a case where the substance to be purified contains, as an organic substance, dioctyl phthalate, diisononyl phthalate, dioctyl adipate, or dibutyl phthalate, examples of the skeleton of an organic substance include a benzene ring skeleton. In addition, in a case where the substance to be purified contains ethylene propylene rubber as an organic substance, examples of the skeleton of an organic substance include an alkylene skeleton. Furthermore, in a case where the substance to be purified contains, as an organic substance, long chain n-alkyl alcohol (structural isomer in a case where long chain 1-alkyl alcohol is used as a solvent), examples of the skeleton of an organic substance include an alkyl group.

Examples of the base material (material) constituting the organic substance adsorption filter include cellulose supporting active carbon, diatomite, nylon, polyethylene, polypropylene, polystyrene, a fluorine-containing polymer, and the like.

Furthermore, as an organic impurity removing filter, it is possible to use the filters obtained by fixing active carbon to non-woven cloth that are described in JP2002-273123A and JP2013-150979A.

The organic substance removing treatment is not limited to the aspect in which an organic substance adsorption filter which can adsorb organic substances as described above is used, and may adopt, for example, an aspect in which the organic substance is physically trapped. In many cases, the organic substance having a boiling point equal to or higher than 250° C., which is a relative high boiling point, is coarse (for example, compounds having 8 or more carbon atoms). Therefore, in a case where a filter having a pore size of about 1 nm is used, the organic substance can be physically trapped.

For example, in a case where the substance to be purified contains dioctyl phthalate as an organic substance, the structure of the dioctyl phthalate is larger than 10 Å(=1 nm). Accordingly, in a case where an organic substance removing filter having a pore size of 1 nm is used, the dioctyl phthalate cannot pass through the pores of the filter. That is, by being physically trapped by the filter (in other words, by being removed by the filtering effect), the dioctyl phthalate is removed from the substance to be purified. In this way, for removing an organic substance, not only a chemical interaction but also a physical removing method can be used. Here, in this case, a filter having a pore size equal to or greater than 3 nm is used as "filtering member" which will be described later, and a filter having a pore size less than 3 nm is used as "organic substance removing filter".

In the present specification, 1 Å (angstrom) equals 0.1 nm.

The purification step may further have, for example, a purification treatment V and a purification treatment VI which will be described later. The purification treatment V and the purification treatment VI may be performed at any timing. For example, the purification treatment V and the purification treatment VI may be performed after the purification treatment IV is performed.

The purification treatment V is a filtering treatment in which a metal ion adsorption member is used for the purpose of removing metal ions from the substance to be purified.

The purification treatment VI is a filtering treatment for removing coarse particles.

Hereinafter, the purification treatment V and the purification treatment VI will be described.

One of the examples of means for removing metal ions in the purification treatment V includes filtering in which a metal ion adsorption member comprising a metal ion adsorption filter is used.

The metal ion adsorption member comprises at least one metal ion adsorption filter, and may be constituted with a plurality of metal ion adsorption filters which are stacked according to the intended purification level. Generally, the metal ion adsorption member comprises the metal ion adsorption filter and a base material to which the metal ion adsorption filter is fixed.

The metal ion adsorption filter comprises a function of adsorbing metal ions in the substance to be purified. The metal ion adsorption filter is preferably a filter which can perform ion exchange.

Herein, the metal ions to be adsorbed are not particularly limited but are preferably Fe, Cr, Ni, and Pb because these tend to be the cause of a defect in a semiconductor device.

From the viewpoint of improving the metal ion adsorption performance, it is preferable that the metal ion adsorption filter has an acid group on the surface thereof. Examples of the acid group include a sulfo group, a carboxy group, and the like.

Examples of the base material (material) constituting the metal ion adsorption filter include cellulose, diatomite, nylon, polyethylene, polypropylene, polystyrene, a fluorine-containing polymer, and the like.

One of other examples of means for removing metal ions includes filtering in which a filter constituted with material containing polyimide and/or polyamide imide is used. Examples thereof include filtering in which a metal ion adsorption member comprising a polyimide and/or polyamide imide porous membrane described in JP2016-155121A as a metal ion adsorption filter is used. The polyimide and/or polyamide imide porous membrane used in the filtering may have at least one group selected from the group consisting of a carboxy group, a salt-type carboxy group, and a —NH— bond.

From the viewpoint of solvent resistance, it is preferable to use fluorinated polyimide and/or fluorinated polyamide imide.

One of the examples of filtering means in the purification treatment VI includes an aspect in which filtering is performed using a filtering member comprising a filter having a pore size equal to or smaller than 20 nm. In a case where the substance to be purified passes through such a filter, a particle-like specific component can be removed from the substance to be purified. Examples of "particle-like specific component" include particles of dirt, dust, organic components, inorganic components, and the like contained as impurities in raw materials used at the time of manufacturing the substance to be purified, particles of dirt, dust, organic components, inorganic components, and the like incorporated as contaminants into the substance to be purified at the time of purifying the substance to be purified, and the like. The particle-like specific component corresponds to an object that is finally present as particles in the substance to be purified without being dissolved.

Furthermore, "particle-like specific component" also includes a colloidized metal component containing metal atoms. The metal atoms are not particularly limited. However, in a case where the content of at least one kind of metal atom selected from the group consisting of Na, K, Ca, Fe, Cu, Mg, Mn, Li, Al, Cr, Ni, Zn, and Pb (preferably Fe, Cr, Ni, and Pb) in the substance to be purified is particularly small (for example, in a case where the content of each of the aforementioned metal atoms in the substance to be purified is equal to or smaller than 1,000 mass ppt), the metal component containing these metal atoms is easily colloidized. It is likely that the colloidized metal component will not be easily removed with the aforementioned metal ion adsorption member. Accordingly, in a case where a filter having a pore size equal to or smaller than 20 nm (for example, a microfiltration membrane having a pore size equal to or smaller than 20 nm) is used, the colloidized impurities can be effectively removed.

In many cases, the particle-like specific component has a size that enables the component to be removed by a filter having a pore size equal to or smaller than 20 nm. In other words, in many cases, the particle-like specific components is particles having a diameter equal to or greater than 20 nm. In the present specification, the particle-like specific component is referred to as "coarse particles" in some cases.

Particularly, the pore size of the filter is preferably 1 to 15 nm, and more preferably 1 to 12 nm. In a case where the pore size is equal to or smaller than 15 nm, the particle-like specific component in the form of finer particles can be removed. In a case where the pore size is equal to or greater than 1 nm, the filtering efficiency of the substance to be purified is improved.

The pore size means the minimum size of particles that can be removed by the filter. For example, in a case where the pore size is 20 nm, the filter can remove particles having a diameter equal to or greater than 20 nm.

Examples of the material of the aforementioned filter include 6-nylon, 6,6-nylon, polyethylene, polypropylene, polystyrene, polyimide, polyamide imide, a fluorine-containing polymer, and the like. The polyimide and the polyamide imide may have at least one group selected from the group consisting of a carboxy group, a salt-type carboxy group, and a —NH— bond. From the viewpoint of solvent resistance, the polyimide and the polyamide imide may be fluorinated polyimide and fluorinated polyamide imide.

The filtering member may further comprise a filter having a pore size equal to or greater than 50 nm (for example, a microfiltration membrane for removing fine particles having a pore size equal to or greater than 50 nm). In a case where fine particles are present in the solution in addition to the colloidized impurities, particularly, colloidized specific components containing metal atoms such as iron or aluminum, by filtering the substance to be purified by using a filter having a pore size equal to or greater than 50 nm (for example, a microfiltration membrane for removing fine particles having a pore size equal to or greater than 50 nm) before filtering the substance to be purified by using a filter having a pore size equal to or smaller than 20 nm (for example, a microfiltration membrane having a pore size equal to or smaller than 20 nm), the filtering efficiency of the filter having a pore size equal to or smaller than 20 nm (for example, a microfiltration membrane having a pore size equal to or smaller than 20 nm) is improved, and the coarse particle removing performance is further improved.

Hitherto, as an example of the aforementioned purification step, a case where all of the treatments are performed has been described. However, the present invention is not limited thereto. Each of the treatments may be performed independently, or a plurality of the treatments may be performed in combination. Furthermore, each of the treatments may be performed once or plural times.

As a filter used for filtering, those used for filtering or the like in the related art can be used without particular limitation. Examples of materials constituting the filter include a fluorine-containing polymer such as polytetrafluoroethylene (PTFE), a polyamide-based resin such as nylon, a polyolefin resin (including a high-density polyolefin resin and an ultrahigh molecular-weight polyolefin resin) such as polyethylene and polypropylene (PP), and the like. Among these, a polyamide-based resin, PTFE, and polypropylene (including high-density polypropylene) are preferable. In a case where a filter formed of these materials is used, it is possible to effectively remove the specific component from the substance to be purified.

The lower limit of the critical surface tension of the filter is preferably equal to or higher than 70 mN/m. The upper limit of the critical surface tension of the filter is preferably equal to or lower than 95 mN/m. Particularly, the critical surface tension of the filter is more preferably equal to or higher than 75 mN/m and equal to or lower than 85 mN/m.

The value of the critical surface tension is the nominal value from manufacturers. In a case where a filter having critical surface tension within the above range is used, it is possible to effectively remove the specific component from the substance to be purified.

The filter used for filtering is not particularly limited as long as it has been used for filtering or the like in the related art. Examples of materials constituting the filter include a fluorine-containing polymer such as polytetrafluoroethylene (PTFE), a polyamide-based resin such as nylon, a polyolefin resin (including a high-density polyolefin resin and an ultrahigh molecular-weight polyolefin resin) such as polyethylene and polypropylene (PP), and the like. Among these, polypropylene (including high-density polypropylene) and nylon are preferable.

The pore size of the filter is preferably about 0.001 to 1.0 µm, more preferably about 0.01 to 0.5 µm, and even more preferably about 0.01 to 0.1 µm. In a case where the pore size of the filter is within the above range, it is possible to reliably remove the fine specific component contained in the substance to be purified while inhibiting filter clogging.

At the time of using the filter, different filters may be combined. At this time, filtering carried out using a first filter may be performed once or performed two or more times. In a case where filtering is performed two or more times by using different filters in combination, the filters may be of the same type or different types, but it is preferable that the filters are of different types. Typically, it is preferable that at least one of the pore size or the constituent material varies between the first filter and the second filter.

It is preferable that the pore size for the second filtering and the next filtering is the same as or smaller than the pore size for the first filtering. Furthermore, first filters having different pore sizes within the above range may be combined. As the pore size mentioned herein, the nominal values form filter manufacturers can be referred to. A commercial filter can be selected from various filters provided from, for example, Pall Corporation Japan, Advantec Toyo Kaisha, Ltd., Nihon Entegris KK (former MICRONICS JAPAN CO., LTD.), KITZ MICRO FILTER CORPORATION, or the like. In addition, it is possible to use "P-NYLON FILTER (pore size: 0.02 µm, critical surface tension: 77 mN/m)" made of polyamide; (manufactured by Pall Corporation Japan), "PE•CLEAN FILTER (pore size: 0.02 µm)" made of high-density polyethylene; (manufactured by Pall Corporation Japan), and "PE•CLEAN FILTER (pore size: 0.01 µm)" made of high-density polyethylene; (manufactured by Pall Corporation Japan).

For example, from the viewpoint of inhibiting the increase in the content of particulate metals during the storage of the substance to be purified having undergone purification, provided that an interaction radius in the Hansen solubility parameter (HSP) space derived from the material of the filter used for filtering is R0, and that a radius of a sphere in the Hansen space derived from the organic solvent in the substance to be purified is Ra, it is preferable that the substance to be purified and the material of the filter used for filtering are combined such that the substance to be purified and the filter material have a relationship satisfying a relational expression of (Ra/R0)≤1 and filtering is performed using a filter material satisfying the relational expression, although the combination of the substance to be purified and the filter material is not particularly limited. Ra/R0 is preferably equal to or smaller than 0.98, and more preferably equal to or smaller than 0.95. The lower limit of the Ra/R0 is preferably equal to or greater than 0.5, more preferably equal to or greater than 0.6, and even more preferably equal to or greater than 0.7. In a case where Ra/R0 is within the above range, the formation of a particulate metal or the growth of a particulate metal in the substance to be purified having undergone purification is inhibited even though the substance to be purified having undergone purification is stored for a long period of time, although the mechanism is unclear.

The combination of the filter and the organic solvent is not particularly limited, and examples thereof include those described in US2016/0089622A.

As a second filter, a filter formed of the same material as the aforementioned first filter can be used. Furthermore, a filter having the same pore size as the aforementioned first filter can be used. In a case where a filter having a pore size smaller than that of the first filter is used as the second filter, a ratio between the pore size of the second filter and the pore size of the first filter (pore size of second filter/pore size of first filter) is preferably 0.01 to 0.99, more preferably 0.1 to 0.9, and even more preferably 0.2 to 0.9. In a case where the pore size of the second filter is within the above range, the fine specific component in the substance to be purified is more reliably removed.

It is preferable that the filter to be used is washed before filtering the substance to be purified. The washing solution used for washing is not particularly limited. In a case where the organic solvent contained in the substance to be purified, the chemical liquid itself, or a solution obtained by diluting the chemical liquid is used as the washing solution, the substance to be purified having undergone purification in which the content of the specific component is further reduced is obtained.

As the washing solution, water, an organic solvent, and the like can be used without particular limitation. The organic solvent may be an organic solvent that the chemical liquid can contain, such as alkylene glycol monoalkyl ether carboxylate, alkylene glycol monoalkyl ether, a lactic acid alkyl ester, alkoxyalkyl propionate, cyclic lactone (preferably having 4 to 10 carbon atoms), a monoketone compound (preferably having 4 to 10 carbon atoms) which may have a ring, alkylene carbonate, alkoxyalkyl acetate, or alkyl pyruvate.

More specifically, examples of the washing solution include propylene glycol monomethyl ether, propylene glycol monomethyl ether acetate, dimethylsulfoxide, n-methylpyrrolidone, diethylene glycol, ethylene glycol, dipropylene glycol, propylene glycol, ethylene carbonate, propylene carbonate, sulfolane, cyclohexane, cyclohexanone, cycloheptanone, cyclopentanone, 2-heptanone, γ-butyrolactone, a mixture of these, and the like.

In a case where filtering is performed, the upper limit of the temperature at the time of filtering is preferably equal to or lower than room temperature (25° C.), more preferably equal to or lower than 23° C., and even more preferably equal to or lower than 20° C. The lower limit of the temperature at the time of filtering is preferably equal to or higher than 0° C., more preferably equal to or higher than 5° C., and even more preferably equal to or higher than 10° C.

By the filtering, the particulate specific component can be removed. In a case where the filtering is performed at the above temperature, the content of particulate specific component in the substance to be purified is reduced, and hence the filtering is more efficiently performed.

Particularly, from the viewpoint of adjusting the content of metal components in the substance to be purified, it is preferable that filtering is performed at the above temperature. It is considered that many of the metal components may be present in a particulate colloidal state, although the mechanism is unclear. In a case where filtering is performed at the above temperature, some of the metal components floating in the form of colloid are aggregated, and hence the aggregated metal components are efficiently removed by the filtering. It is considered that for this reason, the content of the metal components can be easily adjusted to be the desired amount.

The filtering pressure affects the filtering accuracy. Therefore, it is preferable that the pulsation of pressure at the time of filtering is as low as possible.

In a case where two or more filters are used, the differential pressure before and after the substance to be purified passes through each of the filters (hereinafter, referred to as "differential pressure of filtering" as well) is not particularly limited, but is preferably equal to or lower than 250 kPa and more preferably equal to or lower than 200 kPa. The lower limit thereof is not particularly limited, but is preferably equal to or higher than 50 kPa. In a case where the differential pressure of filtering is equal to or lower than 250 kPa, it is possible to prevent an excessive pressure from being applied to the filter, and hence the amount of substances eluted into the substance to be purified from the filter expected to be reduced.

In the purification of the substance to be purified, the filtering speed is not particularly limited. However, the filtering speed is preferably equal to or higher than 1.0 L/min/m$^2$, more preferably equal to or higher than 0.75 L/min/m$^2$, and even more preferably equal to or higher than 0.6 L/min/m$^2$.

For the filter, an endurable differential pressure for assuring the filter performance (assuring that the filter will not be broken) is set. In a case where the endurable differential pressure is high, by increasing the filtering pressure, the filtering speed can be increased. That is, it is preferable that the upper limit of the filtering speed is generally equal to or lower than 10.0 L/min/m² although the upper limit usually depends on the endurable differential pressure of the filter.

In the purification of the substance to be purified, from the viewpoint of obtaining further improved effects of the present invention, the filtering pressure is preferably equal to or higher than 0.001 MPa and equal to or lower than 1.0 MPa, more preferably equal to or higher than 0.003 MPa and equal to or lower than 0.5 MPa, and particularly preferably equal to or higher than 0.005 MPa and equal to or lower than 0.3 MPa.

Particularly, in a case where a filter having a small pore size is used, by increasing the filtering pressure, it is possible to efficiently reduce the amount of particle-like foreign substances or impurities dissolved in the solution. In a case where a filter having a pore size smaller than 20 nm is used, the filtering pressure is particularly preferably equal to or higher than 0.005 MPa and equal to or lower than 0.3 MPa.

The smaller the pore size of the filtration filter, the lower the filtering speed. However, for example, in a case where a plurality of filters equipped with the same type of filtration filter are connected to each other in parallel, the filtering area is enlarged, and the filtering pressure is reduced. Therefore, in this way, the reduction in the filtering speed can be compensated.

The purification step may further have an electricity removing step of removing electricity from the substance to be purified (and/or the substance to be purified having undergone purification). In a case where the electricity is removed, the charge potential of substance to be purified can be reduced.

As the electricity removing method, known electricity removing methods can be used without particular limitation. Examples of the electricity removing method include a method for bringing the purified solution or the like into contact with a conductive material.

The contact time for which the purified substance or the like is brought into contact with a conductive material is preferably 0.001 to 60 seconds, more preferably 0.001 to 1 second, and even more preferably 0.01 to 0.1 seconds. Examples of the conductive material include stainless steel, gold, platinum, diamond, glassy carbon, and the like.

Examples of the method for bringing the purified substance or the like into contact with a conductive material include a method for disposing a grounded mesh formed of a conductive material in the interior of a pipe line and passing the purified substance or the like through the mesh, and the like.

(Other Steps)

The electricity removing step may be performed not only in the purification step but also at the time of filling a container with the chemical liquid manufactured by the present manufacturing method. It is particularly preferable that the electricity removing step is performed before the container is filled with the chemical liquid. In a case where the electricity removing step is performed at this timing, it is possible to inhibit the specific component derived from the container or the like from being mixed into the purified substance or the like.

[Step W2]

The step W2 is the same as the aspect of the step W, except that in the step W described above, the substance to be purified having undergone purification is used instead of the chemical liquid. The aspect of a2 liquid is the same as the aspect of a liquid, except that instead of the chemical liquid, the substance to be purified having undergone purification is used as a2 liquid. Therefore, the step W2 will not be described.

[Step A2]

The step A2 is the same the aspect of the step A, except that in the step A described above, the substance to be purified having undergone purification is used instead of the chemical liquid. The aspects of b2 liquid and c2 liquid are the same as the aspects of b liquid and c liquid, except that instead of the chemical liquid, the substance to be purified having undergone purification is used as b2 liquid and c2 liquid. Therefore, the step A2 will not be described.

[Step B2]

The step B2 is the same as the aspect of the step B described above. Therefore, the step B2 will not be described.

[Step C2]

The step C2 is the same as the aspect of the step C described above. Therefore, the step C2 will not be described.

[Step E]

The step E is a step of determining the substance to be purified having undergone purification as a new substance to be purified and repeating the step P, the step W2, the step A2, the step B2, and the step C2 in this order in a case where the content of the specific component is greater than the standard value in the step C2.

In a case where the content of the specific component is greater than the standard value in the step C2, the substance to be purified having undergone purification (for example, the substance to be purified having undergone purification of the manufacturing lot) is determined as a new substance to be purified, purified again, and inspected again. The present step E is repeatedly performed until the content of the specific component in the substance to be purified having undergone purification becomes equal to or smaller than the standard value.

[Step Z]

The substance to be purified having undergone purification in which the content of the specific component is equal to or smaller than the standard value in the step C2 or the step E is determined as being adequate and adopted as a chemical liquid in the step Z.

[Other Steps]

<Specific Component Determination Step>

The manufacturing method of a chemical liquid may further have a specific component determination step between the step P and the step W2 or between the step W2 and the step A2. The specific component determination step includes the following step W4, step A4, step B4, and step C4 that are performed in this order.

(Step W4)

The step W4 is a step of preparing a third container having a liquid contact portion of which at least a portion is formed of the corrosion-resistance material described above, adopting a portion of the substance to be purified having undergone purification as k liquid, and washing at least a portion of the liquid contact portion of the third container by using k liquid.

The third container used in the present step is not particularly limited as long as at least a portion of the liquid contact portion thereof is formed of the corrosion-resistance material, and is the same as the aspect of the first container used in the step W.

The method for washing at least a portion of the liquid contact portion of the third container by using k liquid is not particularly limited, and is the same as the aspect described above as the method for washing at least a portion of the liquid contact portion of the first container by using k liquid.

(Step A4)

The step A4 is a step of adopting a portion of the substance to be purified having undergone purification as 1 liquid and performing concentration of 1 liquid by using the washed third container so as to obtain three or more kinds of m liquids having different factors of concentration. The concentration is performed under at least one kind of inert gas selected from the group consisting of an Ar gas, a He gas, and a $N_2$ gas or under reduced pressure. Furthermore, the step W4 and the step A4 are performed in a clean room having cleanliness equal to or higher than class 4 specified in the International Standard ISO14644-1:2015 established by the International Organization for Standardization.

The method for performing concentration of 1 liquid is not particularly limited, and is the same as the aspect described above as the method for performing concentration of b liquid in the step A.

In the present step, three or more kinds of m liquids having different factors of concentration are obtained. The factor of concentration of each of m liquids is not particularly limited. However, it is preferable that the difference in the factor of concentration among the liquids is about several fold to 100 fold. For example, a combination of a 100× concentrated liquid, a 300× concentrated liquid, a 500× concentrated liquid, a 1,000× concentrated liquid, and the like is preferable.

(Step B4)

The step B4 is a step of measuring the content of an organic substance, in which m/Z is 300 to 1,000, in m liquids by at least one kind of measurement method selected from the group consisting of high-performance liquid chromatography mass spectrometry and gas chromatography mass spectrometry.

(Step C4)

The step C4 is a step in which in a case where one kind of organic substance is commonly detected from all of three or more kinds of m liquids, one kind of the organic substance is determined as the specific component, and in a case where two or more kinds of organic substances are commonly detected from all of three or more kinds of m liquids, linear regression is performed on the factors of concentration and the content of each of two or more kinds of the organic substances and on the factors of concentration and the total content of any two or more kinds of organic substances selected from the group consisting of two or more kinds of the organic substances, and an organic substance or a combination of organic substances from which a maximum (positive) coefficient of correlation is obtained is determined as the specific component.

The organic substance commonly detected from all of three or more kinds of m liquids is more likely to be a component contained in the substance to be purified having undergone purification. In other words, the organic substance is less likely to be an impurity intermixed at the stage of preparing k liquid. Consequently, in a case where such an organic substance is determined as the specific component, the defect inhibition performance of the substance to be purified having undergone purification can be more accurately evaluated.

In a case where two or more kinds of organic substances are commonly detected from all of three or more kinds of m liquids, by performing linear regression on the content thereof and the factors of concentration and on the total content of any two or more kinds of organic substances selected from the group consisting of two or more kinds of the organic substances and the factors of concentration and determining an organic substance or a combination of organic substances from which a maximum coefficient of correlation is obtained as the specific component, the defect inhibition performance of the substance to be purified having undergone purification can be more accurately measured.

In a case where two or more kinds of organic substances are commonly detected from all of three or more kinds of m liquids, and the same coefficient of correlation is obtained from the contents thereof, the content of a combination thereof, and factors of concentration, two or more kinds of organic substances or a combination thereof may be determined as the specific component.

<Standard Value Determination Step>

The manufacturing method of a chemical liquid according to the present embodiment may further have a standard value determination step that is performed at a point in time when the specific component determination step has finished but the step C4 is not yet started. The aspect of the standard value determination step is the same as the aspect of the standard value determination step described above regarding the quality inspection method for a chemical liquid, except for the substance to be purified having undergone purification is used instead of the chemical liquid. Therefore, the standard value determination step will not be described.

By the manufacturing method of a chemical liquid according to the present embodiment, a chemical liquid having excellent defect inhibition performance is simply obtained.

[Manufacturing Method of Chemical Liquid Storage Body]

The manufacturing method of a chemical liquid storage body according to an embodiment of the present invention has a filling step of filling a second container with the chemical liquid manufactured by the manufacturing method described above so as to obtain a chemical liquid storage body having the second container and the chemical liquid stored in the second container.

As the method for filling second container with the chemical liquid, known filling methods can be used without particular limitation.

[Second Container]

As the second container used in the chemical liquid storage body, known containers can be used without particular limitation.

As the second container, a container is preferable which has high internal cleanliness and hardly causes elution of the specific component into the stored chemical liquid.

Examples of the second container include a "CLEAN BOTTLE" series manufactured by AICELLO CORPORATION, "PURE BOTTLE" manufactured by KODAMA PLASTICS Co., Ltd., and the like, but the container is not limited to these. It is preferable that the liquid contact portion of this container is formed of a nonmetallic material.

As the nonmetallic material, at least one kind of material selected from the group consisting of a polyethylene resin, a polypropylene resin, a polyethylene-polypropylene resin, a polytetrafluoroethylene resin (PTFE), a polytetrafluoroethylene-perfluoroalkyl vinyl ether copolymer (PFA), a polytetrafluoroethylene-hexafluoropropylene copolymer resin (FEP), a polytetrafluoroethylene-ethylene copolymer resin (ETFE), a chlorotrifluoro ethylene-ethylene copolymer resin (ECTFE), a vinylidene fluoride resin (PVDF), a chlorotrifluoroethylene copolymer resin (PCTFE), and a vinyl fluoride resin (PVF) is more preferable.

Particularly, in a case where a container in which the liquid contact portion is formed of a fluororesin, the occurrence of a problem such as elution of an ethylene or propylene oligomer can be further inhibited than in a case where a container in which the liquid contact portion is formed of a polyethylene resin, a polypropylene resin, or a polyethylene-polypropylene resin is used.

Specific examples of the container in which the inner wall is formed of a fluororesin include FluoroPure PFA composite drum manufactured by Entegris, Inc., and the like. Furthermore, it is possible to use the containers described on p. 4 in JP1991-502677A (JP-H03-502677A), p. 3 in WO2004/016526A, p. 9 and p. 16 in WO99/046309A, and the like.

In a case where the nonmetallic material is used for the liquid contact portion, it is preferable to inhibit the elution of the organic component in the nonmetallic material into the solution.

For the liquid contact portion of the second container, in addition to the aforementioned nonmetallic material, quartz or a metallic material (more preferably an electropolished metallic material, in other words, a metallic material finished up with electropolishing) is also preferably used.

It is preferable that the metallic material (particularly, the metallic material used for manufacturing the electropolished metallic material) contains chromium in an amount greater than 25% by mass with respect to the total mass of the metallic material, and examples of such a material include stainless steel.

The content of chromium in the metallic material with respect to the total mass of the metallic material is more preferably equal to or greater than 30% by mass. The upper limit of the content of chromium is not particularly limited, but is preferably equal to or smaller than 90% by mass in general.

It is preferable that the interior of the second container is washed before the second container is filled with the chemical liquid. As a washing solution used for washing, the chemical liquid or a liquid obtained by diluting the chemical liquid is preferable. After being manufactured, the chemical liquid may be bottled using the second container such as a gallon bottle or a quart bottle, transported, and stored. The gallon bottle may be formed of a glass material or other materials.

In order to prevent the change of the components in the solution during storage, purging may be performed in the interior of the container by using an inert gas (nitrogen, argon, or the like) having a purity equal to or higher than 99.99995% by volume. Particularly, a gas with small moisture content is preferable. The temperature at the time of transport and storage may be room temperature. However, in order to prevent alteration, the temperature may be controlled within a range of −20° C. to 20° C.

As the second container, it is also possible to use the same container as the first container used for concentrating the liquid to be inspected described above.

[Use of Chemical Liquid]

The chemical liquid having undergone quality inspection by the present quality inspection method is used for manufacturing a semiconductor substrate. Specifically, in a semiconductor substrate manufacturing process (particularly, a semiconductor manufacturing process at a node equal to or smaller than 10 nm) including a lithography step, an etching step, an ion implantation step, a peeling step, and the like, the chemical liquid is used for treating an organic substance after each step is finished or before the next step is started. Specifically, the chemical liquid is suitably used as a prewet solution, a developer, a rinsing solution, a peeling solution, and the like. For example, the chemical liquid can also be used for rinsing at the time of edge line of semiconductor substrates having been coated with resist. Among these, as the chemical liquid, a prewet solution is preferable. In other words, the chemical liquid is preferably used for pre-wetting.

Furthermore, the chemical liquid can also be used as a diluent of a resin contained in a resist composition. That is, the chemical liquid can also be used as a solvent contained in a resist composition.

The chemical liquid can also be used for other uses in addition to the manufacturing of semiconductor substrates. The chemical liquid can be used as a developer or a rinsing solution of polyimide, a resist for a sensor, a resist for a lens, and the like.

In addition, the chemical liquid can also be used as a solvent for medical uses or for washing. Particularly, the chemical liquid can be suitably used for washing containers, piping, substrates (for example, a wafer and glass), and the like.

EXAMPLES

Hereinafter, the present invention will be more specifically described based on examples. The materials, the amount and proportion of the materials used, the details of treatments, the procedure of treatments, and the like shown in the following examples can be appropriately modified as long as the gist of the present invention is maintained. Accordingly, the scope of the present invention is not limited to the following examples.

Test Example 1: Preparation of Chemical Liquid

By the following method, chemical liquids 1-1 to 1-4 which contained an organic solvent shown in Table 1 and purified by different methods were prepared.

[Chemical Liquid 1-1]

A substance to be purified containing an organic solvent described in Table 1 was distilled and then purified by passing through the following filters in the following order, thereby obtaining a chemical liquid 1-1. That is, the substance to be purified was subjected to multistage filtration using a first filter: filter made of polytetrafluoroethylene (PTFE) having a pore size of 15 nm, a second filter: 12 nm PTFE manufactured by Entegris, Inc. (filter made of PTFE having a pore size of 12 nm), and a third filter: 10 nm IEX PTFE manufactured by Entegris, Inc. (filter having a pore size of 10 nm constituted with a base material made of PTFE having a sulfo group on the surface thereof), thereby manufacturing the chemical liquid. This method is called purification method "A".

[Chemical Liquid 1-2]

A substance to be purified containing an organic solvent was distilled and then subjected to multistage filtration using a first filter: 12 nm PTFE manufactured by Entegris, Inc. (filter having a pore size of 12 nm made of PTFE) and a second filter: 10 nm IEX PTFE manufactured by Entegris, Inc. (filter having a pore size of 10 nm constituted with a base material made of PTFE having a sulfo group on the surface thereof), thereby manufacturing a chemical liquid 1-2. This method is called purification method "B".

[Chemical Liquid 1-3]

A substance to be purified containing an organic solvent was distilled and then filtered using only 10 nm IEX PTFE manufactured by Entegris, Inc. (filter having a pore size of 10 nm constituted with a base material made of PTFE having a sulfo group on the surface thereof), thereby manufacturing a chemical liquid 1-3. This method is called purification method "C".

[Chemical Liquid 1-4]

A substance to be purified containing nBA was distilled and then filtered using only PTFE (filter having a pore size of 15 nm made of PTFE), thereby manufacturing a chemical liquid 1-4. This method is called purification method "D".

Each of the substances to be purified was purified in a clean room (class 1) by using a "high-purity grade" organic solvent described in Table 1 having purity equal to or higher than 99% by mass.

The organic solvent contained in the used substances to be purified and the second container storing the manufactured chemical liquid are shown in Table 1.

Test Example 1: Determination of Specific Component

A chemical liquid prepared by the same method as that used for preparing the chemical liquid 1-1 was stored in a clean bottle made of perfluoroalkoxyalkane (PFA), and the bottle was sealed by putting a lid thereon, thereby obtaining a chemical liquid storage body.

Then, the chemical liquid storage body was opened in a clean room of class 1, and the chemical liquid was concentrated under reduced pressure by using a Soxhlet extractor. At a point in time when the factor of concentration became 100×, 300×, 500×, and 1,000×, the chemical liquid was extracted, thereby preparing measurement samples.

For the concentration of the chemical liquid, a glass container was used which was subjected to acid washing by using diluted HF and $HNO_3$, then washed with ultrapure water and with the chemical liquid, and then dried.

Thereafter, for each of the measurement samples, by using LC/MS and GC/MS, the content of all the compounds in which m/Z was 300 to 1,000 (value of integral of signal intensity in a mass chromatogram) was analyzed. As the measurement results, the contents of detected components (value of integral of signal intensity: relative quantity) and the total content of a combination of the components (sum of the values of integral of signal intensity: relative quantity) were plotted on the ordinate, and the factors of concentration were plotted on the abscissa.

Subsequently, a component or a combination thereof from which a maximum coefficient of correlation was obtained through linear regression was searched for, and the combination of components described in Table 1 was determined as a specific component in each example.

Specific component A: a combination of compounds in which m/Z=300 to 1,000 including the compounds of Formulae (1) to (7) ("Content of specific component A" is the total content of the above compounds)

Specific component B: a combination of compounds of Formulae (1) to (7) ("Content of specific component B" is the total content of the compounds of Formulae (1) to (7))

Test Example 1: Preparation of Concentrated Liquid

By using a Soxhlet extractor, the chemical liquids 1-1 to 1-4 were concentrated under reduced pressure such that the factor of concentration set for each of the measurement methods, which will be described later, was achieved, and the concentrated liquids were collected in a nitrogen atmosphere. This operation was performed in a class 1 clean room.

(Washing of Container)

The fourth container used for the concentration of the chemical liquid was made of glass. The fourth container was subjected to acid washing by using diluted HF and $HNO_3$, then washed with ultrapure water and then with each of the chemical liquids 1-1 to 1-4 (specific washing solutions), and then dried.

<Measurement of $P_1$ and $P_2$>

By using a time-of-flight secondary ion mass spectrometer (manufactured by IONTOF GmbH, trade name: "TOF-SIMS5"), $P_1$ and $P_2$ were measured under the following conditions.

Primary ion: $Bi_3^{2+}$
Primary ion acceleration voltage: 25 kV
Measurement area: 500 μm×500 μm
Measurement temperature: equal to or lower than −100° C.

For etching, Ar-GCIB (Ar gas cluster ion beam) was radiated. Furthermore, as a primary ion source, $Bi^{3+}$ was radiated, and the obtained secondary ion was analyzed using time-of-flight type mass spectrometer, thereby obtaining a spectrum.

Ar-GCIB injection pressure: 3 MPa
Measurement surface: 150 μm×150 μm
Measurement mode: high mass resolution <Elution Test>

A portion of each of the chemical liquids was adopted as an immersion liquid, and the washed first container was immersed for 24 hours in each of the immersion liquids at a liquid temperature of 25° C., under the condition that a mass ratio (g/g) of the mass of the washed first container to the mass of the immersion liquid became 1.0. The increase in the content of fluoride ions contained in the immersion liquid before and after the immersion was measured by the following method. The results are shown in Table 1. In Table 1, "<" means that the measurement result is less than the numerical value described in the table. Furthermore, in Table 1, "ppm" in the columns of "Fluoride ion" and "Metal component" means "mass ppm".

(Fluoride Ion)

For the measurement, HIC-SP suppressor ion chromatograph manufactured by Shimadzu Corporation was used. The measurement conditions are as below.

Measurement Conditions

Used column: ion exchange resin (inner diameter: 4.0 mm, length: 25 cm)

Mobile phase: sodium hydrogen carbonate solution (1.7 mmol/L)-sodium carbonate solution (1.8 mmol/L), flow rate: 1.5 mL/min Amount of sample injected: 25 μL
Column temperature: 40° C.
Suppressor: electrodialysis type detector: electric conductivity detector (30° C.)

(Metal Component)

For the measurement, Agilent 8800 triple quadrupole ICP-MS (for semiconductor analysis, option #200) was used. Based on the measurement results, the content of the metal particles and the content of the metal ions were determined.

Measurement Conditions

As a sample introduction system, a quartz torch, a coaxial perfluoroalkoxyalkane (PFA) nebulizer (for self-suction), and a platinum interface cone were used. The measurement parameters of cool plasma conditions are as below.

Output of Radio Frequency (RF) (W): 600
Flow rate of carrier gas (L/min): 0.7
Flow rate of makeup gas (L/min): 1
Sampling depth (mm): 18

Test Example 1: Measurement

By the following method, the content of the specific component in each of the obtained concentrated liquids was measured.

[LC/MS]

As samples, 1,000× concentrated liquids were used. The content of the specific component was measured using a liquid chromatography mass spectrometer (trade name: "UPLC-H-Class, Xevo G2-XS QTof", manufactured by Thermo Fisher Scientific K. K., adopting the following measurement conditions) as LC/MS. As the specific component, compounds in which m/XZ was 300 to 1,000 (including the compounds represented by Formulae (1) to (7)) measured by the method described above were adopted. The results were expressed as an exponent (relative quantity) determined on the premise that the signal intensity of the concentrated liquid of the chemical liquid 1-1 is 1.0.

(Measurement Conditions)
LC Conditions
Device: UPLC-H-Class
Column: ACQUITY UPLC C8 1.7 µm, 2.1×100 mm
Column temperature: 40° C.
Mobile phase: A: 0.1% formic acid, B: 0.1% formic acid-containing MeOH
Flow rate: 0.5 mL/min
Injection amount: 2 µL
MS Conditions
Device: Xevo G2-XS Q-Tof
Ionization mode: ESI positive/negative
Capillary voltage: 1.0 kV/2.5 kV
Desolvation gas: 1,000 L/hr, 500° C.
Cone gas: 50 L/hr
Cone voltage: 40 V (offset 80 V)
Collision energy: 2 eV
Measurement range: m/z 100 to 1,000
Measurement mode: MS Sensitivity Mode (resolution/30,000)

[GC/MS]

As samples, 1,000× concentrated liquids were used. The content of an organic impurity having a boiling point equal to or higher than 200° C. in each of the measurement samples was measured using a gas chromatography mass spectrometer (trade name "GCMS-2020", manufactured by Shimadzu Corporation, adopting the following measurement conditions). As the specific component, compounds in which m/Z was 300 to 1,000 (including the compounds represented by Formulae (1) to (7)) measured by the method described above were adopted. The results were expressed as an exponent (relative quantity) determined on the premise that the signal intensity of the concentrated liquid of the chemical liquid 1-1 is 1.0.

(Measurement Conditions)
Capillary column:
InertCap 5MS/NP 0.25 mm I. D.×30 m df=0.25 µm
Sample introduction method: split 75 kPa constant pressure
Vaporizing chamber temperature: 250° C.
Column oven temperature: 80° C. (2 min)–500° C. (13 min) heating rate 15° C./min
Carrier gas: helium
Septum purge flow rate: 5 mL/min
Split ratio: 25:1
Interface temperature: 250° C.
Ion source temperature: 200° C.
Measurement mode: Scan m/z=85 to 500
Amount of sample introduced: 1 µL

[DI-MS]

As samples, 1,000,000× concentrated liquids were used. The content of an organic impurity having a boiling point equal to or higher than 200° C. in each of the measurement samples was measured using a gas chromatography mass spectrometer (trade name "GCMS-QP2010 Ultra", manufactured by Shimadzu Corporation, adopting the following measurement conditions). As the specific component, compounds represented by Formulae (1) to (7) were adopted, and the total amount thereof was measured. The results were expressed as an exponent (relative quantity) determined on the premise that the signal intensity of the concentrated liquid of the chemical liquid 1-1 is 1.0.

(Measurement Conditions)
Sample introduction method: direct introduction (DI without using GC portion)
Ion source temperature: 230° C.
Interface temperature: 240° C.
Ionization mode: SEI
Measurement mode: Scan m/z=30 to 1,000

[NMR]

As samples, 10,000× concentrated liquids were used. As the specific component, the compounds represented by Formulae (1) to (7) were adopted, and the total amount thereof was measured. The results are expressed as an absolute quantity (mass ppb).

(Measurement Conditions)
Device: AL400 model manufactured by JEOL Ltd.
Nucleus for measurement: $^1$H
Solvent: CDCl3

[ICP-MS]

As samples, 100× concentrated liquids were used. The content of metal atoms in each of the measurement samples was measured using an ICP-MS mass spectrometer (trade name: "Agilent 8800", manufactured by Agilent Technologies, Inc, adopting the following measurement conditions). As the specific component, the total content of Ag, Al, As, Au, Ba, Ca, Cd, Co, Cr, Cu, Fe, Ga, Ge, K, Li, Mg, Mn, Mo, Na, Nb, Ni, Pb, Sb, Sn, Sr, Ta, Th, Ti, Tl, V, W, Zn, Zr, and Mo were adopted, and the total amount thereof was measured. The result was expressed as an absolute quantity (mass ppt).

(Measurement conditions)
Measurement device: Agilent 8800
RF output (W): 600
Flow rate of carrier gas (L/min): 0.7
Flow rate of makeup gas (L/min): 1
Sampling position (mm): 18

[Evaluation of Defect Inhibition Performance]

First, a silicon oxide film substrate having a diameter of about 300 mm (12 inches) was prepared.

Then, by using a wafer surface inspection device (SP-5; manufactured by KLA-Tencor Corporation), the number of defects having a diameter equal to or greater than 17 nm present on the substrate was counted (the counted number was adopted as an initial value).

Thereafter, by using "CLEAN TRACK LITHIUS (trade name)" manufactured by Tokyo Electron Limited, the substrate was spin-coated with each of the chemical liquids at 1,500 rpm and then spin-dried.

Subsequently, by using the device (SP-5), the number of defects present on the substrate coated with the chemical liquid was counted (the counted number was adopted as a counted value). Then, a difference between the initial value and the counted value (initial value-counted value) was calculated and adopted as total number of defects. The total number of defects represents the defect inhibition performance of a chemical liquid. It is determined that the smaller the total number of defects, the better the defect inhibition performance.

Furthermore, the coordinates of the defects were read using a full automatic defect review device "SEMVision G6" manufactured by Applied Materials, Inc., the composition of each of the defects was analyzed by energy dispersive X-ray spectroscopy, and the number of defects containing metal atoms was counted as the number of metal defects. The number of metal defects represents the defect inhibition performance of a chemical liquid. It is determined that the smaller the number of metal defects, the better the defect inhibition performance. In Table 1, the unit of the total number of defects and the number of metal defects is number/12 inchWf (number of defects on a 12-inch wafer, 12 inches approximately equal 300 mm).

Test Example 1: Checking results

For the chemical liquids 1-1 to 1-4 among which the content of the specific component varied, a coefficient of correlation was determined by performing linear regression on the measured content of the specific component (LC/MS, GC/MS, DI-MS, and NMR) and the total number of defects, and another coefficient of correlation was determined by performing linear regression on the measured content of the specific component (ICP-MS) and the number of metal defects. The results are shown in Table 1. The results show that the closer the coefficient of correlation to 1, the higher the obtained positive coefficient of correlation.

Test Examples 2 to 22

In each of Test Examples 2 to 22, each of substances to be purified containing an organic solvent described in Table 1 was purified by the purification methods A to D described above and then stored in the second container described in Table 1, thereby manufacturing a chemical liquid storage body. In Table 1, regarding the chemical liquid denoted by "(first number)-(second number)", "(first number)" corresponds to the number of the test example, and "(second number)" corresponds to the purification method. That is, regarding (second number), 1 corresponds to A, 2 corresponds to B, 3 corresponds to C, and 4 corresponds to D.

Then, the chemical liquid storage body was opened in a class 1 clean room, and the chemical liquid was concentrated by the method described in Table 1 by using the fourth container having a liquid contact portion formed of a material described in Table 1.

The physical properties of the liquid contact portion of the fourth container used and the results of the elution test are described in Table 1.

In Table 1, "Electropolished SUS" means that the container had a liquid contact portion formed of electropolished stainless steel, "PTFE container" means that the container had a liquid contact portion formed of polytetrafluoroethylene, "Washed with water" means that the container was washed with ultrapure water without being subjected to acid washing, "-" means that the corresponding treatment was not performed, "In the atmosphere" means that the treatment was not performed in a clean room, "Heating concentration $N_2$" means that the chemical liquid was concentrated by heating in a $N_2$ gas environment, and "Heating concentration Ar" means that the chemical liquid was concentrated by heating in an Ar gas environment.

For the concentrated liquid, the content of the specific component was measured by the same method as in Test Example 1 and compared with the defect inhibition performance measured by the same method as in Test Example 1. In a case where the content of the specific component was expressed as a relative value, the value was expressed as an exponent determined on the premise that the specific signal intensity of the concentrated liquid purified by the purification method A (chemical liquid denoted by "(first number)–1") is 1.0.

From the above results, it was understood that in Test Examples 1 to 22, there is a strong correlation between the measured content of the specific component and the number of defects (defect inhibition performance) measured by the defect inspection device.

From the results shown in Table 1, it was understood that in a case where linear regression was performed on the content of the specific component and the number of defects (defect inhibition performance) measured by the defect inspection device, the obtained coefficient of correlation was higher in Test Example 1 performed in a predetermined clean room than in Test Example 2.

From the results shown in Table 1, it was understood that in a case where PGME, PGEE, PGMEA, EL, MPM, CyPe, CyHe, γBL, DIAE, MIBC, or a mixture of PGMEA and PGME (volume ratio=7:3) was used as an organic solvent, by the linear regression performed on the content of the specific component and the number of defects (defect inhibition performance) measured by the defect inspection device, a higher coefficient of correlation was obtained.

From the results shown in Table 1, it was understood that in a case where linear regression was performed on the content of the specific component (particularly, the specific organic substance) and the number of defects (defect inhibition performance) measured by the defect inspection device, the obtained coefficient of correlation was higher in Test Example 10, in which the liquid contact portion of the fourth container was formed of glass, than in Test Example 17 in which the liquid contact portion of the fourth container was formed of PTFE.

It was understood that in a case where linear regression was performed on the content of the specific component (particularly, the specific organic substance) and the number of defects (defect inhibition performance) measured by the defect inspection device, the obtained coefficient of correlation was higher in Test Example 10, in which the liquid contact portion of the second container in the chemical liquid storage body was formed of a fluorine-containing polymer, than in Test Example 18 in which the liquid contact portion of the second container was formed of electropolished stainless steel.

From the results shown in Table 1, it was understood that in a case where linear regression was performed on the content of the specific component (particularly, the specific organic substance) and the number of defects (defect inhibition performance) measured by the defect inspection device, the obtained coefficient of correlation was higher in Test Example 10, in which acid washing was performed, than in Test Example 21 in which acid washing was not performed.

From the results shown in Table 1, it was understood that in a case where linear regression was performed on the content of the specific component (particularly, the specific organic substance) and the number of defects (defect inhibition performance) measured by the defect inspection device, the obtained coefficient of correlation was higher in Test Example 10, in which ultrasonic washing was performed, than in Test Example 22 in which ultrasonic washing was not performed.

TABLE 1

| TABLE 1-1-1 | No. | Chemical liquid Organic solvent | Second container | Fourth container Material of liquid contact portion | Step W4 Acid washing | Ultrasonic washing | Specific washing solution | Drying | Liquid contact portion $P_1$ $P_2$ | Result of elution test Fluoride ion | Metal component |
|---|---|---|---|---|---|---|---|---|---|---|---|
| Test Example 1 | 1-1<br>1-2<br>1-3<br>1-4 | nBA | PFA clean bottle | Glass | Diluted HF, HNO3 → washed with water | Performed | Performed | Performed | | <1 ppm | <1 ppm |
| Test Example 2 | 2-1<br>2-2<br>2-3<br>2-4 | nBA | PFA clean bottle | Glass | Diluted HF, HNO3 → washed with water | Performed | Performed | Performed | | <1 ppm | <1 ppm |
| Test Example 3 | 3-1<br>3-2<br>3-3<br>3-4 | PGME | PFA clean bottle | Glass | Diluted HF, HNO3 → washed with water | Performed | Performed | Performed | | <1 ppm | <1 ppm |
| Test Example 4 | 4-1<br>4-2<br>4-3<br>4-4 | PGEE | PFA clean bottle | Glass | Diluted HF, HNO3 → washed with water | Performed | Performed | Performed | | <1 ppm | <1 ppm |
| Test Example 5 | 5-1<br>5-2<br>5-3<br>5-4 | PGPE | PFA clean bottle | Glass | Diluted HF, HNO3 → washed with water | Performed | Performed | Performed | | <1 ppm | <1 ppm |
| Test Example 6 | 6-1<br>6-2<br>6-3<br>6-4 | PGMEA | PFA clean bottle | Glass | Diluted HF, HNO3 → washed with water | Performed | Performed | Performed | | <1 ppm | <1 ppm |
| Test Example 7 | 7-1<br>7-2<br>7-3<br>7-4 | EL | PFA clean bottle | Glass | Diluted HF, HNO3 → washed with water | Performed | Performed | Performed | | <1 ppm | <1 ppm |
| Test Example 8 | 8-1<br>8-2<br>8-3<br>8-4 | MPM | PFA clean bottle | Glass | Diluted HF, HNO3 → washed with water | Performed | Performed | Performed | | <1 ppm | <1 ppm |
| Test Example 9 | 9-1<br>9-2<br>9-3<br>9-4 | CyPe | PFA clean bottle | Glass | Diluted HF, HNO3 → washed with water | Performed | Performed | Performed | | <1 ppm | <1 ppm |
| Test Example 10 | 10-1<br>10-2<br>10-3<br>10-4 | CyHe | PFA clean bottle | Glass | Diluted HF, HNO3 → washed with water | Performed | Performed | Performed | | <1 ppm | <1 ppm |
| Test Example 11 | 11-1<br>11-2<br>11-3<br>11-4 | γBL | PFA clean bottle | Glass | Diluted HF, HNO3 → washed with water | Performed | Performed | Performed | | <1 ppm | <1 ppm |
| Test Example 12 | 12-1<br>12-2<br>12-3<br>12-4 | DIAE | PFA clean bottle | Glass | Diluted HF, HNO3 → washed with water | Performed | Performed | Performed | | <1 ppm | <1 ppm |
| Test Example 13 | 13-1<br>13-2<br>13-3<br>13-4 | iAA | PFA clean bottle | Glass | Diluted HF, HNO3 → washed with water | Performed | Performed | Performed | | <1 ppm | <1 ppm |

TABLE 2

| Table 1-1-2 | Step A4 Concentration environment | Step A4 Concentration condition | Step B4 Measurement environment | Step B4 LC/MS (relative quantity) | | Step B4 GC/MS (relative quantity) | | Step B4 DI-MS (relative quantity) | | Step B4 NMR (mass ppb) | |
|---|---|---|---|---|---|---|---|---|---|---|---|
| Test Example 1 | Class 1 | Pressure reduction in vacuum | Class 1 | 1.0<br>1.5<br>2.0<br>3.0 | Specific component A | 1.0<br>1.3<br>2.1<br>3.2 | Specific component A | 1.0<br>2.1<br>3.5<br>3.6 | Specific component B | 3.0<br>9.0<br>10.0<br>20.0 | Specific component B |
| Test Example 2 | Class 1 | Pressure reduction in vacuum | In the atmosphere | 1.0<br>2.7<br>3.0<br>3.7 | | 1.0<br>2.4<br>2.5<br>2.6 | | 1.0<br>3.9<br>4.0<br>4.2 | | 3.0<br>16.6<br>17.3<br>17.0 | |
| Test Example 3 | Class 1 | Pressure reduction in vacuum | Class 1 | 1.0<br>1.2<br>1.4<br>1.6 | | 1.0<br>1.5<br>2.1<br>2.6 | | 1.0<br>2.5<br>3.4<br>4.2 | | 2.0<br>10.5<br>11.0<br>18.2 | |
| Test Example 4 | Class 1 | Pressure reduction in vacuum | Class 1 | 1.0<br>1.4<br>1.8<br>2.2 | | 1.0<br>1.6<br>2.4<br>3.6 | | 1.0<br>2.6<br>3.8<br>5.8 | | 5.0<br>11.3<br>16.4<br>17.1 | |
| Test Example 5 | Class 1 | Pressure reduction in vacuum | Class 1 | 1.0<br>1.5<br>2.0<br>3.0 | | 1.0<br>2.9<br>3.6<br>4.4 | | 1.0<br>4.7<br>5.7<br>7.1 | | 6.0<br>20.0<br>24.6<br>26.4 | |
| Test Example 6 | Class 1 | Pressure reduction in vacuum | Class 1 | 1.0<br>1.8<br>2.6<br>3.4 | | 1.0<br>1.9<br>2.6<br>3.1 | | 1.0<br>3.1<br>4.2<br>5.0 | | 5.0<br>13.4<br>18.2<br>19.4 | |
| Test Example 7 | Class 1 | Pressure reduction in vacuum | Class 1 | 1.0<br>1.7<br>2.4<br>3.1 | | 1.0<br>1.6<br>2.0<br>2.2 | | 1.0<br>2.6<br>3.2<br>3.5 | | 4.0<br>11.0<br>16.0<br>15.2 | |
| Test Example 8 | Class 1 | Pressure reduction in vacuum | Class 1 | 1.0<br>1.6<br>2.2<br>2.8 | | 1.0<br>1.4<br>1.7<br>2.0 | | 1.0<br>2.2<br>2.8<br>3.3 | | 4.0<br>10.0<br>10.2<br>14.1 | |
| Test Example 9 | Class 1 | Pressure reduction in vacuum | Class 1 | 1.0<br>1.3<br>1.6<br>1.9 | | 1.0<br>1.2<br>1.4<br>1.4 | | 1.0<br>2.0<br>2.3<br>2.6 | | 3.0<br>8.4<br>10.0<br>10.6 | |
| Test Example 10 | Class 1 | Pressure reduction in vacuum | Class 1 | 1.0<br>1.4<br>1.8<br>2.2 | | 1.0<br>1.2<br>1.4<br>1.9 | | 1.0<br>1.9<br>2.8<br>3.4 | | 1.0<br>2.9<br>9.6<br>10.5 | |
| Test Example 11 | Class 1 | Pressure reduction in vacuum | Class 1 | 1.0<br>1.8<br>2.6<br>3.4 | | 1.0<br>1.9<br>2.8<br>3.7 | | 1.0<br>3.1<br>4.6<br>6.0 | | 8.0<br>10.2<br>19.5<br>21.3 | |
| Test Example 12 | Class 1 | Pressure reduction in vacuum | Class 1 | 1.0<br>1.2<br>1.4<br>1.6 | | 1.0<br>1.5<br>2.1<br>2.6 | | 1.0<br>2.5<br>3.4<br>4.2 | | 4.0<br>10.5<br>11.4<br>18.2 | |
| Test Example 13 | Class 1 | Pressure reduction in vacuum | Class 1 | 1.0<br>1.5<br>3.0<br>3.8 | | 1.0<br>1.4<br>1.9<br>1.9 | | 1.0<br>2.3<br>3.1<br>3.1 | | 3.0<br>9.8<br>13.3<br>13.4 | |

TABLE 3

| Table 1-1-3 | Step B4 ICP-MS (mass ppt) | | | | | | |
|---|---|---|---|---|---|---|---|
| | Ag | Al | As | Au | Ba | Ca | Cd |
| Test Example 1 | 0.010<br>0.014<br>0.020<br>0.027 | 0.030<br>0.042<br>0.059<br>0.082 | 0.001<br>0.001<br>0.002<br>0.003 | 0.001<br>0.001<br>0.002<br>0.003 | 0.002<br>0.003<br>0.004<br>0.005 | 0.050<br>0.070<br>0.098<br>0.137 | 0.001<br>0.001<br>0.002<br>0.003 |
| Test Example 2 | 0.048<br>0.067<br>0.094<br>0.132 | 0.144<br>0.202<br>0.282<br>0.395 | 0.005<br>0.007<br>0.009<br>0.013 | 0.005<br>0.007<br>0.009<br>0.013 | 0.010<br>0.013<br>0.019<br>0.026 | 0.240<br>0.336<br>0.470< br>0.659 | 0.005<br>0.007<br>0.009<br>0.013 |
| Test Example 3 | 0.008<br>0.011<br>0.016<br>0.022 | 0.024<br>0.034<br>0.047<br>0.066 | 0.001<br>0.001<br>0.002<br>0.002 | 0.001<br>0.001<br>0.002<br>0.002 | 0.002<br>0.002<br>0.003<br>0.004 | 0.040<br>0.056<br>0.078<br>0.110 | 0.001<br>0.001<br>0.002<br>0.002 |
| Test Example 4 | 0.012<br>0.017<br>0.024<br>0.033 | 0.036<br>0.050<br>0.071<br>0.099 | 0.001<br>0.002<br>0.002<br>0.003 | 0.001<br>0.002<br>0.002<br>0.003 | 0.002<br>0.003<br>0.005<br>0.007 | 0.060<br>0.084<br>0.118<br>0.165 | 0.001<br>0.002<br>0.002<br>0.003 |
| Test Example 5 | 0.014<br>0.020<br>0.028<br>0.040 | 0.043<br>0.060<br>0.085<br>0.119 | 0.001<br>0.002<br>0.003<br>0.004 | 0.001<br>0.002<br>0.003<br>0.004 | 0.003<br>0.004<br>0.006<br>0.008 | 0.072<br>0.101<br>0.141<br>0.198 | 0.001<br>0.002<br>0.003<br>0.004 |
| Test Example 6 | 0.013<br>0.018<br>0.025<br>0.036 | 0.039<br>0.054<br>0.076<br>0.107 | 0.001<br>0.002<br>0.003<br>0.004 | 0.001<br>0.002<br>0.003<br>0.004 | 0.003<br>0.004<br>0.005<br>0.007 | 0.065<br>0.091<br>0.127<br>0.178 | 0.001<br>0.002<br>0.003<br>0.004 |

TABLE 3-continued

| Table 1-1-3 | Step B4 ICP-MS (mass ppt) | | | | | | |
|---|---|---|---|---|---|---|---|
| | Ag | Al | As | Au | Ba | Ca | Cd |
| Test Example 7 | 0.022 | 0.066 | 0.002 | 0.002 | 0.004 | 0.110 | 0.002 |
| | 0.031 | 0.093 | 0.003 | 0.003 | 0.006 | 0.154 | 0.003 |
| | 0.043 | 0.130 | 0.004 | 0.004 | 0.009 | 0.216 | 0.004 |
| | 0.060 | 0.181 | 0.006 | 0.006 | 0.012 | 0.302 | 0.006 |
| Test Example 8 | 0.011 | 0.033 | 0.001 | 0.001 | 0.002 | 0.055 | 0.001 |
| | 0.015 | 0.046 | 0.002 | 0.002 | 0.003 | 0.077 | 0.002 |
| | 0.022 | 0.065 | 0.002 | 0.002 | 0.004 | 0.108 | 0.002 |
| | 0.030 | 0.091 | 0.003 | 0.003 | 0.006 | 0.151 | 0.003 |
| Test Example 9 | 0.012 | 0.036 | 0.001 | 0.001 | 0.002 | 0.061 | 0.001 |
| | 0.017 | 0.051 | 0.002 | 0.002 | 0.003 | 0.085 | 0.002 |
| | 0.024 | 0.071 | 0.002 | 0.002 | 0.005 | 0.119 | 0.002 |
| | 0.033 | 0.100 | 0.003 | 0.003 | 0.007 | 0.166 | 0.003 |
| Test Example 10 | 0.017 | 0.051 | 0.002 | 0.002 | 0.003 | 0.085 | 0.002 |
| | 0.024 | 0.071 | 0.002 | 0.002 | 0.005 | 0.119 | 0.002 |
| | 0.033 | 0.100 | 0.003 | 0.003 | 0.007 | 0.166 | 0.003 |
| | 0.047 | 0.140 | 0.005 | 0.005 | 0.009 | 0.233 | 0.005 |
| Test Example 11 | 0.022 | 0.066 | 0.002 | 0.002 | 0.004 | 0.110 | 0.002 |
| | 0.031 | 0.093 | 0.003 | 0.003 | 0.006 | 0.154 | 0.003 |
| | 0.043 | 0.130 | 0.004 | 0.004 | 0.009 | 0.216 | 0.004 |
| | 0.061 | 0.182 | 0.006 | 0.006 | 0.012 | 0.303 | 0.006 |
| Test Example 12 | 0.020 | 0.060 | 0.002 | 0.002 | 0.004 | 0.099 | 0.002 |
| | 0.028 | 0.083 | 0.003 | 0.003 | 0.006 | 0.139 | 0.003 |
| | 0.039 | 0.117 | 0.004 | 0.004 | 0.008 | 0.195 | 0.004 |
| | 0.054 | 0.163 | 0.005 | 0.005 | 0.011 | 0.272 | 0.005 |
| Test Example 13 | 0.015 | 0.045 | 0.001 | 0.001 | 0.003 | 0.074 | 0.001 |
| | 0.021 | 0.063 | 0.002 | 0.002 | 0.004 | 0.104 | 0.002 |
| | 0.029 | 0.088 | 0.003 | 0.003 | 0.006 | 0.146 | 0.003 |
| | 0.041 | 0.123 | 0.004 | 0.004 | 0.008 | 0.204 | 0.004 |

TABLE 4

| Table 1-1-4 | Step B4 ICP-MS (mass ppt) | | | | | | |
|---|---|---|---|---|---|---|---|
| | Co | Cr | Cu | Fe | Ga | K | Li |
| Test Example 1 | 0.020 | 0.001 | 0.003 | 0.080 | 0.001 | 0.030 | 0.020 |
| | 0.028 | 0.001 | 0.004 | 0.112 | 0.001 | 0.042 | 0.028 |
| | 0.039 | 0.002 | 0.006 | 0.157 | 0.002 | 0.059 | 0.039 |
| | 0.055 | 0.003 | 0.008 | 0.220 | 0.003 | 0.082 | 0.055 |
| Test Example 2 | 0.096 | 0.005 | 0.014 | 0.384 | 0.005 | 0.144 | 0.096 |
| | 0.134 | 0.007 | 0.020 | 0.538 | 0.007 | 0.202 | 0.134 |
| | 0.188 | 0.009 | 0.028 | 0.753 | 0.009 | 0.282 | 0.188 |
| | 0.263 | 0.013 | 0.040 | 1.054 | 0.013 | 0.395 | 0.263 |
| Test Example 3 | 0.016 | 0.001 | 0.002 | 0.064 | 0.001 | 0.024 | 0.016 |
| | 0.022 | 0.001 | 0.003 | 0.090 | 0.001 | 0.034 | 0.022 |
| | 0.031 | 0.002 | 0.005 | 0.125 | 0.002 | 0.047 | 0.031 |
| | 0.044 | 0.002 | 0.007 | 0.176 | 0.002 | 0.066 | 0.044 |
| Test Example 4 | 0.024 | 0.001 | 0.004 | 0.096 | 0.001 | 0.036 | 0.024 |
| | 0.034 | 0.002 | 0.005 | 0.134 | 0.002 | 0.050 | 0.034 |
| | 0.047 | 0.002 | 0.007 | 0.188 | 0.002 | 0.071 | 0.047 |
| | 0.066 | 0.003 | 0.010 | 0.263 | 0.003 | 0.099 | 0.066 |
| Test Example 5 | 0.029 | 0.001 | 0.004 | 0.115 | 0.001 | 0.043 | 0.029 |
| | 0.040 | 0.002 | 0.006 | 0.161 | 0.002 | 0.060 | 0.040 |
| | 0.056 | 0.003 | 0.008 | 0.226 | 0.003 | 0.085 | 0.056 |
| | 0.079 | 0.004 | 0.012 | 0.316 | 0.004 | 0.119 | 0.079 |
| Test Example 6 | 0.026 | 0.001 | 0.004 | 0.104 | 0.001 | 0.039 | 0.026 |
| | 0.036 | 0.002 | 0.005 | 0.145 | 0.002 | 0.054 | 0.036 |
| | 0.051 | 0.003 | 0.008 | 0.203 | 0.003 | 0.076 | 0.051 |
| | 0.071 | 0.004 | 0.011 | 0.284 | 0.004 | 0.107 | 0.071 |
| Test Example 7 | 0.044 | 0.002 | 0.007 | 0.176 | 0.002 | 0.066 | 0.044 |
| | 0.062 | 0.003 | 0.009 | 0.247 | 0.003 | 0.093 | 0.062 |
| | 0.086 | 0.004 | 0.013 | 0.345 | 0.004 | 0.130 | 0.086 |
| | 0.121 | 0.006 | 0.018 | 0.484 | 0.006 | 0.181 | 0.121 |
| Test Example 8 | 0.022 | 0.001 | 0.003 | 0.088 | 0.001 | 0.033 | 0.022 |
| | 0.031 | 0.002 | 0.005 | 0.123 | 0.002 | 0.046 | 0.031 |
| | 0.043 | 0.002 | 0.006 | 0.173 | 0.002 | 0.065 | 0.043 |
| | 0.060 | 0.003 | 0.009 | 0.242 | 0.003 | 0.091 | 0.060 |
| Test Example 9 | 0.024 | 0.001 | 0.004 | 0.097 | 0.001 | 0.036 | 0.024 |
| | 0.034 | 0.002 | 0.005 | 0.136 | 0.002 | 0.051 | 0.034 |
| | 0.048 | 0.002 | 0.007 | 0.190 | 0.002 | 0.071 | 0.048 |
| | 0.067 | 0.003 | 0.010 | 0.266 | 0.003 | 0.100 | 0.067 |

TABLE 4-continued

| Table 1-1-4 | Step B4 ICP-MS (mass ppt) | | | | | | |
|---|---|---|---|---|---|---|---|
| | Co | Cr | Cu | Fe | Ga | K | Li |
| Test Example 10 | 0.034 | 0.002 | 0.005 | 0.136 | 0.002 | 0.051 | 0.034 |
| | 0.048 | 0.002 | 0.007 | 0.190 | 0.002 | 0.071 | 0.048 |
| | 0.067 | 0.003 | 0.010 | 0.266 | 0.003 | 0.100 | 0.067 |
| | 0.093 | 0.005 | 0.014 | 0.372 | 0.005 | 0.140 | 0.093 |
| Test Example 11 | 0.044 | 0.002 | 0.007 | 0.176 | 0.002 | 0.066 | 0.044 |
| | 0.062 | 0.003 | 0.009 | 0.247 | 0.003 | 0.093 | 0.062 |
| | 0.086 | 0.004 | 0.013 | 0.346 | 0.004 | 0.130 | 0.086 |
| | 0.121 | 0.006 | 0.018 | 0.484 | 0.006 | 0.182 | 0.121 |
| Test Example 12 | 0.040 | 0.002 | 0.006 | 0.159 | 0.002 | 0.060 | 0.040 |
| | 0.056 | 0.003 | 0.008 | 0.222 | 0.003 | 0.083 | 0.056 |
| | 0.078 | 0.004 | 0.012 | 0.311 | 0.004 | 0.117 | 0.078 |
| | 0.109 | 0.005 | 0.016 | 0.436 | 0.005 | 0.163 | 0.109 |
| Test Example 13 | 0.030 | 0.001 | 0.004 | 0.119 | 0.001 | 0.045 | 0.030 |
| | 0.042 | 0.002 | 0.006 | 0.167 | 0.002 | 0.063 | 0.042 |
| | 0.058 | 0.003 | 0.009 | 0.233 | 0.003 | 0.088 | 0.058 |
| | 0.082 | 0.004 | 0.012 | 0.327 | 0.004 | 0.123 | 0.082 |

TABLE 5

| Table 1-1-5 | Step B4 ICP-MS (mass ppt) | | | | | | |
|---|---|---|---|---|---|---|---|
| | Mg | Mn | Mo | Na | Nb | Ni | Pb |
| Test Example 1 | 0.010 | 0.002 | 0.001 | 0.030 | 0.001 | 0.001 | 0.001 |
| | 0.014 | 0.003 | 0.001 | 0.042 | 0.001 | 0.001 | 0.001 |
| | 0.020 | 0.004 | 0.002 | 0.059 | 0.002 | 0.002 | 0.002 |
| | 0.027 | 0.005 | 0.003 | 0.082 | 0.003 | 0.003 | 0.003 |
| Test Example 2 | 0.048 | 0.010 | 0.005 | 0.144 | 0.005 | 0.005 | 0.005 |
| | 0.067 | 0.013 | 0.007 | 0.202 | 0.007 | 0.007 | 0.007 |
| | 0.094 | 0.019 | 0.009 | 0.282 | 0.009 | 0.009 | 0.009 |
| | 0.132 | 0.026 | 0.013 | 0.395 | 0.013 | 0.013 | 0.013 |
| Test Example 3 | 0.008 | 0.002 | 0.001 | 0.024 | 0.001 | 0.001 | 0.001 |
| | 0.011 | 0.002 | 0.001 | 0.034 | 0.001 | 0.001 | 0.001 |
| | 0.016 | 0.003 | 0.002 | 0.047 | 0.002 | 0.002 | 0.002 |
| | 0.022 | 0.004 | 0.002 | 0.066 | 0.002 | 0.002 | 0.002 |
| Test Example 4 | 0.012 | 0.002 | 0.001 | 0.036 | 0.001 | 0.001 | 0.001 |
| | 0.017 | 0.003 | 0.002 | 0.050 | 0.002 | 0.002 | 0.002 |
| | 0.024 | 0.005 | 0.002 | 0.071 | 0.002 | 0.002 | 0.002 |
| | 0.033 | 0.007 | 0.003 | 0.099 | 0.003 | 0.003 | 0.003 |
| Test Example 5 | 0.014 | 0.003 | 0.001 | 0.043 | 0.001 | 0.001 | 0.001 |
| | 0.020 | 0.004 | 0.002 | 0.060 | 0.002 | 0.002 | 0.002 |
| | 0.028 | 0.006 | 0.003 | 0.085 | 0.003 | 0.003 | 0.003 |
| | 0.040 | 0.008 | 0.004 | 0.119 | 0.004 | 0.004 | 0.004 |
| Test Example 6 | 0.013 | 0.003 | 0.001 | 0.039 | 0.001 | 0.001 | 0.001 |
| | 0.018 | 0.004 | 0.002 | 0.054 | 0.002 | 0.002 | 0.002 |
| | 0.025 | 0.005 | 0.003 | 0.076 | 0.003 | 0.003 | 0.003 |
| | 0.036 | 0.007 | 0.004 | 0.107 | 0.004 | 0.004 | 0.004 |
| Test Example 7 | 0.022 | 0.004 | 0.002 | 0.066 | 0.002 | 0.002 | 0.002 |
| | 0.031 | 0.006 | 0.003 | 0.093 | 0.003 | 0.003 | 0.003 |
| | 0.043 | 0.009 | 0.004 | 0.130 | 0.004 | 0.004 | 0.004 |
| | 0.060 | 0.012 | 0.006 | 0.181 | 0.006 | 0.006 | 0.006 |
| Test Example 8 | 0.011 | 0.002 | 0.001 | 0.033 | 0.001 | 0.001 | 0.001 |
| | 0.015 | 0.003 | 0.002 | 0.046 | 0.002 | 0.002 | 0.002 |
| | 0.022 | 0.004 | 0.002 | 0.065 | 0.002 | 0.002 | 0.002 |
| | 0.030 | 0.006 | 0.003 | 0.091 | 0.003 | 0.003 | 0.003 |
| Test Example 9 | 0.012 | 0.002 | 0.001 | 0.036 | 0.001 | 0.001 | 0.001 |
| | 0.017 | 0.003 | 0.002 | 0.051 | 0.002 | 0.002 | 0.002 |
| | 0.024 | 0.005 | 0.002 | 0.071 | 0.002 | 0.002 | 0.002 |
| | 0.033 | 0.007 | 0.003 | 0.100 | 0.003 | 0.003 | 0.003 |
| Test Example 10 | 0.017 | 0.003 | 0.002 | 0.051 | 0.002 | 0.002 | 0.002 |
| | 0.024 | 0.005 | 0.002 | 0.071 | 0.002 | 0.002 | 0.002 |
| | 0.033 | 0.007 | 0.003 | 0.100 | 0.003 | 0.003 | 0.003 |
| | 0.047 | 0.009 | 0.005 | 0.140 | 0.005 | 0.005 | 0.005 |
| Test Example 11 | 0.022 | 0.004 | 0.002 | 0.066 | 0.002 | 0.002 | 0.002 |
| | 0.031 | 0.006 | 0.003 | 0.093 | 0.003 | 0.003 | 0.003 |
| | 0.043 | 0.009 | 0.004 | 0.130 | 0.004 | 0.004 | 0.004 |
| | 0.061 | 0.012 | 0.006 | 0.182 | 0.006 | 0.006 | 0.006 |
| Test Example 12 | 0.020 | 0.004 | 0.002 | 0.060 | 0.002 | 0.002 | 0.002 |
| | 0.028 | 0.006 | 0.003 | 0.083 | 0.003 | 0.003 | 0.003 |
| | 0.039 | 0.008 | 0.004 | 0.117 | 0.004 | 0.004 | 0.004 |
| | 0.054 | 0.011 | 0.005 | 0.163 | 0.005 | 0.005 | 0.005 |

TABLE 5-continued

| Table 1-1-5 | Step B4 ICP-MS (mass ppt) | | | | | | |
|---|---|---|---|---|---|---|---|
| | Mg | Mn | Mo | Na | Nb | Ni | Pb |
| Test Example 13 | 0.015 | 0.003 | 0.001 | 0.045 | 0.001 | 0.001 | 0.001 |
| | 0.021 | 0.004 | 0.002 | 0.063 | 0.002 | 0.002 | 0.002 |
| | 0.029 | 0.006 | 0.003 | 0.088 | 0.003 | 0.003 | 0.003 |
| | 0.041 | 0.008 | 0.004 | 0.123 | 0.004 | 0.004 | 0.004 |

TABLE 6

| Table 1-1-6 | Step B4 ICP-MS (mass ppt) | | | | | | |
|---|---|---|---|---|---|---|---|
| | Sb | Sn | Sr | Ta | Th | Ti | Tl |
| Test Example 1 | 0.001 | 0.001 | 0.009 | 0.001 | 0.001 | 0.040 | 0.001 |
| | 0.001 | 0.001 | 0.013 | 0.001 | 0.001 | 0.056 | 0.001 |
| | 0.002 | 0.002 | 0.018 | 0.002 | 0.002 | 0.078 | 0.002 |
| | 0.003 | 0.003 | 0.025 | 0.003 | 0.003 | 0.110 | 0.003 |
| Test Example 2 | 0.005 | 0.005 | 0.043 | 0.005 | 0.005 | 0.192 | 0.005 |
| | 0.007 | 0.007 | 0.060 | 0.007 | 0.007 | 0.269 | 0.007 |
| | 0.009 | 0.009 | 0.085 | 0.009 | 0.009 | 0.376 | 0.009 |
| | 0.013 | 0.013 | 0.119 | 0.013 | 0.013 | 0.527 | 0.013 |
| Test Example 3 | 0.001 | 0.001 | 0.007 | 0.001 | 0.001 | 0.032 | 0.001 |
| | 0.001 | 0.001 | 0.010 | 0.001 | 0.001 | 0.045 | 0.001 |
| | 0.002 | 0.002 | 0.014 | 0.002 | 0.002 | 0.063 | 0.002 |
| | 0.002 | 0.002 | 0.020 | 0.002 | 0.002 | 0.088 | 0.002 |
| Test Example 4 | 0.001 | 0.001 | 0.011 | 0.001 | 0.001 | 0.048 | 0.001 |
| | 0.002 | 0.002 | 0.015 | 0.002 | 0.002 | 0.067 | 0.002 |
| | 0.002 | 0.002 | 0.021 | 0.002 | 0.002 | 0.094 | 0.002 |
| | 0.003 | 0.003 | 0.030 | 0.003 | 0.003 | 0.132 | 0.003 |
| Test Example 5 | 0.001 | 0.001 | 0.013 | 0.001 | 0.001 | 0.058 | 0.001 |
| | 0.002 | 0.002 | 0.018 | 0.002 | 0.002 | 0.081 | 0.002 |
| | 0.003 | 0.003 | 0.025 | 0.003 | 0.003 | 0.113 | 0.003 |
| | 0.004 | 0.004 | 0.036 | 0.004 | 0.004 | 0.158 | 0.004 |
| Test Example 6 | 0.001 | 0.001 | 0.012 | 0.001 | 0.001 | 0.052 | 0.001 |
| | 0.002 | 0.002 | 0.016 | 0.002 | 0.002 | 0.073 | 0.002 |
| | 0.003 | 0.003 | 0.023 | 0.003 | 0.003 | 0.102 | 0.003 |
| | 0.004 | 0.004 | 0.032 | 0.004 | 0.004 | 0.142 | 0.004 |
| Test Example 7 | 0.002 | 0.002 | 0.020 | 0.002 | 0.002 | 0.088 | 0.002 |
| | 0.003 | 0.003 | 0.028 | 0.003 | 0.003 | 0.123 | 0.003 |
| | 0.004 | 0.004 | 0.039 | 0.004 | 0.004 | 0.173 | 0.004 |
| | 0.006 | 0.006 | 0.054 | 0.006 | 0.006 | 0.242 | 0.006 |
| Test Example 8 | 0.001 | 0.001 | 0.010 | 0.001 | 0.001 | 0.044 | 0.001 |
| | 0.002 | 0.002 | 0.014 | 0.002 | 0.002 | 0.062 | 0.002 |
| | 0.002 | 0.002 | 0.019 | 0.002 | 0.002 | 0.086 | 0.002 |
| | 0.003 | 0.003 | 0.027 | 0.003 | 0.003 | 0.121 | 0.003 |
| Test Example 9 | 0.001 | 0.001 | 0.011 | 0.001 | 0.001 | 0.048 | 0.001 |
| | 0.002 | 0.002 | 0.015 | 0.002 | 0.002 | 0.068 | 0.002 |
| | 0.002 | 0.002 | 0.021 | 0.002 | 0.002 | 0.095 | 0.002 |
| | 0.003 | 0.003 | 0.030 | 0.003 | 0.003 | 0.133 | 0.003 |
| Test Example 10 | 0.002 | 0.002 | 0.015 | 0.002 | 0.002 | 0.068 | 0.002 |
| | 0.002 | 0.002 | 0.021 | 0.002 | 0.002 | 0.095 | 0.002 |
| | 0.003 | 0.003 | 0.030 | 0.003 | 0.003 | 0.133 | 0.003 |
| | 0.005 | 0.005 | 0.042 | 0.005 | 0.005 | 0.186 | 0.005 |
| Test Example 11 | 0.002 | 0.002 | 0.020 | 0.002 | 0.002 | 0.088 | 0.002 |
| | 0.003 | 0.003 | 0.028 | 0.003 | 0.003 | 0.124 | 0.003 |
| | 0.004 | 0.004 | 0.039 | 0.004 | 0.004 | 0.173 | 0.004 |
| | 0.006 | 0.006 | 0.054 | 0.006 | 0.006 | 0.242 | 0.006 |
| Test Example 12 | 0.002 | 0.002 | 0.018 | 0.002 | 0.002 | 0.079 | 0.002 |
| | 0.003 | 0.003 | 0.025 | 0.003 | 0.003 | 0.111 | 0.003 |
| | 0.004 | 0.004 | 0.035 | 0.004 | 0.004 | 0.156 | 0.004 |
| | 0.005 | 0.005 | 0.049 | 0.005 | 0.005 | 0.218 | 0.005 |
| Test Example 13 | 0.001 | 0.001 | 0.013 | 0.001 | 0.001 | 0.060 | 0.001 |
| | 0.002 | 0.002 | 0.019 | 0.002 | 0.002 | 0.083 | 0.002 |
| | 0.003 | 0.003 | 0.026 | 0.003 | 0.003 | 0.117 | 0.003 |
| | 0.004 | 0.004 | 0.037 | 0.004 | 0.004 | 0.163 | 0.004 |

TABLE 7

| Table 1-1-7 | Step B4 ICP-MS (mass ppt) | | | | | |
|---|---|---|---|---|---|---|
| | V | W | Zn | Zr | Mo | Total |
| Test Example 1 | 0.001 | 0.001 | 0.006 | 0.001 | 0.001 | 0.360 |
| | 0.001 | 0.001 | 0.008 | 0.001 | 0.001 | 0.497 |
| | 0.002 | 0.002 | 0.012 | 0.002 | 0.002 | 0.708 |
| | 0.003 | 0.003 | 0.016 | 0.003 | 0.003 | 0.990 |
| Test Example 2 | 0.005 | 0.005 | 0.029 | 0.005 | 0.005 | 1.732 |
| | 0.007 | 0.007 | 0.040 | 0.007 | 0.007 | 2.423 |
| | 0.009 | 0.009 | 0.056 | 0.009 | 0.009 | 3.378 |
| | 0.013 | 0.013 | 0.079 | 0.013 | 0.013 | 4.739 |
| Test Example 3 | 0.001 | 0.001 | 0.005 | 0.001 | 0.001 | 0.292 |
| | 0.001 | 0.001 | 0.007 | 0.001 | 0.001 | 0.401 |
| | 0.002 | 0.002 | 0.009 | 0.002 | 0.002 | 0.571 |
| | 0.002 | 0.002 | 0.013 | 0.002 | 0.002 | 0.788 |
| Test Example 4 | 0.001 | 0.001 | 0.007 | 0.001 | 0.001 | 0.428 |
| | 0.002 | 0.002 | 0.010 | 0.002 | 0.002 | 0.609 |
| | 0.002 | 0.002 | 0.014 | 0.002 | 0.002 | 0.843 |
| | 0.003 | 0.003 | 0.020 | 0.003 | 0.003 | 1.183 |
| Test Example 5 | 0.001 | 0.001 | 0.009 | 0.001 | 0.001 | 0.510 |
| | 0.002 | 0.002 | 0.012 | 0.002 | 0.002 | 0.723 |
| | 0.003 | 0.003 | 0.017 | 0.003 | 0.003 | 1.019 |
| | 0.004 | 0.004 | 0.024 | 0.004 | 0.004 | 1.427 |
| Test Example 6 | 0.001 | 0.001 | 0.008 | 0.001 | 0.001 | 0.464 |
| | 0.002 | 0.002 | 0.011 | 0.002 | 0.002 | 0.655 |
| | 0.003 | 0.003 | 0.015 | 0.003 | 0.003 | 0.922 |
| | 0.004 | 0.004 | 0.021 | 0.004 | 0.004 | 1.289 |
| Test Example 7 | 0.002 | 0.002 | 0.013 | 0.002 | 0.002 | 0.788 |
| | 0.003 | 0.003 | 0.019 | 0.003 | 0.003 | 1.111 |
| | 0.004 | 0.004 | 0.026 | 0.004 | 0.004 | 1.550 |
| | 0.006 | 0.006 | 0.036 | 0.006 | 0.006 | 2.173 |
| Test Example 8 | 0.001 | 0.001 | 0.007 | 0.001 | 0.001 | 0.394 |
| | 0.002 | 0.002 | 0.009 | 0.002 | 0.002 | 0.562 |
| | 0.002 | 0.002 | 0.013 | 0.002 | 0.002 | 0.774 |
| | 0.003 | 0.003 | 0.018 | 0.003 | 0.003 | 1.087 |
| Test Example 9 | 0.001 | 0.001 | 0.007 | 0.001 | 0.001 | 0.430 |
| | 0.002 | 0.002 | 0.010 | 0.002 | 0.002 | 0.616 |
| | 0.002 | 0.002 | 0.014 | 0.002 | 0.002 | 0.849 |
| | 0.003 | 0.003 | 0.020 | 0.003 | 0.003 | 1.193 |
| Test Example 10 | 0.002 | 0.002 | 0.010 | 0.002 | 0.002 | 0.616 |
| | 0.002 | 0.002 | 0.014 | 0.002 | 0.002 | 0.849 |
| | 0.003 | 0.003 | 0.020 | 0.003 | 0.003 | 1.193 |
| | 0.005 | 0.005 | 0.028 | 0.005 | 0.005 | 1.683 |
| Test Example 11 | 0.002 | 0.002 | 0.013 | 0.002 | 0.002 | 0.788 |
| | 0.003 | 0.003 | 0.019 | 0.003 | 0.003 | 1.112 |
| | 0.004 | 0.004 | 0.026 | 0.004 | 0.004 | 1.551 |
| | 0.006 | 0.006 | 0.036 | 0.006 | 0.006 | 2.179 |
| Test Example 12 | 0.002 | 0.002 | 0.012 | 0.002 | 0.002 | 0.717 |
| | 0.003 | 0.003 | 0.017 | 0.003 | 0.003 | 1.005 |
| | 0.004 | 0.004 | 0.023 | 0.004 | 0.004 | 1.405 |
| | 0.005 | 0.005 | 0.033 | 0.005 | 0.005 | 1.951 |
| Test Example 13 | 0.001 | 0.001 | 0.009 | 0.001 | 0.001 | 0.528 |
| | 0.002 | 0.002 | 0.013 | 0.002 | 0.002 | 0.751 |
| | 0.003 | 0.003 | 0.018 | 0.003 | 0.003 | 1.053 |
| | 0.004 | 0.004 | 0.025 | 0.004 | 0.004 | 1.471 |

TABLE 8

| Table 1-1-8 | Evaluation | | | | | |
|---|---|---|---|---|---|---|
| | Total number of defects | Number of metal defects | Coefficient of correlation | | | |
| | | | LC/MS and total number of defects | GC/MS and total number of defects | DI-MS and total number of defects | NMR and total number of defects | ICP-MS and number of metal defects |
| Test Example 1 | 123 | 2 | 0.982 | 0.969 | 0.959 | 0.953 | 0.987 |
| | 250 | 5 | | | | | |
| | 370 | 7 | | | | | |
| | 492 | 9 | | | | | |

TABLE 8-continued

| Table 1-1-8 | Total number of defects | Number of metal defects | Coefficient of correlation ||||| 
|---|---|---|---|---|---|---|---|
| | | | LC/MS and total number of defects | GC/MS and total number of defects | DI-MS and total number of defects | NMR and total number of defects | ICP-MS and number of metal defects |
| Test Example 2 | 123<br>250<br>370<br>492 | 2<br>5<br>7<br>9 | 0.952 | 0.845 | 0.833 | 0.796 | 0.977 |
| Test Example 3 | 246<br>500<br>740<br>984 | 4<br>9<br>12<br>18 | 1.000 | 0.999 | 0.992 | 0.959 | 0.991 |
| Test Example 4 | 98.4<br>200<br>296<br>393.6 | 1<br>4<br>5<br>7 | 1.000 | 0.986 | 0.996 | 0.958 | 0.972 |
| Test Example 5 | 147.6<br>300<br>444<br>590.4 | 3<br>5<br>9<br>11 | 0.982 | 0.972 | 0.959 | 0.923 | 0.967 |
| Test Example 6 | 184.5<br>375<br>555<br>738 | 3<br>7<br>11<br>13 | 1.000 | 0.990 | 0.975 | 0.950 | 0.973 |
| Test Example 7 | 369<br>750<br>1110<br>1476 | 7<br>12<br>20<br>27 | 1.000 | 0.981 | 0.950 | 0.910 | 0.992 |
| Test Example 8 | 307.5<br>625<br>925<br>1230 | 6<br>11<br>15<br>22 | 1.000 | 1.000 | 0.978 | 0.948 | 0.994 |
| Test Example 9 | 172.2<br>350<br>518<br>688.8 | 2<br>6<br>9<br>12 | 1.000 | 0.910 | 0.958 | 0.915 | 0.976 |
| Test Example 10 | 246<br>500<br>740<br>984 | 3<br>9<br>13<br>18 | 1.000 | 0.955 | 0.996 | 0.955 | 0.972 |
| Test Example 11 | 147.6<br>300<br>444<br>590.4 | 3<br>5<br>9<br>11 | 1.000 | 1.000 | 0.997 | 0.956 | 0.965 |
| Test Example 12 | 233.7<br>475<br>703<br>934.8 | 2<br>9<br>13<br>17 | 1.000 | 0.999 | 0.992 | 0.967 | 0.968 |
| Test Example 13 | 369<br>750<br>1110<br>1476 | 5<br>14<br>20<br>27 | 0.981 | 0.952 | 0.931 | 0.920 | 0.980 |

TABLE 9

| Table 1-2-1 | No. | Chemical liquid || Fourth container Material of liquid contact portion | Step |||| Liquid contact portion || Result of elution Test ||
|---|---|---|---|---|---|---|---|---|---|---|---|---|
| | | Organic solvent | Second container | | Acid washing | Ultrasonic washing | Specific washing solution | Drying | $P_1$ | $P_2$ | Fluoride ion | Metal component |
| Test Example 14 | 14-1<br>14-2<br>14-3<br>14-4 | MIBC | PFA clean bottle | Glass | Diluted HF, HNO3 → washed with water | Performed | Performed | Performed | | | <1 ppm | <1 ppm |
| Test Example 15 | 15-1<br>15-2<br>15-3<br>15-4 | PGMEA/PGME (7:3) | PFA clean bottle | Glass | Diluted HF, HNO3 → washed with water | Performed | Performed | Performed | | | <1 ppm | <1 ppm |
| Test Example 16 | 16-1<br>16-2<br>16-3<br>16-4 | CyHe | PFA clean bottle | Electro-polished SUS | Diluted HF, HNO3 → washed with water | Performed | Performed | Performed | 1.2 | 0.6 | <1 ppm | <1 ppm |
| Test Example 17 | 17-1<br>17-2<br>17-3<br>17-4 | CyHe | PFA clean bottle | PTFE container | Diluted HF, HNO3 → washed with water | Performed | Performed | Performed | | | <1 ppm | <1 ppm |
| Test Example 18 | 18-1<br>18-2<br>18-3<br>18-4 | CyHe | Electro-polished SUS | Glass | Diluted HF, HNO3 → washed with water | Performed | Performed | Performed | | | <1 ppm | <1 ppm |
| Test Example 19 | 19-1<br>19-2<br>19-3<br>19-4 | CyHe | PFA clean bottle | Glass | Diluted HF, HNO3 → washed with water | Performed | Performed | Performed | | | <1 ppm | <1 ppm |

TABLE 9-continued

| | | Chemical liquid | | Step W4 Fourth container Material of liquid contact portion | Step | | | | Liquid contact portion | | Result of elution Test | |
|---|---|---|---|---|---|---|---|---|---|---|---|---|
| Table 1-2-1 | No. | Organic solvent | Second container | | Acid washing | Ultrasonic washing | Specific washing solution | Drying | $P_1$ | $P_2$ | Fluoride ion | Metal component |
| Test Example 20 | 20-1 20-2 20-3 20-4 | CyHe | PFA clean bottle | Glass | Diluted HF, HNO3 → washed with water | Performed | Performed | Performed | | | <1 ppm | <1 ppm |
| Test Example 21 | 21-1 21-2 21-3 21-4 | CyHe | PFA clean bottle | Glass | Washed with water | Performed | Performed | Performed | | | <1 ppm | <1 ppm |
| Test Example 22 | 22-1 22-2 22-3 22-4 | CyHe | PFA clean bottle | Glass | Diluted HF, HNO3 → washed with water | — | Performed | Performed | | | <1 ppm | <1 ppm |

TABLE 10

| | Step A4 | | | Step B4 | | | | | | | |
|---|---|---|---|---|---|---|---|---|---|---|---|
| Table 1-2-2 | Concentration environment | Concentration condition | Measurement environment | LC/MS (relative quantity) | | GC/MS (relative quantity) | | DI-MS (relative quantity) | | NMR (mass ppb) | |
| Test Example 14 | Class 1 | Pressure reduction in vacuum | Class 1 | 1.0 1.6 2.2 2.8 | Specific component A | 1.0 1.6 2.3 2.3 | Specific component A | 1.0 2.6 3.7 3.8 | Specific component B | 5.0 11.0 15.7 16.2 | Specific component B |
| Test Example 15 | Class 1 | Pressure reduction in vacuum | Class 1 | 1.0 1.9 2.8 3.7 | | 1.0 1.0 2.6 3.1 | | 1.0 3.6 4.2 4.3 | | 3.0 3.6 4.8 19.1 | |
| Test Example 16 | Class 1 | Pressure reduction in vacuum | Class 1 | 1.0 2.1 2.3 3.8 | | 1.0 1.1 1.9 2.0 | | 1.0 1.2 3.0 3.0 | | 6.0 6.4 7.0 13.6 | |
| Test Example 17 | Class 1 | Pressure reduction in vacuum | Class 1 | 1.0 1.5 3.0 4.0 | | 1.0 1.6 2.1 2.3 | | 1.0 2.6 3.4 3.5 | | 2.0 13.0 14.5 16.2 | |
| Test Example 18 | Class 1 | Pressure reduction in vacuum | Class 1 | 1.0 1.8 3.5 3.8 | | 1.0 1.7 2.9 3.2 | | 1.0 2.7 4.7 5.1 | | 9.0 11.7 12.0 21.1 | |
| Test Example 19 | Class 1 | Heating concentration N2 | Class 1 | 1.0 2.2 3.5 4.1 | | 1.0 1.9 2.8 3.1 | | 1.0 4.0 4.4 5.0 | | 2.0 4.0 19.0 21.5 | |
| Test Example 20 | Class 1 | Heating concentration Ar | Class 1 | 1.0 2.4 3.0 4.5 | | 1.0 2.2 3.0 3.4 | | 1.0 3.5 4.8 5.6 | | 4.0 15.2 16.1 23.8 | |
| Test Example 21 | Class 1 | Pressure reduction in vacuum | Class 1 | 1.0 4.0 5.5 5.2 | | 1.0 1.9 2.8 2.5 | | 1.0 4.0 4.4 4.0 | | 4.0 2.0 4.0 25.0 | |
| Test Example 22 | Class 1 | Pressure reduction in vacuum | Class 1 | 1.0 2.0 4.0 3.8 | | 1.0 2.2 3.0 2.8 | | 1.0 3.5 4.8 4.5 | | 8.0 7.0 11.0 23.8 | |

TABLE 11

| Table 1-2-3 | Step B4 ICP-MS (mass ppt) | | | | | | |
|---|---|---|---|---|---|---|---|
| | Ag | Al | As | Au | Ba | Ca | Cd |
| Test Example 14 | 0.013 | 0.040 | 0.001 | 0.001 | 0.003 | 0.067 | 0.001 |
| | 0.019 | 0.056 | 0.002 | 0.002 | 0.004 | 0.094 | 0.002 |
| | 0.026 | 0.079 | 0.003 | 0.003 | 0.005 | 0.131 | 0.003 |
| | 0.037 | 0.110 | 0.004 | 0.004 | 0.007 | 0.184 | 0.004 |
| Test Example 15 | 0.015 | 0.044 | 0.001 | 0.001 | 0.003 | 0.074 | 0.001 |
| | 0.021 | 0.062 | 0.002 | 0.002 | 0.004 | 0.103 | 0.002 |
| | 0.029 | 0.087 | 0.003 | 0.003 | 0.006 | 0.144 | 0.003 |
| | 0.040 | 0.121 | 0.004 | 0.004 | 0.008 | 0.202 | 0.004 |
| Test Example 16 | 0.016 | 0.049 | 0.002 | 0.002 | 0.003 | 0.081 | 0.002 |
| | 0.023 | 0.068 | 0.002 | 0.002 | 0.005 | 0.113 | 0.002 |
| | 0.032 | 0.095 | 0.003 | 0.003 | 0.006 | 0.159 | 0.003 |
| | 0.044 | 0.133 | 0.004 | 0.004 | 0.009 | 0.222 | 0.004 |
| Test Example 17 | 0.018 | 0.053 | 0.002 | 0.002 | 0.004 | 0.089 | 0.002 |
| | 0.025 | 0.075 | 0.002 | 0.002 | 0.005 | 0.125 | 0.002 |
| | 0.035 | 0.105 | 0.003 | 0.003 | 0.007 | 0.175 | 0.003 |
| | 0.049 | 0.147 | 0.005 | 0.005 | 0.010 | 0.245 | 0.005 |
| Test Example 18 | 0.020 | 0.059 | 0.002 | 0.002 | 0.004 | 0.098 | 0.002 |
| | 0.027 | 0.082 | 0.003 | 0.003 | 0.005 | 0.137 | 0.003 |
| | 0.038 | 0.115 | 0.004 | 0.004 | 0.008 | 0.192 | 0.004 |
| | 0.054 | 0.161 | 0.005 | 0.005 | 0.011 | 0.269 | 0.005 |
| Test Example 19 | 0.022 | 0.065 | 0.002 | 0.002 | 0.004 | 0.108 | 0.002 |
| | 0.030 | 0.091 | 0.003 | 0.003 | 0.006 | 0.151 | 0.003 |
| | 0.042 | 0.127 | 0.004 | 0.004 | 0.008 | 0.211 | 0.004 |
| | 0.059 | 0.178 | 0.006 | 0.006 | 0.012 | 0.296 | 0.006 |
| Test Example 20 | 0.024 | 0.071 | 0.002 | 0.002 | 0.005 | 0.119 | 0.002 |
| | 0.033 | 0.100 | 0.003 | 0.003 | 0.007 | 0.166 | 0.003 |
| | 0.047 | 0.140 | 0.005 | 0.005 | 0.009 | 0.233 | 0.005 |
| | 0.065 | 0.195 | 0.007 | 0.007 | 0.013 | 0.326 | 0.007 |
| Test Example 21 | 0.019 | 0.057 | 0.002 | 0.002 | 0.004 | 0.095 | 0.002 |
| | 0.021 | 0.063 | 0.002 | 0.002 | 0.004 | 0.105 | 0.002 |
| | 0.042 | 0.126 | 0.004 | 0.004 | 0.008 | 0.209 | 0.004 |
| | 0.078 | 0.234 | 0.008 | 0.008 | 0.016 | 0.391 | 0.008 |
| Test Example 22 | 0.021 | 0.063 | 0.002 | 0.002 | 0.004 | 0.105 | 0.002 |
| | 0.023 | 0.069 | 0.002 | 0.002 | 0.005 | 0.116 | 0.002 |
| | 0.046 | 0.138 | 0.005 | 0.005 | 0.009 | 0.230 | 0.005 |
| | 0.086 | 0.258 | 0.009 | 0.009 | 0.017 | 0.430 | 0.009 |

TABLE 12

| Table 1-2-4 | Step B4 ICP-MS (mass ppt) | | | | | | |
|---|---|---|---|---|---|---|---|
| | Co | Cr | Cu | Fe | Ga | K | Li |
| Test Example 14 | 0.027 | 0.001 | 0.004 | 0.107 | 0.001 | 0.040 | 0.027 |
| | 0.038 | 0.002 | 0.006 | 0.150 | 0.002 | 0.056 | 0.038 |
| | 0.053 | 0.003 | 0.008 | 0.210 | 0.003 | 0.079 | 0.053 |
| | 0.074 | 0.004 | 0.011 | 0.294 | 0.004 | 0.110 | 0.074 |
| Test Example 15 | 0.029 | 0.001 | 0.004 | 0.118 | 0.001 | 0.044 | 0.029 |
| | 0.041 | 0.002 | 0.006 | 0.165 | 0.002 | 0.062 | 0.041 |
| | 0.058 | 0.003 | 0.009 | 0.231 | 0.003 | 0.087 | 0.058 |
| | 0.081 | 0.004 | 0.012 | 0.324 | 0.004 | 0.121 | 0.081 |
| Test Example 16 | 0.032 | 0.002 | 0.005 | 0.130 | 0.002 | 0.049 | 0.032 |
| | 0.045 | 0.002 | 0.007 | 0.182 | 0.002 | 0.068 | 0.045 |
| | 0.064 | 0.003 | 0.010 | 0.254 | 0.003 | 0.095 | 0.064 |
| | 0.089 | 0.004 | 0.013 | 0.356 | 0.004 | 0.133 | 0.089 |
| Test Example 17 | 0.036 | 0.002 | 0.005 | 0.143 | 0.002 | 0.053 | 0.036 |
| | 0.050 | 0.002 | 0.007 | 0.200 | 0.002 | 0.075 | 0.050 |
| | 0.070 | 0.003 | 0.010 | 0.280 | 0.003 | 0.105 | 0.070 |
| | 0.098 | 0.005 | 0.015 | 0.391 | 0.005 | 0.147 | 0.098 |
| Test Example 18 | 0.039 | 0.002 | 0.006 | 0.157 | 0.002 | 0.059 | 0.039 |
| | 0.055 | 0.003 | 0.008 | 0.220 | 0.003 | 0.082 | 0.055 |
| | 0.077 | 0.004 | 0.012 | 0.308 | 0.004 | 0.115 | 0.077 |
| | 0.108 | 0.005 | 0.016 | 0.431 | 0.005 | 0.161 | 0.108 |
| Test Example 19 | 0.043 | 0.002 | 0.006 | 0.173 | 0.002 | 0.065 | 0.043 |
| | 0.060 | 0.003 | 0.009 | 0.242 | 0.003 | 0.091 | 0.060 |
| | 0.085 | 0.004 | 0.013 | 0.338 | 0.004 | 0.127 | 0.085 |
| | 0.118 | 0.006 | 0.018 | 0.474 | 0.006 | 0.178 | 0.118 |
| Test Example 20 | 0.047 | 0.002 | 0.007 | 0.190 | 0.002 | 0.071 | 0.047 |
| | 0.066 | 0.003 | 0.010 | 0.266 | 0.003 | 0.100 | 0.066 |
| | 0.093 | 0.005 | 0.014 | 0.372 | 0.005 | 0.140 | 0.093 |
| | 0.130 | 0.007 | 0.020 | 0.521 | 0.007 | 0.195 | 0.130 |
| Test Example 21 | 0.038 | 0.002 | 0.006 | 0.152 | 0.002 | 0.057 | 0.038 |
| | 0.042 | 0.002 | 0.006 | 0.168 | 0.002 | 0.063 | 0.042 |
| | 0.084 | 0.004 | 0.013 | 0.335 | 0.004 | 0.126 | 0.084 |
| | 0.156 | 0.008 | 0.023 | 0.625 | 0.008 | 0.234 | 0.156 |
| Test Example 22 | 0.042 | 0.002 | 0.006 | 0.167 | 0.002 | 0.063 | 0.042 |
| | 0.046 | 0.002 | 0.007 | 0.185 | 0.002 | 0.069 | 0.046 |
| | 0.092 | 0.005 | 0.014 | 0.368 | 0.005 | 0.138 | 0.092 |
| | 0.172 | 0.009 | 0.026 | 0.688 | 0.009 | 0.258 | 0.172 |

TABLE 13

| Table 1-2-5 | Step B4 ICP-MS (mass ppt) | | | | | | |
|---|---|---|---|---|---|---|---|
| | Mg | Mn | Mo | Na | Nb | Ni | Pb |
| Test Example 14 | 0.013 | 0.003 | 0.001 | 0.040 | 0.001 | 0.001 | 0.001 |
| | 0.019 | 0.004 | 0.002 | 0.056 | 0.002 | 0.002 | 0.002 |
| | 0.026 | 0.005 | 0.003 | 0.079 | 0.003 | 0.003 | 0.003 |
| | 0.037 | 0.007 | 0.004 | 0.110 | 0.004 | 0.004 | 0.004 |
| Test Example 15 | 0.015 | 0.003 | 0.001 | 0.044 | 0.001 | 0.001 | 0.001 |
| | 0.021 | 0.004 | 0.002 | 0.062 | 0.002 | 0.002 | 0.002 |
| | 0.029 | 0.006 | 0.003 | 0.087 | 0.003 | 0.003 | 0.003 |
| | 0.040 | 0.008 | 0.004 | 0.121 | 0.004 | 0.004 | 0.004 |
| Test Example 16 | 0.016 | 0.003 | 0.002 | 0.049 | 0.002 | 0.002 | 0.002 |
| | 0.023 | 0.005 | 0.002 | 0.068 | 0.002 | 0.002 | 0.002 |
| | 0.032 | 0.006 | 0.003 | 0.095 | 0.003 | 0.003 | 0.003 |
| | 0.044 | 0.009 | 0.004 | 0.133 | 0.004 | 0.004 | 0.004 |
| Test Example 17 | 0.018 | 0.004 | 0.002 | 0.053 | 0.002 | 0.002 | 0.002 |
| | 0.025 | 0.005 | 0.002 | 0.075 | 0.002 | 0.002 | 0.002 |
| | 0.035 | 0.007 | 0.003 | 0.105 | 0.003 | 0.003 | 0.003 |
| | 0.049 | 0.010 | 0.005 | 0.147 | 0.005 | 0.005 | 0.005 |
| Test Example 18 | 0.020 | 0.004 | 0.002 | 0.059 | 0.002 | 0.002 | 0.002 |
| | 0.027 | 0.005 | 0.003 | 0.082 | 0.003 | 0.003 | 0.003 |
| | 0.038 | 0.008 | 0.004 | 0.115 | 0.004 | 0.004 | 0.004 |
| | 0.054 | 0.011 | 0.005 | 0.161 | 0.005 | 0.005 | 0.005 |
| Test Example 19 | 0.022 | 0.004 | 0.002 | 0.065 | 0.002 | 0.002 | 0.002 |
| | 0.030 | 0.006 | 0.003 | 0.091 | 0.003 | 0.003 | 0.003 |
| | 0.042 | 0.008 | 0.004 | 0.127 | 0.004 | 0.004 | 0.004 |
| | 0.059 | 0.012 | 0.006 | 0.178 | 0.006 | 0.006 | 0.006 |
| Test Example 20 | 0.024 | 0.005 | 0.002 | 0.071 | 0.002 | 0.002 | 0.002 |
| | 0.033 | 0.007 | 0.003 | 0.100 | 0.003 | 0.003 | 0.003 |
| | 0.047 | 0.009 | 0.005 | 0.140 | 0.005 | 0.005 | 0.005 |
| | 0.065 | 0.013 | 0.007 | 0.195 | 0.007 | 0.007 | 0.007 |
| Test Example 21 | 0.019 | 0.004 | 0.002 | 0.057 | 0.002 | 0.002 | 0.002 |
| | 0.021 | 0.004 | 0.002 | 0.063 | 0.002 | 0.002 | 0.002 |
| | 0.042 | 0.008 | 0.004 | 0.126 | 0.004 | 0.004 | 0.004 |
| | 0.078 | 0.016 | 0.008 | 0.234 | 0.008 | 0.008 | 0.008 |
| Test Example 22 | 0.021 | 0.004 | 0.002 | 0.063 | 0.002 | 0.002 | 0.002 |
| | 0.023 | 0.005 | 0.002 | 0.069 | 0.002 | 0.002 | 0.002 |
| | 0.046 | 0.009 | 0.005 | 0.138 | 0.005 | 0.005 | 0.005 |
| | 0.086 | 0.017 | 0.009 | 0.258 | 0.009 | 0.009 | 0.009 |

TABLE 14

| Table 1-2-6 | Step B4 ICP-MS (mass ppt) | | | | | | |
|---|---|---|---|---|---|---|---|
| | Sb | Sn | Sr | Ta | Th | Ti | Tl |
| Test Example 14 | 0.001 | 0.001 | 0.012 | 0.001 | 0.001 | 0.054 | 0.001 |
| | 0.002 | 0.002 | 0.017 | 0.002 | 0.002 | 0.075 | 0.002 |
| | 0.003 | 0.003 | 0.024 | 0.003 | 0.003 | 0.105 | 0.003 |
| | 0.004 | 0.004 | 0.033 | 0.004 | 0.004 | 0.147 | 0.004 |
| Test Example 15 | 0.001 | 0.001 | 0.013 | 0.001 | 0.001 | 0.059 | 0.001 |
| | 0.002 | 0.002 | 0.019 | 0.002 | 0.002 | 0.083 | 0.002 |
| | 0.003 | 0.003 | 0.026 | 0.003 | 0.003 | 0.116 | 0.003 |
| | 0.004 | 0.004 | 0.036 | 0.004 | 0.004 | 0.162 | 0.004 |

TABLE 14-continued

| Table 1-2-6 | Step B4 ICP-MS (mass ppt) | | | | | | |
|---|---|---|---|---|---|---|---|
| | Sb | Sn | Sr | Ta | Th | Ti | Tl |
| Test Example 16 | 0.002 | 0.002 | 0.015 | 0.002 | 0.002 | 0.065 | 0.002 |
| | 0.002 | 0.002 | 0.020 | 0.002 | 0.002 | 0.091 | 0.002 |
| | 0.003 | 0.003 | 0.029 | 0.003 | 0.003 | 0.127 | 0.003 |
| | 0.004 | 0.004 | 0.040 | 0.004 | 0.004 | 0.178 | 0.004 |
| Test Example 17 | 0.002 | 0.002 | 0.016 | 0.002 | 0.002 | 0.071 | 0.002 |
| | 0.002 | 0.002 | 0.022 | 0.002 | 0.002 | 0.100 | 0.002 |
| | 0.003 | 0.003 | 0.031 | 0.003 | 0.003 | 0.140 | 0.003 |
| | 0.005 | 0.005 | 0.044 | 0.005 | 0.005 | 0.196 | 0.005 |
| Test Example 18 | 0.002 | 0.002 | 0.018 | 0.002 | 0.002 | 0.078 | 0.002 |
| | 0.003 | 0.003 | 0.025 | 0.003 | 0.003 | 0.110 | 0.003 |
| | 0.004 | 0.004 | 0.035 | 0.004 | 0.004 | 0.154 | 0.004 |
| | 0.005 | 0.005 | 0.048 | 0.005 | 0.005 | 0.215 | 0.005 |
| Test Example 19 | 0.002 | 0.002 | 0.019 | 0.002 | 0.002 | 0.086 | 0.002 |
| | 0.003 | 0.003 | 0.027 | 0.003 | 0.003 | 0.121 | 0.003 |
| | 0.004 | 0.004 | 0.038 | 0.004 | 0.004 | 0.169 | 0.004 |
| | 0.006 | 0.006 | 0.053 | 0.006 | 0.006 | 0.237 | 0.006 |
| Test Example 20 | 0.002 | 0.002 | 0.021 | 0.002 | 0.002 | 0.095 | 0.002 |
| | 0.003 | 0.003 | 0.030 | 0.003 | 0.003 | 0.133 | 0.003 |
| | 0.005 | 0.005 | 0.042 | 0.005 | 0.005 | 0.186 | 0.005 |
| | 0.007 | 0.007 | 0.059 | 0.007 | 0.007 | 0.261 | 0.007 |
| Test Example 21 | 0.002 | 0.002 | 0.017 | 0.002 | 0.002 | 0.076 | 0.002 |
| | 0.002 | 0.002 | 0.019 | 0.002 | 0.002 | 0.084 | 0.002 |
| | 0.004 | 0.004 | 0.038 | 0.004 | 0.004 | 0.167 | 0.004 |
| | 0.008 | 0.008 | 0.070 | 0.008 | 0.008 | 0.313 | 0.008 |
| Test Example 22 | 0.002 | 0.002 | 0.019 | 0.002 | 0.002 | 0.084 | 0.002 |
| | 0.002 | 0.002 | 0.021 | 0.002 | 0.002 | 0.093 | 0.002 |
| | 0.005 | 0.005 | 0.041 | 0.005 | 0.005 | 0.184 | 0.005 |
| | 0.009 | 0.009 | 0.077 | 0.009 | 0.009 | 0.344 | 0.009 |

TABLE 15

| Table 1-2-7 | Step B4 ICP-MS (mass ppt) | | | | | |
|---|---|---|---|---|---|---|
| | V | W | Zn | Zr | Mo | Total |
| Test Example 14 | 0.001 | 0.001 | 0.008 | 0.001 | 0.001 | 0.476 |
| | 0.002 | 0.002 | 0.011 | 0.002 | 0.002 | 0.679 |
| | 0.003 | 0.003 | 0.016 | 0.003 | 0.003 | 0.953 |
| | 0.004 | 0.004 | 0.022 | 0.004 | 0.004 | 1.329 |
| Test Example 15 | 0.001 | 0.001 | 0.009 | 0.001 | 0.001 | 0.521 |
| | 0.002 | 0.002 | 0.012 | 0.002 | 0.002 | 0.742 |
| | 0.003 | 0.003 | 0.017 | 0.003 | 0.003 | 1.044 |
| | 0.004 | 0.004 | 0.024 | 0.004 | 0.004 | 1.453 |
| Test Example 16 | 0.002 | 0.002 | 0.010 | 0.002 | 0.002 | 0.591 |
| | 0.002 | 0.002 | 0.014 | 0.002 | 0.002 | 0.813 |
| | 0.003 | 0.003 | 0.019 | 0.003 | 0.003 | 1.141 |
| | 0.004 | 0.004 | 0.027 | 0.004 | 0.004 | 1.591 |
| Test Example 17 | 0.002 | 0.002 | 0.011 | 0.002 | 0.002 | 0.646 |
| | 0.002 | 0.002 | 0.015 | 0.002 | 0.002 | 0.890 |
| | 0.003 | 0.003 | 0.021 | 0.003 | 0.003 | 1.250 |
| | 0.005 | 0.005 | 0.029 | 0.005 | 0.005 | 1.765 |
| Test Example 18 | 0.002 | 0.002 | 0.012 | 0.002 | 0.002 | 0.708 |
| | 0.003 | 0.003 | 0.016 | 0.003 | 0.003 | 0.990 |
| | 0.004 | 0.004 | 0.023 | 0.004 | 0.004 | 1.387 |
| | 0.005 | 0.005 | 0.032 | 0.005 | 0.005 | 1.930 |
| Test Example 19 | 0.002 | 0.002 | 0.013 | 0.002 | 0.002 | 0.774 |
| | 0.003 | 0.003 | 0.018 | 0.003 | 0.003 | 1.087 |
| | 0.004 | 0.004 | 0.025 | 0.004 | 0.004 | 1.517 |
| | 0.006 | 0.006 | 0.036 | 0.006 | 0.006 | 2.134 |
| Test Example 20 | 0.002 | 0.002 | 0.014 | 0.002 | 0.002 | 0.847 |
| | 0.003 | 0.003 | 0.020 | 0.003 | 0.003 | 1.191 |
| | 0.005 | 0.005 | 0.028 | 0.005 | 0.005 | 1.683 |
| | 0.007 | 0.007 | 0.039 | 0.007 | 0.007 | 2.353 |
| Test Example 21 | 0.002 | 0.002 | 0.011 | 0.002 | 0.002 | 0.686 |
| | 0.002 | 0.002 | 0.013 | 0.002 | 0.002 | 0.754 |
| | 0.004 | 0.004 | 0.025 | 0.004 | 0.004 | 1.505 |
| | 0.008 | 0.008 | 0.047 | 0.008 | 0.008 | 2.815 |
| Test Example 22 | 0.002 | 0.002 | 0.013 | 0.002 | 0.002 | 0.753 |
| | 0.002 | 0.002 | 0.014 | 0.002 | 0.002 | 0.827 |
| | 0.005 | 0.005 | 0.028 | 0.005 | 0.005 | 1.663 |
| | 0.009 | 0.009 | 0.052 | 0.009 | 0.009 | 3.103 |

TABLE 16

| Table 1-2-8 | Evaluation | | | | | |
|---|---|---|---|---|---|---|
| | Total number of defects | Number of metal defects | LC/MS and total number of defects | GC/MS and total number of defects | DI-MS and total number of defects | NMR and total number of defects | ICP-MS and number of metal defects |
| Test Example 14 | 430.5 | 6 | 1.000 | 0.963 | 0.947 | 0.952 | 0.982 |
| | 875 | 16 | | | | | |
| | 1295 | 23 | | | | | |
| | 1722 | 31 | | | | | |
| Test Example 15 | 258.3 | 4 | 1.000 | 0.933 | 0.872 | 0.828 | 0.985 |
| | 525 | 9 | | | | | |
| | 777 | 14 | | | | | |
| | 1033.2 | 19 | | | | | |
| Test Example 16 | 246 | 3 | 0.970 | 0.936 | 0.914 | 0.838 | 0.974 |
| | 500 | 9 | | | | | |
| | 740 | 13 | | | | | |
| | 984 | 18 | | | | | |
| Test Example 17 | 246 | 3 | 0.982 | 0.980 | 0.935 | 0.892 | 0.972 |
| | 500 | 9 | | | | | |
| | 740 | 13 | | | | | |
| | 984 | 18 | | | | | |
| Test Example 18 | 246 | 3 | 0.969 | 0.975 | 0.972 | 0.895 | 0.976 |
| | 500 | 9 | | | | | |
| | 740 | 13 | | | | | |
| | 984 | 18 | | | | | |
| Test Example 19 | 246 | 3 | 0.990 | 0.986 | 0.905 | 0.941 | 0.975 |
| | 500 | 9 | | | | | |
| | 740 | 13 | | | | | |
| | 984 | 18 | | | | | |
| Test Example 20 | 246 | 3 | 0.989 | 0.983 | 0.968 | 0.959 | 0.976 |
| | 500 | 9 | | | | | |
| | 740 | 13 | | | | | |
| | 984 | 18 | | | | | |
| Test Example 21 | 246 | 3 | 0.890 | 0.894 | 0.776 | 0.767 | 0.901 |
| | 500 | 9 | | | | | |
| | 740 | 13 | | | | | |
| | 984 | 18 | | | | | |
| Test Example 22 | 246 | 3 | 0.928 | 0.899 | 0.885 | 0.851 | 0.902 |
| | 500 | 9 | | | | | |
| | 740 | 13 | | | | | |
| | 984 | 18 | | | | | |

Example 1

By performing linear regression on the content of the specific component in the concentrated liquid of each of the chemical liquids 1-1 to 1-4 obtained in Test Example 1 and the number of defects of each of the chemical liquids, a calibration curve was created. Then, based on the calibration curve, "400/12 inchWf" was determined as the total number of defects for determining whether a chemical liquid is adequate or inadequate (in other words, the desired defect inhibition performance was set to be "400/12 inchWf"), and the content of the specific component measured by each of LC/MS and GC/MS corresponding thereto was calculated from the calibration curve and determined as a standard value.

Then, by the same method as that used for manufacturing the chemical liquids 1-1 and 1-4, chemical liquids 1-1(2) and 1-4(2) were manufactured on a day different from the day on which the chemical liquids 1-1 and 1-4 were manufactured.

Subsequently, by using the chemical liquids 1-1(2) and 1-4(2), concentrated liquids were prepared by the same method as in Test Example 1, and the content of the specific component was measured by the same method as in Test Example 1.

The obtained measurement results were compared with the standard value determined as described above. As a result, the content of the specific component in the chemical liquid 1-1(2) was equal to or smaller than the standard value. Therefore, the chemical liquid 1-1(2) was determined as being adequate. In contrast, the content of the specific component in the chemical liquid 1-4(2) was greater than the standard value. Therefore, the chemical liquid 1-4(2) was determined as being inadequate.

Subsequently, the defect inhibition performance of the chemical liquids 1-1(2) and 1-4(2) was evaluated by the same method as in Test Example 1. As a result, the total number of defects of the chemical liquid 1-1(2) was 121/12 inchWf, and the total number of defects of the chemical liquid 1-4(2) was 490/12 inchWf.

From the above results, it was understood that by the present quality inspection method for a chemical liquid, the defect inhibition performance of a chemical liquid can be simply evaluated.

Example 2

By performing linear regression on the content of the specific component in each of the concentrated liquids of the chemical liquids 2-1 to 2-4 obtained in Test Example 2 and the number of defects of each of the chemical liquids, a calibration curve was created. Then, based on the calibration curve, the content of the specific component (relative quantity) which corresponded to the total number of defects of 400/12 inchWf and was measured by each of LC/MS and GC/MS was determined as a standard value.

Thereafter, by the same method as that used for manufacturing the chemical liquids 2-1 and 2-4, chemical liquids 2-1(2) and 2-4(2) were manufactured on a day different from the day on which the chemical liquids 2-1 and 2-4 were manufactured.

Subsequently, by using the chemical liquids 2-1(2) and 2-4(2), concentrated liquids were prepared by the same method as in Test Example 2, and the content of the specific component was measured by the same method as in Test Example 2.

The obtained measurement results were compared with the standard value determined as described above. As a result, the content of the specific component in the chemical liquid 2-1(2) was equal to or smaller than the standard value. Therefore, the chemical liquid 2-1(2) was determined as being adequate. In contrast, the content of the specific component in the chemical liquid 2-4(2) was greater than the standard value. Therefore, the chemical liquid 2-4(2) was determined as being inadequate.

Then, the defect inhibition performance of the chemical liquids 2-1(2) and 2-4(2) was evaluated by the same method as in Test Example 1. As a result, the total number of defects of the chemical liquid 2-1(2) was 122/12 inchWf, and the total number of defects of the chemical liquid 2-4(2) was 491/12 inchWf.

Examples 3 to 22

A chemical liquid denoted by (first number)-1 and a chemical liquid denoted by (first number)-4 corresponding to a test example denoted by (first number) were manufactured in the same manner as described above on another day. Then, the chemical liquids were concentrated by a method corresponding to each test example denoted by (first number), the content of the specific component was analyzed and compared with the predetermined standard value, and whether the chemical liquid was adequate or inadequate was determined. For each of the chemical liquids, the defect inhibition performance was evaluated. As a result, the predicted defect inhibition performance calculated from the calibration curve based on the content of the specific component substantially coincided with the actually measured defect inhibition performance. Therefore, it was understood that by the above method, the defect inhibition performance of a chemical liquid can be simply evaluated.

Comparative Example 1

By performing linear regression on the content of the specific component in the concentrated liquids of the chemical liquids 1-1 to 1-4 obtained in Test Example 1 and the number of defects of each of the chemical liquids, a calibration curve was created. Then, based on the calibration curve, the content of the specific component which corresponded to the total number of defects of 400/12 inchWf and was measured by each of LC/MS and GC/MS was determined as a standard value.

Then, by the same method as that used for manufacturing the chemical liquids 1-1 and 1-4, chemical liquids 1-1(2) and 1-4(2) were manufactured on a day different from the day on which the chemical liquids 1-1 and 1-4 were manufactured.

Thereafter, the content of the specific component in the chemical liquids 1-1(2) and 1-4(2) was measured by the same method as in Example 1, except that each of the chemical liquids was concentrated not in a clean room but in the atmosphere.

The obtained measurement results were compared with the standard value determined as above. As a result, the content of the specific component in the chemical liquids 1-1(2) and 1-4(2) was greater than the standard value. Therefore, both the chemical liquids were determined as being inadequate.

Subsequently, the defect inhibition performance of the chemical liquids 1-1(2) and 1-4(2) was evaluated by the same method as in Test Example 1. As a result, the total number of defects of the chemical liquid 1-1(2) was 121/12 inchWf, and the total number of defects of the chemical liquid 1-4(2) was 490/12 inchWf.

From the above results, it was understood that unless the chemical liquid is concentrated in a predetermined clean room, the defect inhibition performance of the chemical liquid cannot be accurately evaluated.

Comparative Example 2

By performing linear regression on the content of the specific component in the concentrated liquids of the chemical liquids 1-1 to 1-4 obtained in Test Example 1 and the number of defects of each of the chemical liquids, a calibration curve was created. Then, based on the calibration curve, the content of the specific component which corresponded to the total number of defects of 400/12 inchWf and was measured by each of LC/MS and GC/MS was determined as a standard value.

Then, by the same method as that used for manufacturing the chemical liquids 1-1 and 1-4, chemical liquids 1-1(2) and 1-4(2) were manufactured on a day different from the day on which the chemical liquids 1-1 and 1-4 were manufactured.

Thereafter, the content of the specific component in the chemical liquids 1-1(2) and 1-4(2) was measured by the same method as in Example 1, except that the first container was used without being washed.

The obtained measurement results were compared with the standard value determined as above. As a result, the content of the specific component in the chemical liquids 1-1(2) and 1-4(2) was greater than the standard value. Therefore, both the chemical liquids were determined as being inadequate.

Subsequently, the defect inhibition performance of the chemical liquids 1-1(2) and 1-4(2) was evaluated by the same method as in Test Example 1. As a result, the total number of defects of the chemical liquid 1-1(2) was 121/12 inchWf, and the total number of defects of the chemical liquid 1-4(2) was 490/12 inchWf.

From the above results, it was understood that unless the first container is washed by a predetermined method, the defect inhibition performance cannot be accurately evaluated.

Comparative Example 3

By performing linear regression on the content of the specific component in the concentrated liquids of the chemical liquids 1-1 to 1-4 obtained in Test Example 1 and the number of defects of each of the chemical liquids, a calibration curve was created. Then, based on the calibration curve, the content of the specific component which corresponded to the total number of defects of 400/12 inchWf and was measured by each of LC/MS and GC/MS was determined as a standard value.

Then, by the same method as that used for manufacturing the chemical liquids 1-1 and 1-4, chemical liquids 1-1(2) and 1-4(2) were manufactured on a day different from the day on which the chemical liquids 1-1 and 1-4 were manufactured.

Thereafter, the content of the specific component in the chemical liquids 1-1(2) and 1-4(2) was measured by the same method as in Example 1, except that the chemical liquid was concentrated in the air by means of heating concentration.

Subsequently, the obtained measurement results were compared with the standard value determined as above. As a result, the content of the specific component in the chemical liquids 1-1(2) and 1-4(2) was greater than the standard value. Therefore, both the chemical liquids were determined as being inadequate.

Then, the defect inhibition performance of the chemical liquids 1-1(2) and 1-4(2) was evaluated by the same method as in Test Example 1. As a result, the total number of defects of the chemical liquid 1-1(2) was 121/12 inchWf, and the total number of defects of the chemical liquid 1-4(2) was 490/12 inchWf.

From the above results, it was understood that unless the chemical liquid is concentrated under predetermined conditions, the defect inhibition performance cannot be accurately evaluated.

What is claimed is:

1. A quality inspection method for a chemical liquid used for manufacturing a semiconductor substrate, comprising:
    a step W of preparing a first container having a liquid contact portion of which at least a portion is formed of at least one kind of material selected from a group consisting of glass, a fluorine-containing polymer, and electropolished stainless steel, adopting a portion of the chemical liquid as a liquid, and washing at least a portion of the liquid contact portion by using a liquid;
    a step A of adopting a portion of the chemical liquid as b liquid and performing concentration of b liquid by using the washed first container so as to obtain c liquid;
    a step B of performing measurement of a content of a specific component in c liquid; and
    a step C of comparing the content of the specific component with a preset standard value,
    wherein the step W, the step A, the step B, and the step C are performed in this order,
    at least the step W and the step A are performed in a clean room having cleanliness equal to or higher than class 4 specified in the International Standard ISO14644-1: 2015 established by the International Organization for Standardization,
    the concentration is performed under at least one kind of inert gas selected from a group consisting of an Ar gas, a He gas, and a $N_2$ gas or under reduced pressure, and
    the measurement is performed by at least one kind of measurement method selected from a group consisting of gas chromatography mass spectrometry, gas chromatography tandem mass spectrometry, gas chromatography atomic emission detection, gas chromatography quadrupole time-of-flight type mass spectrometry, direct sample introduction-type mass spectrometry, high-performance liquid chromatography mass spectrometry, high-performance liquid chromatography tandem mass spectrometry, high-performance liquid chromatography time-of-flight type mass spectrometry, inductively coupled plasma mass spectrometry, inductively coupled plasma emission spectrometry, temperature programmed desorption mass spectrometry, ion chromatography, nuclear magnetic resonance spectrometry, and atomic absorption spectrometry.

2. The quality inspection method for the chemical liquid according to claim 1, further comprising:
    a step D of determining the chemical liquid as being inadequate and discarding the chemical liquid in a case where the content of the specific component is greater than the standard value in the step C; or
    a step E of purifying the chemical liquid in a case where the content of the specific component is greater than the standard value in the step C and then performing again the step W, the step A, the step B, and the step C.

3. The quality inspection method for the chemical liquid according to claim 1,
    wherein the step B is also performed in the clean room.

4. The quality inspection method for the chemical liquid according to claim 1,
    wherein the step W further has at least one kind of step selected from a group consisting of a step of performing acid washing on at least the liquid contact portion of the first container, a step of performing ultrasonic washing on at least the liquid contact portion of the first container, and a step of drying at least the liquid contact portion of the first container.

5. The quality inspection method for the chemical liquid according to claim 1,
wherein a factor of concentration in the step A is 2 to 1,000,000.

6. The quality inspection method for the chemical liquid according to claim 1,
wherein a factor of concentration in the step A is 10 to 10,000.

7. The quality inspection method for the chemical liquid according to claim 1,
wherein the specific component contains at least one kind of compound selected from a group consisting of Formulae (1) to (7)

(1)
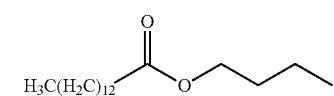

(2)
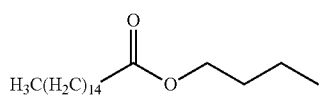

(3)
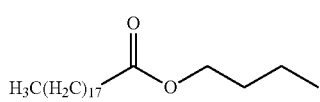

(4)
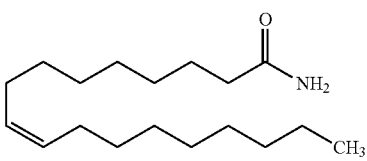

(5)
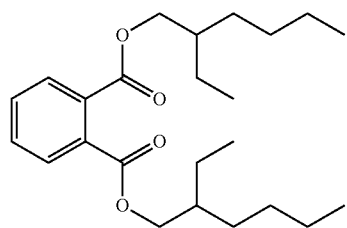

(6)
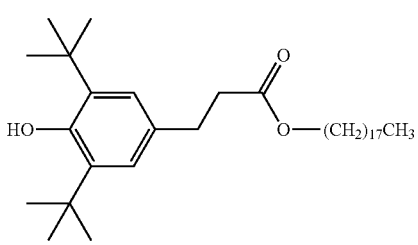

-continued (7)
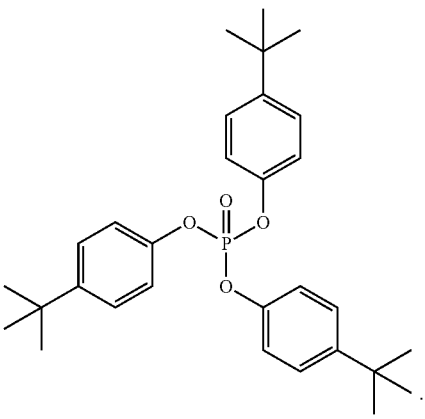

8. The quality inspection method for the chemical liquid according to claim 1,
wherein a temperature condition of the concentration in the step A is 10° C. to 250° C.

9. The quality inspection method for the chemical liquid according to claim 1,
wherein a volume of b liquid in the step A is equal to or smaller than 5 L.

10. The quality inspection method for the chemical liquid according to claim 1,
wherein in a case where the first container is a fluorine-containing polymer container in which at least a portion of the liquid contact portion is formed of a fluorine-containing polymer, the fluorine-containing polymer container satisfies a condition 1 or a condition 2 in the following test,
test: a portion of the chemical liquid is adopted as d liquid, the liquid contact portion is washed using d liquid, a portion of the chemical liquid is adopted as e liquid, and under the condition that a ratio of a mass of the washed fluorine-containing polymer container to a mass of e liquid becomes 1.0 provided that a liquid temperature of e liquid is 25° C., the washed fluorine-containing polymer container is immersed for 24 hours in e liquid having a liquid temperature of 25° C.,
condition 1: in a case where e liquid having been used for the immersion contains one kind of fluoride ion, an increase of one kind of the fluoride ion before and after the immersion is equal to or smaller than 1 mass ppm,
condition 2: in a case where e liquid having been used for the immersion contains two or more kinds of fluoride ions, a total increase of two or more kinds of the fluoride ions before and after the immersion is equal to or smaller than 1 mass ppm.

11. The quality inspection method for the chemical liquid according to claim 1,
wherein in a case where the first container is a fluorine-containing polymer container in which at least a portion of the liquid contact portion is formed of a fluorine-containing polymer, within a surface of at least a portion of the liquid contact portion, provided that an atom number ratio of the number of fluorine atoms contained in the surface to the number of carbon atoms contained in the surface is $M_1$, and an atom number ratio of the number of fluorine atoms contained in a position, which is 10 nm below the surface in a thickness direction of the fluorine-containing polymer 12. The quality inspection method for the chemical liquid according to claim 1,
wherein in a case where the first container is an electropolished stainless steel container in which at least a portion of the liquid contact portion is formed of electropolished stainless steel, the electropolished stainless steel container satisfies a condition 3 or a condition 4 in the following test,
test: a portion of the chemical liquid is adopted as f liquid, the liquid contact portion is washed using f liquid, a portion of the chemical liquid is adopted as g liquid, and under the condition that a ratio of a mass of the washed electropolished stainless steel container to a mass of g liquid becomes 0.25 provided that a liquid temperature of g liquid is 25° C., the washed electropolished stainless steel container is immersed for 24 hours in g liquid having a liquid temperature of 25° C.,
condition 3: in a case where g liquid having been used for the immersion contains one kind of metal component, an increase of one kind of the metal component before and after the immersion is equal to or smaller than 1 mass ppm,
condition 4: in a case where g liquid having been used for the immersion contains two or more kinds of metal components, a total increase of two or more kinds of the metal components before and after the immersion is equal to or smaller than 1 mass ppm.

13. The quality inspection method for the chemical liquid according to claim 1,
wherein in a case where the first container is an electropolished stainless steel container in which at least a portion of the liquid contact portion is formed of electropolished stainless steel, within a surface of at least a portion of the liquid contact portion, provided that an atom number ratio of the number of chromium atoms contained in the surface to the number of iron atoms contained in the surface is $P_1$, and an atom number ratio of the number of chromium atoms contained in a position, which is 10 nm below the surface in a thickness direction of the electropolished stainless steel container, to the number of iron atoms contained in the position is $P_2$, a ratio of $P_1$ to $P_2$ is higher than 1.0.

14. The quality inspection method for the chemical liquid according to claim 1,
wherein in a case where the first container is an electropolished stainless steel container in which at least a portion of the liquid contact portion is formed of electropolished stainless steel, within a surface of at least a portion of the liquid contact portion, an atom number ratio of the number of chromium atoms contained in a position, which is 1 nm below the surface in a thickness direction of the electropolished stainless steel container, to the number of iron atoms contained in the position is equal to or higher than 1.0.

15. The quality inspection method for the chemical liquid according to claim 1,
wherein the chemical liquid contains at least one kind of organic solvent selected from a group consisting of propylene glycol monomethyl ether, propylene glycol monoethyl ether, propylene glycol monopropyl ether, propylene glycol monomethyl ether acetate, ethyl lactate, methoxymethyl propionate, cyclopentanone, cyclohexanone, γ-butyrolactone, diisoamyl ether, butyl acetate, isoamyl acetate, isopropanol, and 4-methyl-2-pentanol.

16. The quality inspection method for the chemical liquid according to claim 1,
wherein the measurement includes organic analysis for measuring a content of an organic component in c liquid and inorganic analysis for measuring a content of an inorganic component in c liquid.

17. The quality inspection method for the chemical liquid according to claim 1,
wherein the measurement is performed by at least one kind of measurement method selected from the group consisting of gas chromatography mass spectrometry, gas chromatography tandem mass spectrometry, high-performance liquid chromatography mass spectrometry, high-performance liquid chromatography tandem mass spectrometry, and inductively coupled plasma mass spectrometry.

18. The quality inspection method for the chemical liquid according to claim 1,
wherein the measurement is performed by at least one kind of measurement method selected from the group consisting of high-performance liquid chromatography mass spectrometry and high-performance liquid chromatography tandem mass spectrometry.

19. The quality inspection method for the chemical liquid according to claim 1,
wherein each of the content of the specific component measured in the step B and the standard value compared in the step C is an absolute quantity.

20. The quality inspection method for the chemical liquid according to claim 1,
wherein each of the content of the specific component measured in the step B and the standard value compared in the step C is a relative quantity.

21. The quality inspection method for the chemical liquid according to claim 1,
wherein the measurement is performed by at least one kind of measurement method selected from the group consisting of gas chromatography mass spectrometry, gas chromatography tandem mass spectrometry, high-performance liquid chromatography mass spectrometry, and high-performance liquid chromatography tandem mass spectrometry, and
the specific component contains an organic substance in which m/Z is 300 to 1,000.

22. The quality inspection method for the chemical liquid according to claim 1,
wherein the measurement includes inorganic analysis for analyzing a content of an inorganic component in c liquid, and
provided that the content of the specific component measured in the step B is an absolute quantity, the absolute quantity is determined by a standard addition method.

23. The quality inspection method for the chemical liquid according to claim 1,
wherein in a case where the content of the specific component is be equal to or smaller than the standard value in the step C, the chemical liquid is determined as being adequate.

24. The quality inspection method for the chemical liquid according to claim 1,
wherein the specific component contains an organic substance having a boiling point equal to or higher than 200° C.

25. The quality inspection method for the chemical liquid according to claim 24,
wherein the specific component contains an organic substance having a boiling point of 300° C. to 800° C.

26. The quality inspection method for the chemical liquid according to claim 1,
wherein the specific component contains an organic substance having a molecular weight equal to or greater than 200.

27. The quality inspection method for the chemical liquid according to claim 26,
wherein the specific component contains an organic substance having a molecular weight of 300 to 1,000.

28. The quality inspection method for the chemical liquid according to claim 1, further comprising:
a specific component determination step that is performed before the step W or between the step W and the step A,
wherein the specific component determination step includes a step W3 of preparing a third container having a liquid contact portion of which at least a portion is formed of at least one kind of material selected from the group consisting of glass, a fluorine-containing polymer, and electropolished stainless steel, adopting a portion of the chemical liquid as h liquid, and washing at least a portion of the liquid contact portion of the third container by using h liquid, a step A3 of adopting a portion of the chemical liquid as i liquid and concentrating i liquid by using the washed third container so as to obtain three or more kinds of j liquids having different factors of concentration, a step B3 of performing measurement of a content of an organic substance, in which m/Z is 300 to 1,000, in j liquids by at least one kind of measurement method selected from the group consisting of high-performance liquid chromatography mass spectrometry and gas chromatography mass spectrometry, and a step C3 in which in a case where one kind of organic substance is commonly detected from all of three or more kinds of j liquids, one kind of the organic substance is determined as a specific component, and in a case where two or more kinds of organic substances are commonly detected from all of three or more kinds of j liquids, from a coefficient of correlation obtained by performing linear regression on the factors of concentration and the content of each of two or more kinds of the organic substances and a coefficient of correlation obtained by performing linear regression on the factors of concentration and the total content of organic substances in a combination of two or more kinds of the organic substances, a maximum coefficient of correlation is selected, and an organic substance or a combination of organic substances from which the maximum coefficient of correlation is obtained is determined as a specific component,
the step W3, the step A3, the step B3, and the step C3 are performed in this order,
at least the step W3 and the step A3 are performed in a clean room having cleanliness equal to or higher than class 4 specified in the International Standard ISO14644-1:2015 established by the International Organization for Standardization, and
the concentration of i liquid is performed under at least one kind of inert gas selected from the group consisting of an Ar gas, a He gas, and a $N_2$ gas or under reduced pressure.

29. The quality inspection method for the chemical liquid according to claim 28, further comprising:
a standard value determination step of determining the standard value at a point in time when the specific component determination step has finished but the step C is not yet started,
wherein the standard value determination step includes a step W4 of preparing n pieces of fourth containers each having a liquid contact portion of which at least a portion is formed of at least one kind of material selected from the group consisting of glass, a fluorine-containing polymer, and electropolished stainless steel, preparing n kinds of chemical liquids manufactured by different manufacturing methods, obtaining twice a portion of each of n kinds of the chemical liquids, naming the obtained chemical liquids as $p_1$ liquid and $p_2$ liquid respectively, and washing at least a portion of the liquid contact portion of each of the fourth containers by using each of $p_1$ liquids, a step A4 of performing concentration of each of the corresponding liquids $p_2$ by using each of the fourth containers washed with each of the liquids $p_1$ so as to obtain n kinds of liquids q, a step B4 of performing measurement of a content of a specific component in each of q liquids by at least one kind of measurement method selected from the group consisting of high-performance liquid chromatography mass spectrometry and gas chromatography mass spectrometry, a step S of evaluating a defect inhibition performance of each of n kinds of the chemical liquids by using a defect inspection device, a step T of creating a calibration curve by performing linear regression on the content of the specific component and the defect inhibition performance, and a step U of determining the content of the specific component corresponding to a predetermined defect inhibition performance as a standard value by using the calibration curve,
the step W4, the step A4, the step B4, the step S, the step T, and the step U are performed in this order,
at least the step W4 and the step A4 are performed in a clean room having cleanliness equal to or higher than class 4 specified in the International Standard ISO14644-1:2015 established by the International Organization for Standardization,
the concentration of $p_2$ liquid is performed under at least one kind of inert gas selected from the group consisting of an Ar gas, a He gas, and a $N_2$ gas or under reduced pressure, and
n represents an integer equal to or greater than 3.

30. The quality inspection method for the chemical liquid according to claim 1,
wherein the measurement includes inorganic analysis for measuring a content of an inorganic substance in c liquid, and
the inorganic analysis is measurement of a content of at least 5 or more kinds of atoms selected from a group consisting of Ag, Al, As, Au, Ba, Ca, Cd, Co, Cr, Cu, Fe, Ga, Ge, K, Li, Mg, Mn, Mo, Na, Nb, Ni, Pb, Sb, Sn, Sr, Ta, Th, Ti, Tl, V, W, Zn, and Zr in c liquid.

31. The quality inspection method for the chemical liquid according to claim 30,
wherein 5 or more kinds of the atoms contain at least two or more kinds of atoms selected from a group consisting of Al, Fe, and Ti.

* * * * *